United States Patent
Schoen et al.

(10) Patent No.: US 10,208,125 B2
(45) Date of Patent: Feb. 19, 2019

(54) ANTI-MUCIN 1 BINDING AGENTS AND USES THEREOF

(71) Applicants: Bluefin Biomedicine, Inc., Beverly, MA (US); University of Pittsburgh—of the Commonwealth System of Higher Education, Pittsburgh, PA (US)

(72) Inventors: Robert E. Schoen, Pittsburgh, PA (US); Olivera J. Finn, Pittsburgh, PA (US); Shuji Sato, Somerville, MA (US); Wan Cheung Cheung, Lexington, MA (US); Roberto D. Polakiewicz, Lexington, MA (US)

(73) Assignees: University of Pittsburgh—Of the Commonwealth System of Higher Education, Pittsburgh, PA (US); Bluefin BioMedicine, Inc., Beverly, MA (US)

( * ) Notice: Subject to any disclaimer, the term of this patent is extended or adjusted under 35 U.S.C. 154(b) by 108 days.

(21) Appl. No.: 14/904,575

(22) PCT Filed: Jul. 14, 2014

(86) PCT No.: PCT/US2014/046725
§ 371 (c)(1),
(2) Date: Jan. 12, 2016

(87) PCT Pub. No.: WO2015/009740
PCT Pub. Date: Jan. 22, 2015

(65) Prior Publication Data
US 2016/0145343 A1    May 26, 2016

Related U.S. Application Data

(60) Provisional application No. 61/846,257, filed on Jul. 15, 2013, provisional application No. 61/976,806, filed on Apr. 8, 2014, provisional application No. 61/986,511, filed on Apr. 30, 2014.

(51) Int. Cl.
*C07K 16/28* (2006.01)
*C07K 16/30* (2006.01)
*C07K 14/705* (2006.01)
*C07K 14/725* (2006.01)
*G01N 33/574* (2006.01)

(52) U.S. Cl.
CPC ...... *C07K 16/2896* (2013.01); *C07K 14/7051* (2013.01); *C07K 14/70521* (2013.01); *C07K 16/30* (2013.01); *C07K 16/3092* (2013.01); *G01N 33/57492* (2013.01); *C07K 2317/14* (2013.01); *C07K 2317/21* (2013.01); *C07K 2317/33* (2013.01); *C07K 2317/34* (2013.01); *C07K 2317/51* (2013.01); *C07K 2317/515* (2013.01); *C07K 2317/56* (2013.01); *C07K 2317/565* (2013.01); *C07K 2317/622* (2013.01); *C07K 2317/77* (2013.01); *G01N 2333/70596* (2013.01)

(58) Field of Classification Search
None
See application file for complete search history.

(56) References Cited

U.S. PATENT DOCUMENTS

| | | | |
|---|---|---|---|
| 2002/0146750 A1 | 10/2002 | Hoogenboom et al. | |
| 2002/0160502 A1* | 10/2002 | Chung | C12N 15/74 435/252.3 |
| 2003/0099647 A1 | 5/2003 | Deshpande et al. | |
| 2004/0197328 A1* | 10/2004 | Young | A61K 51/1045 424/141.1 |
| 2005/0009136 A1 | 1/2005 | Nixon et al. | |
| 2005/0084906 A1* | 4/2005 | Goetsch | A61K 47/6805 435/7.1 |
| 2005/0208585 A1 | 9/2005 | Adams et al. | |
| 2007/0014720 A1* | 1/2007 | Gazit-Bornstein | A61K 51/1027 424/1.11 |
| 2012/0058906 A1 | 3/2012 | Smider et al. | |
| 2012/0114654 A1 | 5/2012 | Classon et al. | |
| 2012/0316071 A1 | 12/2012 | Smider et al. | |

FOREIGN PATENT DOCUMENTS

| | | |
|---|---|---|
| EP | 2 281 844 A1 | 2/2011 |
| EP | 2 351 777 A1 | 8/2011 |
| WO | WO 2008/028686 | 3/2008 |
| WO | WO 2008/076379 | 6/2008 |

OTHER PUBLICATIONS

Janeway et al. (Immunobiology 5, 2001, p. 100-101) (Year: 2001).*
Rudikoff et al. (PNAS USA, 1982, 79: 1979-1983) (Year: 1982).*
Coleman et al. (Research in Immunology, 1994; 145(1): 33-36) (Year: 1994).*
Abaza et al. (Journal of Protein Chemistry, vol. 11, No. 5, 1992, pp. 433-444) (Year: 1992).*
Ibragimova and Wade (Biophysical Journal, Oct. 1999, vol. 77, pp. 2191-2198) (Year: 1999).*
Gura (Science, 1997, 278:1041-1042) (Year: 1997).*
Kaiser (Science, 2006, 313: 1370) (Year: 2006).*
(Continued)

*Primary Examiner* — Peter J Reddig
(74) *Attorney, Agent, or Firm* — Klarquist Sparkman, LLP

(57) ABSTRACT

This disclosure provides anti-MUC1 binding agents (e.g., antibodies and chimeric antigen receptors) and methods of treatment, prophylaxis, detection, and diagnosis using the same.

44 Claims, 1 Drawing Sheet
Specification includes a Sequence Listing.

(56) References Cited

OTHER PUBLICATIONS

Chames et al ("Channes", British J. of Pharmacology, 2009, 157, 220-233) (Year: 2009).*
Klobeck et al. (Nature May 3, 1984 309: 73-76), (Year: 1984).*
GENBANK® Accession No. BAC02143, retrieved from https://www.ncbi.nlm.nih.gov/protein/BAC02143 as available on Jan. 22, 2014.
International Preliminary Report on Patentability from parent PCT Application No. PCT/US2014/046725, 7 pages (dated Jan. 19, 2016).
International Search Report from parent PCT Application No. PCT/US2014/046725, 5 pages (dated Feb. 10, 2015).
Kimura et al., "MUC1 vaccine for individuals with advanced adenoma of the colon: a cancer immunoprevention feasibility study," *Cancer Prevention Research* 6(1): 18-26, published online Dec. 17, 2012.
Pietersz et al., "Comparison of the biological properties of two anti-mucin-1 antibodies prepared for imaging and therapy," *Cancer Immunology, Immunotherapy* 44(6): 323-328 (Aug. 16, 1997).
Rubinstein et al., "The MUC1 oncoprotein as a functional target: immunotoxin binding to α/β junction mediates cell killing," *International Journal of Cancer* 124(1): 46-54 (Jan. 1, 2009).
Wilkie et al., "Retargeting of human T cells to tumor-associated MUC1: the evolution of a chimeric antigen receptor," *The Journal of Immunology* 180(7): 4901-4909 (Apr. 1, 2008).
Written Opinion from parent PCT Application No. PCT/US2014/046725, 6 pages (dated Feb. 10, 2015).
UniProtKB Database Accession No. P15941, "MUC1_HUMAN," sequence version 3, entry version 153, retrieved from http://www.uniprot.org/uniprot/P15941 as available on Jun. 26, 2013.

* cited by examiner

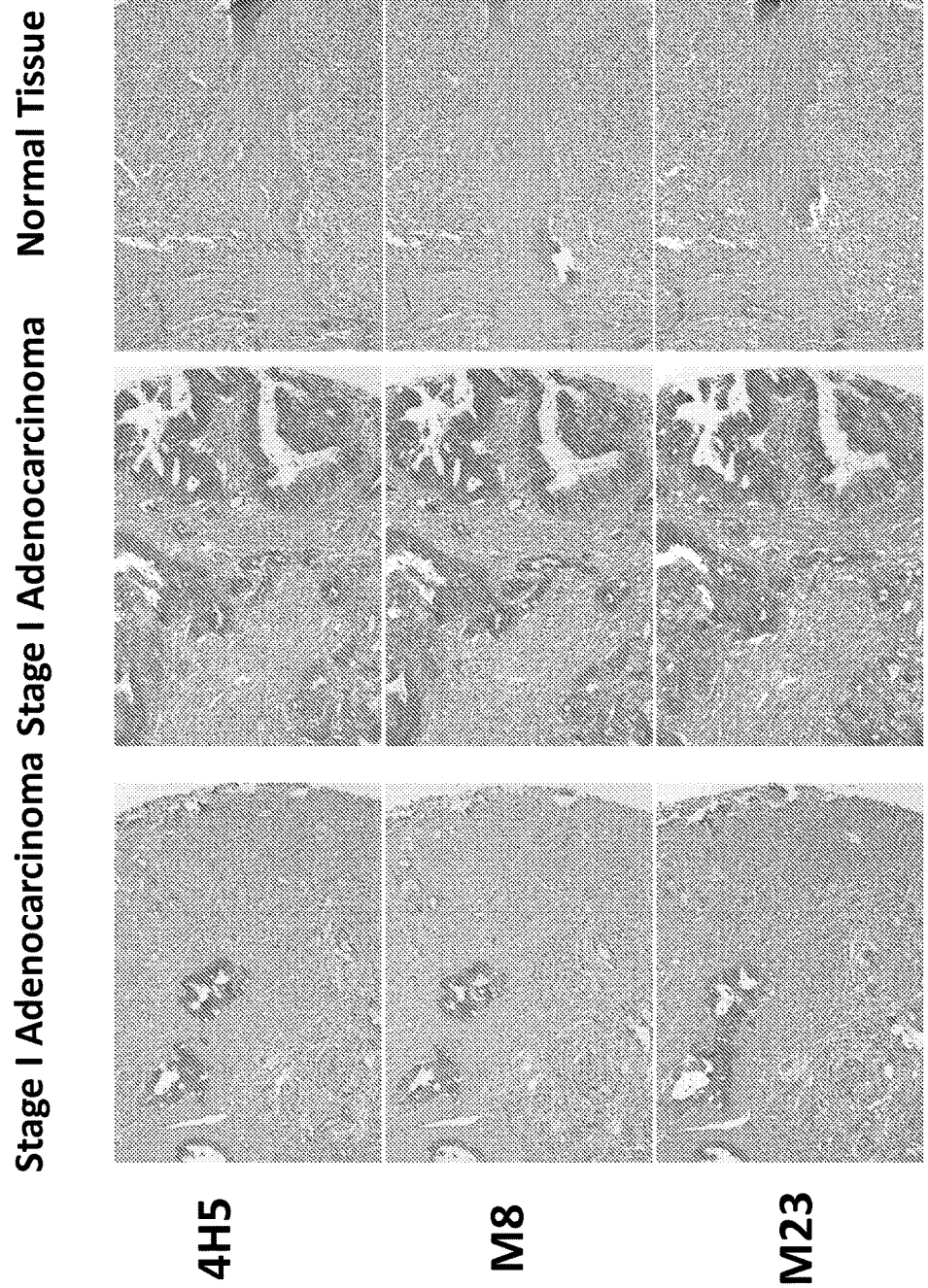

ANTI-MUCIN 1 BINDING AGENTS AND USES THEREOF

CROSS-REFERENCE TO RELATED APPLICATIONS

This application is a § 371 National Stage Application of International Patent Application No. PCT/US2014/046725, filed Jul. 15, 2014, which claims priority to U.S. provisional patent application No. 61/846,257, filed on Jul. 15, 2013, U.S. provisional patent application No. 61/976,806, filed on Apr. 8, 2014, and U.S. provisional patent application No. 61/986,511, filed on Apr. 30, 2014, the contents of each of which are incorporated herein by reference in their entirety.

BACKGROUND

Mucin 1 (MUC1) is a transmembrane protein of the mucin family, which is heavily glycosylated in its extracellular domain and is characterized by polarized expression on apical epithelial cell surfaces. In diverse cancer types, e.g., epithelial adenocarcinomas, MUC1 is overexpressed, the expression pattern loses its polarity, and it is aberrantly underglycosylated. Therefore, the abnormal MUC1 form has been considered as a therapeutic target for treatment of cancer.

SUMMARY

This disclosure is based, at least in part, on the generation of human anti-MUC1 antibodies.

Accordingly, the disclosure features in one aspect anti-MUC1 binding agents (e.g., antibodies and chimeric antigen receptors) that include:

(i) (a) a heavy chain variable region having CDRs 1, 2, and 3 having the amino acid sequences set forth in SEQ ID NOs: 7, 9, and 11, respectively, and (b) a light chain variable region having CDRs 1, 2, and 3 having a set of amino acid sequences set forth in (i) SEQ ID NOs: 150, 152, and 154, respectively; (ii) SEQ ID NOs: 159, 152, and 154, respectively; or (iii) SEQ ID NOs: 150, 152, and 163, respectively;

(ii) (a) a heavy chain variable region having CDRs 1, 2, and 3 having a set of amino acid sequences set forth in (i) SEQ ID NOs: 16, 17, and 19, respectively; (ii) SEQ ID NOs: 16, 24, and 19, respectively; (iii) SEQ ID NOs: 29, 24, and 19, respectively; (iv) SEQ ID NOs: 34, 17, and 36, respectively; (v) SEQ ID NOs: 16, 17, and 36, respectively; or (vi) SEQ ID NOs: 16, 43, and 36, respectively, and (b) a light chain variable region having CDRs 1, 2, and 3 having a set of amino acid sequences set forth in (i) SEQ ID NOs: 176, 178, and 180, respectively; (ii) SEQ ID NOs: 185, 187, and 180, respectively; or (iii) SEQ ID NOs: 185, 138, and 180, respectively;

(iii) (a) a heavy chain variable region having CDRs 1, 2, and 3 having the amino acid sequences set forth in SEQ ID NOs: 49, 51, and 53, respectively, and (b) a light chain variable region having CDRs 1, 2, and 3 having a set of amino acid sequences set forth in (i) SEQ ID NOs: 195, 197, and 199, respectively; (ii) SEQ ID NOs: 204, 205, and 199, respectively; (iii) SEQ ID NOs: 195, 205, and 199, respectively; (iv) SEQ ID NOs: 216, 217, and 199, respectively; (v) SEQ ID NOs: 195, 205, and 221, respectively; (vi) SEQ ID NOs: 195, 205, and 226, respectively; (vii) SEQ ID NOs: 230, 205, and 226, respectively; (viii) SEQ ID NOs: 236, 238, and 226, respectively; (ix) SEQ ID NOs: 247, 205, and 226, respectively; (x) SEQ ID NOs: 251, 205, and 226, respectively; or (xi) SEQ ID NOs: 257, 238, and 226, respectively;

(iv) (a) a heavy chain variable region having CDRs 1, 2, and 3 comprising a set of amino acid sequences set forth in (i) SEQ ID NOs: 59, 61, and 63, respectively; (ii) SEQ ID NOs: 59, 67, and 63, respectively; (iii) SEQ ID NOs: 59, 61, and 72, respectively; (iv) SEQ ID NOs: 59, 76, and 77, respectively; (v) SEQ ID NOs: 59, 61, and 77, respectively; (vi) SEQ ID NOs: 59, 67, and 116, respectively; (vii) SEQ ID NOs: 59, 61, and 120, respectively; (viii) SEQ ID NOs: 59, 61, and 84, respectively; (ix) SEQ ID NOs: 59, 61, and 124, respectively; (x) SEQ ID NOs: 59, 67, and 129, respectively; or (xi) SEQ ID NOs: 59, 61, and 89, respectively, and (b) a light chain variable region having CDRs 1, 2, and 3 comprising a set of amino acid sequences set forth in (i) SEQ ID NOs: 263, 265, and 267, respectively; (ii) SEQ ID NOs: 310, 311, and 267, respectively; (iii) SEQ ID NOs: 263, 265, and 316, respectively; (iv) SEQ ID NOs: 263, 265, and 320, respectively; (v) SEQ ID NOs: 263, 265, and 325, respectively; (vi) SEQ ID NOs: 263, 265, and 329, respectively; (vii) SEQ ID NOs: 335, 265, and 337, respectively; (viii) SEQ ID NOs: 263, 265, and 342, respectively; (ix) SEQ ID NOs: 263, 265, and 271, respectively; or (x) SEQ ID NOs: 263, 265, and 276, respectively;

(v) (a) a heavy chain variable region having CDRs 1, 2, and 3 comprising a set of amino acid sequences set forth in (i) SEQ ID NOs: 94, 96, and 98, respectively; (ii) SEQ ID NOs: 49, 51, and 103, respectively; or (iii) SEQ ID NOs: 49, 110, and 112, respectively, and (b) a light chain variable region having CDRs 1, 2, and 3 comprising a set of amino acid sequences set forth in (i) SEQ ID NOs: 263, 265, and 267, respectively; (ii) SEQ ID NOs: 310, 311, and 267, respectively; (iii) SEQ ID NOs: 263, 265, and 271, respectively; or (iv) SEQ ID NOs: 263, 265, and 276, respectively;

(vi) (a) a heavy chain variable region having CDRs 1, 2, and 3 comprising the amino acid sequences set forth in SEQ ID NOs: 7, 9, and 11, respectively, and (b) a light chain variable region having CDRs 1, 2, and 3 comprising the amino acid sequences set forth in SEQ ID NOs: 150, 152, and 163, respectively; and (vii) (a) a heavy chain variable region having CDRs 1, 2, and 3 comprising a set of amino acid sequences set forth in (i) SEQ ID NOs: 59, 61, and 63, respectively; (ii) SEQ ID NOs: 59, 67, and 63, respectively; (iii) SEQ ID NOs: 59, 61, and 72, respectively; (iv) SEQ ID NOs: 59, 76, and 77, respectively; (v) SEQ ID NOs: 59, 61, and 77, respectively; (vi) SEQ ID NOs: 59, 67, and 116, respectively; (vii) SEQ ID NOs: 59, 61, and 120, respectively; (viii) SEQ ID NOs: 59, 61, and 84, respectively; (ix) SEQ ID NOs: 59, 61, and 124, respectively; (x) SEQ ID NOs: 59, 67, and 129, respectively; or (xi) SEQ ID NOs: 59, 61, and 89, respectively, and (b) a light chain variable region having CDRs 1, 2, and 3 comprising a set of amino acid sequences set forth in (i) SEQ ID NOs: 263, 265, and 267, respectively; (ii) SEQ ID NOs: 310, 311, and 267, respectively; (iii) SEQ ID NOs: 263, 265, and 316, respectively; (iv) SEQ ID NOs: 263, 265, and 320, respectively; (v) SEQ ID NOs: 263, 265, and 325, respectively; (vi) SEQ ID NOs: 263, 265, and 329, respectively; (vii) SEQ ID NOs: 335, 265, and 337, respectively; or (viii) SEQ ID NOs: 263, 265, and 342, respectively; or a set of six CDRs with 20 or fewer (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer or 1) amino acid substitutions, deletions, and/or insertions relative to any set of six CDRs above. In some embodiments, the binding agent has a set of six CDRs with 20 or fewer (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer or 1) amino acid substitutions relative to any set of six CDRs above.

In another aspect, the disclosure features anti-MUC1 binding agents (e.g., antibodies) that include a heavy chain variable region having the sequence of SEQ ID NO: 5, 15, 23, 28, 33, 39, 42, 47, 57, 66, 70, 75, 80, 83, 87, 92, 101, 106, 109, 115, 119, 123, 127, 132, 141, or 145 and/or a light chain variable region comprising the sequence of SEQ ID NO: 148, 158, 162, 167, 170, 174, 184, 190, 193, 203, 208, 211, 215, 220, 225, 229, 234, 242, 246, 250, 255, 261, 270, 275, 279, 283, 291, 297, 303, 308, 315, 319, 323, 328, 333, or 340.

In another aspect, the disclosure features anti-MUC1 binding agents (e.g., antibodies) that include:

(i) a heavy chain variable region having an amino acid sequence at least 80% identical (e.g., at least 85%, 90%, 95%, 97%, 98%, 99%, or 100% identical) to SEQ ID NO: 5 and a light chain variable region having an amino acid sequence at least 80% identical (e.g., at least 85%, 90%, 95%, 97%, 98%, 99%, or 100% identical) to SEQ ID NO: 148, 158, 162, 167, or 170;

(ii) a heavy chain variable region having an amino acid sequence at least 80% identical (e.g., at least 85%, 90%, 95%, 97%, 98%, 99%, or 100% identical) to SEQ ID NO: 15, 23, 28, 33, 39, or 42 and a light chain variable region having an amino acid sequence at least 80% identical (e.g., at least 85%, 90%, 95%, 97%, 98%, 99%, or 100% identical) to SEQ ID NO: 174, 184, or 190;

(iii) a heavy chain variable region having an amino acid sequence at least 80% identical (e.g., at least 85%, 90%, 95%, 97%, 98%, 99%, or 100% identical) to SEQ ID NO: 47 and a light chain variable region having an amino acid sequence at least 80% identical (e.g., at least 85%, 90%, 95%, 97%, 98%, 99%, or 100% identical) to SEQ ID NO: 193, 203, 208, 211, 215, 220, 225, 229, 234, 242, 246, 250, or 255;

(iv) a heavy chain variable region having an amino acid sequence at least 80% identical (e.g., at least 85%, 90%, 95%, 97%, 98%, 99%, or 100% identical) to SEQ ID NO: 57, 66, 70, 75, 80, 83, 87, 115, 119, 123, 127, 132, 141, or 145 and a light chain variable region having an amino acid sequence at least 80% identical (e.g., at least 85%, 90%, 95%, 97%, 98%, 99%, or 100% identical) to SEQ ID NO: 261, 270, 275, 279, 308, 315, 319, 323, 328, 333, or 340; or (v) a heavy chain variable region having an amino acid sequence at least 80% identical (e.g., at least 85%, 90%, 95%, 97%, 98%, 99%, or 100% identical) to SEQ ID NO: 92, 101, 106, or 109 and a light chain variable region having an amino acid sequence at least 80% identical (e.g., at least 85%, 90%, 95%, 97%, 98%, 99%, or 100% identical) to SEQ ID NO: 283, 291, 297, or 303.

In another aspect, the disclosure features anti-MUC1 binding agents (e.g., antibodies) that include:

(i) a heavy chain having an amino acid sequence at least 80% identical (e.g., at least 85%, 90%, 95%, 97%, 98%, 99%, or 100% identical) to SEQ ID NO: 3 and a light chain having an amino acid sequence at least 80% identical (e.g., at least 85%, 90%, 95%, 97%, 98%, 99%, or 100% identical) to SEQ ID NO: 146, 156, 160, 165, or 168;

(ii) a heavy chain having an amino acid sequence at least 80% identical (e.g., at least 85%, 90%, 95%, 97%, 98%, 99%, or 100% identical) to SEQ ID NO: 13, 21, 26, 31, 37, or 40 and a light chain having an amino acid sequence at least 80% identical (e.g., at least 85%, 90%, 95%, 97%, 98%, 99%, or 100% identical) to SEQ ID NO: 172, 182, or 188;

(iii) a heavy chain having an amino acid sequence at least 80% identical (e.g., at least 85%, 90%, 95%, 97%, 98%, 99%, or 100% identical) to SEQ ID NO: 45 and a light chain having an amino acid sequence at least 80% identical (e.g., at least 85%, 90%, 95%, 97%, 98%, 99%, or 100% identical) to SEQ ID NO: 191, 201, 206, 209, 213, 218, 223, 227, 232, 240, 244, 248, or 253;

(iv) a heavy chain having an amino acid sequence at least 80% identical (e.g., at least 85%, 90%, 95%, 97%, 98%, 99%, or 100% identical) to SEQ ID NO: 55, 64, 68, 73, 78, 81, 85, 113, 117, 121, 125, 130, 139, or 143 and a light chain having an amino acid sequence at least 80% identical (e.g., at least 85%, 90%, 95%, 97%, 98%, 99%, or 100% identical) to SEQ ID NO: 259, 268, 273, 277, 306, 313, 317, 321, 326, 331, or 338; or (v) a heavy chain having an amino acid sequence at least 80% identical (e.g., at least 85%, 90%, 95%, 97%, 98%, 99%, or 100% identical) to SEQ ID NO: 90, 99, 104, or 107 and a light chain having an amino acid sequence at least 80% identical (e.g., at least 85%, 90%, 95%, 97%, 98%, 99%, or 100% identical) to SEQ ID NO: 281, 289, 295, or 301.

In a further aspect, the disclosure features anti-MUC1 binding agents (e.g., antibodies) that include:

(i) (a) a heavy chain variable region having CDRs 1, 2, and 3 having the amino acid sequences set forth in SEQ ID NOs: 7, 9, and 11, respectively, and (b) a light chain variable region having (i) CDR1 having an amino acid sequence selected from SEQ ID NO: 150 and SEQ ID NO: 159; (ii) CDR2 having an amino acid sequence set forth in SEQ ID NO: 152; and (iii) CDR3 having an amino acid sequence selected from SEQ ID NO: 154 and SEQ ID NO: 163;

(ii) (a) a heavy chain variable region having (i) CDR1 having an amino acid sequence selected from SEQ ID NOs: 16, 29, and 34; (ii) CDR2 having an amino acid sequence selected from SEQ ID NOs: 17, 24, and 43; and (iii) CDR3 having an amino acid sequence selected from SEQ ID NO: 19 and SEQ ID NO: 36, and (b) a light chain variable region having (i) CDR1 having an amino acid sequence selected from SEQ ID NO: 176 and SEQ ID NO: 185; (ii) CDR2 having an amino acid sequence selected from SEQ ID NOs: 138, 178, and 187; and (iii) CDR3 having an amino acid sequence set forth in SEQ ID NO: 180;

(iii) (a) a heavy chain variable region having CDRs 1, 2, and 3 having the amino acid sequences set forth in SEQ ID NOs: 49, 51, and 53, respectively, and (b) a light chain variable region having (i) CDR1 having an amino acid sequence selected from SEQ ID NOs: 195, 204, 216, 230, 236, 247, 251, and 257; (ii) CDR2 having an amino acid sequence selected from SEQ ID NOs: 197, 205, 217, and 238; and (iii) CDR3 having an amino acid sequence selected from SEQ ID NOs: 199, 221, and 226;

(iv) (a) a heavy chain variable region having (i) CDR1 having an amino acid sequence set forth in SEQ ID NO: 59; (ii) CDR2 having an amino acid sequence selected from SEQ ID NOs: 61, 67, and 76; and (iii) CDR3 having an amino acid sequence selected from SEQ ID NOs: 63, 72, 77, 84, 116, 120, 124, and 129, and (b) a light chain variable region having (i) CDR1 having an amino acid sequence selected from SEQ ID NOs: 195, 204, 216, 230, 236, 247, 251, and 257; (ii) CDR2 having an amino acid sequence selected from SEQ ID NO: 265 and SEQ ID NO: 311; and (iii) CDR3 having an amino acid sequence selected from SEQ ID NOs: 267, 271, 276, 316, 320, 325, 329, 337, and 342; or (v) (a) a heavy chain variable region having (i) CDR1 having an amino acid sequence selected from SEQ ID NO: 49 and SEQ ID NO: 94; (ii) CDR2 having an amino acid sequence selected from SEQ ID NOs: 51, 96, and 110; and (iii) CDR3 having an amino acid sequence selected from SEQ ID NOs: 98, 103, and 112, and (b) a light chain variable region having (i) CDR1 having an amino acid sequence selected from SEQ ID NOs: 285, 292, and 299; (ii) CDR2 having an amino acid sequence selected from SEQ ID NOs: 205, 287, 293, and 304; and (iii) CDR3 having an amino acid sequence set forth in SEQ ID NO: 288; or a set of six CDRs with 20 or fewer (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer or 1) amino acid substitutions (e.g., conservative amino acid substitutions), deletions (e.g., single amino acid deletions), additions, and/or insertions relative to any set of six CDRs above. In some embodiments, the binding agent has a set of six CDRs with 20 or fewer (e.g., 19 or fewer, 18 or fewer, 17 or fewer, 16 or fewer, 15 or fewer, 14 or fewer, 13 or fewer, 12 or fewer, 11 or fewer, 10 or fewer, 9 or fewer, 8 or fewer, 7 or fewer, 6 or fewer, 5 or fewer, 4 or fewer, 3 or fewer, 2 or fewer or 1) amino acid substitutions (e.g., conservative amino acid substitutions) relative to any set of six CDRs above.

In another aspect, the disclosure features anti-MUC1 binding agents (e.g., antibodies) that bind to the same epitope as an antibody selected from the group consisting of:

(a) an antibody having a heavy chain amino acid sequence consisting of SEQ ID NO: 3 and a light chain amino acid sequence consisting of SEQ ID NO: 146, 156, 160, 165, or 168;

(b) an antibody having a heavy chain amino acid sequence consisting of SEQ ID NO: 13, 21, 26, 31, 37, or 40 and a light chain amino acid sequence consisting of SEQ ID NO: 172, 182, or 188;

(c) an antibody having a heavy chain amino acid sequence consisting of SEQ ID NO: 45 and a light chain amino acid sequence consisting of SEQ ID NO: 191, 201, 206, 209, 213, 218, 223, 227, 232, 240, 244, 248, or 253;

(d) an antibody having a heavy chain amino acid sequence consisting of SEQ ID NO: 55, 64, 68, 73, 78, 81, 85, 113, 117, 121, 125, 130, 139, or 143 and a light chain amino acid sequence consisting of SEQ ID NO: 259, 268, 273, 277, 306, 313, 317, 321, 326, 331, or 338; and (e) an antibody having a heavy chain amino acid sequence consisting of SEQ ID NO: 90, 99, 104, or 107 and a light chain amino acid sequence consisting of SEQ ID NO: 281, 289, 285, or 301.

In another aspect, the disclosure features anti-MUC1 binding agents (e.g., antibodies) that compete for binding to a polypeptide having an amino acid sequence consisting of SEQ ID NO: 2 with an antibody selected from the group consisting of:

(a) an antibody having a heavy chain amino acid sequence consisting of SEQ ID NO: 3 and a light chain amino acid sequence consisting of SEQ ID NO: 146, 156, 160, 165, or 168;

(b) an antibody having a heavy chain amino acid sequence consisting of SEQ ID NO: 13, 21, 26, 31, 37, or 40 and a light chain amino acid sequence consisting of SEQ ID NO: 172, 182, or 188;

(c) an antibody having a heavy chain amino acid sequence consisting of SEQ ID NO: 45 and a light chain amino acid sequence consisting of SEQ ID NO: 191, 201, 206, 209, 213, 218, 223, 227, 232, 240, 244, 248, or 253;

(d) an antibody having a heavy chain amino acid sequence consisting of SEQ ID NO: 55, 64, 68, 73, 78, 81, 85, 113, 117, 121, 125, 130, 139, or 143 and a light chain amino acid sequence consisting of SEQ ID NO: 259, 268, 273, 277, 306, 313, 317, 321, 326, 331, or 338; and (e) an antibody having a heavy chain amino acid sequence consisting of SEQ ID NO: 90, 99, 104, or 107 and a light chain amino acid sequence consisting of SEQ ID NO: 281, 289, 285, or 301.

In another aspect, the disclosure features anti-MUC1 binding agents that include (a) a heavy chain variable region having CDRs 1, 2, and 3 that include a set of amino acid sequences set forth in (i) SEQ ID NOs: 59, 357, and 358, respectively; (ii) SEQ ID NOs: 59, 357, and 359, respectively; (iii) SEQ ID NOs: 59, 357, and 360, respectively; (iv) SEQ ID NOs: 59, 357, and 361, respectively; or (v) SEQ ID NOs: 59, 357, and 362, respectively, and (b) a light chain variable region having CDRs 1, 2, and 3 comprising a set of amino acid sequences set forth in (i) SEQ ID NOs: 263, 265, and 363, respectively; (ii) SEQ ID NOs: 364, 265, and 365, respectively; or (iii) SEQ ID NOs: 366, 367, and 368, respectively.

In a further aspect, the disclosure features anti-MUC1 binding agents that include (a) a heavy chain variable region having CDRs 1, 2, and 3 comprising the amino acid sequences set forth in SEQ ID NOs: 7, 9, and 11, respectively, and (b) a light chain variable region having CDRs 1, 2, and 3 comprising a set of amino acid sequences set forth in (i) SEQ ID NOs: 369, 152, and 154, respectively; or (ii) SEQ ID NOs: 369, 152, and 370, respectively.

Also provided are binding agents (e.g., any of the binding agents described herein) that bind specifically to the peptide of $(GVTSAPDTRPAPGSTAPPAH)_5$ (SEQ ID NO: 2) or a fragment there (e.g., a fragment that is at least 6, 7, 8, 9, 10, 11, 12, 13, 14, 15, 16, 17, 18, 19, 20, 25, 30, 35, or 40 amino acids in length), wherein the peptide of SEQ ID NO: 2 (or a fragment thereof) is not glycosylated at any of the amino acid residues.

In some embodiments of the above aspects, the binding agent (e.g., antibody) is purified.

In some embodiments of the above aspects, the binding agent (e.g., antibody) is human or humanized. In some embodiments of the above aspects, the binding agent (e.g., antibody) specifically binds to an epitope that comprises no glycosylation at one or more (e.g., one, two, three, four, or five, e.g., in any combination) of the following amino acid residues in the MUC1 repeat (HGVTSAPDTRPAPG-STAPP; SEQ ID NO: 346): threonine at amino acid position 4 of SEQ ID NO: 346, serine at amino acid position 5 of SEQ ID NO: 346, threonine at amino acid position 9 of SEQ ID NO: 346, serine at amino acid position 15 of SEQ ID NO: 346, and threonine at amino acid position 16 of SEQ ID NO: 346. In some embodiments of any of the above aspects, the binding agent (e.g., antibody) does not specifically bind to an epitope that comprises glycosylation at one or more (e.g., one, two, three, four, or five, e.g., in any combination) of the following amino acid residues in the MUC1 repeat (SEQ ID NO: 346): threonine at amino acid position 4 of SEQ ID NO: 346, serine at amino acid position 5 of SEQ ID NO: 346, threonine at amino acid position 9 of SEQ ID NO: 346, serine at amino acid position 15 of SEQ ID NO: 346, and threonine at amino acid position 16 of SEQ ID NO: 346.

Non-limiting examples of mapped glycosylation-specific epitopes that can be recognized by any of the binding agents described herein are shown in Table 3. In some embodiments of any of the binding agents described herein, the binding agent specifically binds to a glycoform of MUC1 protein expressed by a cancer cell (e.g., a pancreatic, epithelial, breast, colon, lung, ovarian, or epithelial adenocarcinoma cancer cell) and not expressed, not abundantly expressed, or is a minor (barely detectable) species in a non-cancerous cell (e.g., a non-cancerous cell derived from the same type of parent tissue, e.g., a non-cancerous pancreatic, breast, colon, lung, ovarian, or epithelial adenocarcinoma cell).

In another aspect, the disclosure features compositions that include at least one binding agent (e.g., an antibody) disclosed herein conjugated to a therapeutic agent, e.g., a cytotoxic drug or radioisotope, and/or conjugated to a reporter group, e.g., a detectable marker for diagnostic and/or imaging purposes. In some embodiments, a binding agent (e.g., any of the binding agents described herein, e.g., an antibody) that is conjugated to a detectable marker (e.g., any of the detectable markers described herein) is administered to a subject to detect (e.g., image) a cancer cell(s) (e.g., a cancer cell that expresses (e.g., overexpresses) MUC1 protein and/or has a detectable and/or elevated level of a hypoglycosylated MUC1 protein (e.g., any of the examples of MUC1 proteins described herein) that are present in the body of the subject (e.g., a human). In some embodiments, a binding agent (e.g., any of the binding agents described herein, e.g., an antibody) that is conjugated to a therapeutic agent (e.g., a cytotoxic drug or radioisotope) is administered to a subject to induce cell death of a cancer cell (e.g., a cancer cell that expresses (e.g., overexpresses) MUC1 protein and/or has a detectable and/or elevated level of a hypoglycosylated MUC1 protein (e.g., any of the examples of MUC1 proteins described herein) in the subject and/or to treat a cancer characterized as having cancer cells that express (e.g., overexpress) MUC1 protein and/or has a detectable and/or elevated level of a hypoglycosylated MUC1 protein (e.g., any of the examples of MUC1 proteins described herein).

In a further aspect, the disclosure features compositions that include at least one of the binding agents (e.g., antibodies) disclosed herein and a pharmaceutically acceptable excipient. In another aspect, the disclosure features compositions that include a purified binding agent (e.g., antibody) disclosed herein, e.g., at a concentration of 0.1 mg/ml or greater (e.g., 0.2 mg/ml or greater, 0.5 mg/ml or greater, 1 mg/ml or greater, 2 mg/ml or greater, 5 mg/ml or greater, 10 mg/ml or greater, 20 mg/ml or greater, 50 mg/ml or greater, or 100 mg/ml or greater). In some embodiments, the compositions include one or more pharmaceutically acceptable excipients. Any of the compositions described herein can include at least one of the binding agents (e.g., any of the binding agents described herein, such as antibodies) disclosed herein and an excipient or a carrier (e.g., a non-naturally occurring excipient or a non-naturally occurring carrier).

In a further aspect, the disclosure features dry (e.g., lyophilized) compositions that include a binding agent disclosed herein and, optionally, one or more pharmaceutically acceptable excipients.

In another aspect, the disclosure features polynucleotides (e.g., DNA) that encode a polypeptide chain (e.g., an antibody heavy or light chain) of any of the above binding agents. For example, the polynucleotide may include a sequence at least 80% identical (e.g., at least 85%, 90%, 95%, 97%, 98%, 99%, or 100% identical) to SEQ ID NO: 14, 22, 27, 32, 38, 41, 46, 56, 65, 69, 74, 79, 82, 86, 91, 100, 105, 108, 114, 118, 122, 126, 131, 133-135, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339. In some embodiments, the polynucleotides (e.g., DNA) do not include introns, e.g., naturally-occurring introns. The disclosure also features vectors (e.g., recombinant vectors, expression vectors) that include the above polynucleotides and a cell (e.g., an isolated cell) (e.g., recombinant cells or hybridomas) that include the above polynucleotides and/or vectors. In some embodiments, the vector is stably integrated into a chromosome of the cell (e.g., a mammalian cell, bacterial cell, or yeast cell). In some embodiments, the vector includes a polynucleotide encoding a chimeric antigen receptor that includes a polynucleotide disclosed herein or a polynucleotide sequence encoding a polypeptide disclosed herein. In some embodiments, the cell (e.g., isolated cell) is a T cell (e.g., a human T-cell) that expresses a polypeptide disclosed herein. In some embodiments, the disclosure features methods of producing binding agents (e.g., antibodies) that include culturing the cells (e.g., isolated cells) under conditions where the binding agent is expressed and collecting the binding agent.

In a further aspect, the disclosure features polynucleotides that encode a chimeric antigen receptor that include a sequence of an anti-MUC1 binding agent described above, and vectors (e.g., lentiviral or retroviral vectors) that include such polynucleotides. In another aspect, the disclosure features genetically modified cells (e.g., T cells) that express one or more chimeric antigen receptors that include a sequence of an anti-MUC1 binding agent described above.

In another aspect, the disclosure features methods of detecting a MUC1 protein (e.g., a hypoglycosylated MUC1 protein) in a sample (e.g., a sample containing mammalian cells, e.g., a biopsy sample) that include contacting a sample with a binding agent (e.g., antibody) disclosed herein and detecting binding of the agent to the sample, thereby detecting a MUC1 protein (e.g., hypoglycosylated MUC1 protein) in the sample. In any of the methods described herein, a hypoglycosylated MUC1 protein can be a MUC1 protein that lacks glycosylation or has less glycosylation (e.g., as compared to a MUC1 protein produced by a non-cancerous cell) at one or more (e.g., one, two, three, four, or five, e.g., in any combination) amino acid residues in the MUC repeat (SEQ ID NO: 346) sequences in a MUC1 protein. For example, in any of the methods described herein a hypoglycosylated MUC1 protein can be a MUC1 protein that lacks glycosylation or has less glycosylation (e.g., as compared to a MUC1 protein produced by a non-cancerous cell or cells in a healthy subject) at one or more (e.g., one, two, three, four, or five, e.g., in any combination) of threonine at amino acid position 4 of SEQ ID NO: 346, serine at amino acid position 5 of SEQ ID NO: 346, threonine at amino acid position 9 of SEQ ID NO: 346, serine at amino acid position 15 of SEQ ID NO: 346, and threonine at amino acid position 16 of SEQ ID NO: 346. Some embodiments further include recording the detection or non-detection of MUC1 protein (e.g., the presence, the detection, the non-detection, and/or level of a hypoglycosylated MUC1 protein) in the clinical records of a subject from whom the sample was obtained.

In some embodiments, the clinical record is stored on a tangible computer readable medium, e.g., a disc, magnetic tape, or computer memory.

Some embodiments further include administering any one of the binding agents described herein to a subject identified as having detectable hypoglycosylated MUC1 protein or an elevated level of a hypoglycosylated MUC1 protein (e.g., as compared to a reference level, e.g., a level of a hypoglycosylated MUC1 protein in a MUC1 protein produced by a non-cancerous cell) in his or her sample. Some embodiments further include performing further testing for the presence of cancer (e.g., any of the methods for further testing for the presence of cancer described herein) on a subject identified as having detectable hypoglycosylated MUC1 protein or an elevated level of a hypoglycosylated MUC1 protein. Additional examples of reference values are described herein. In another aspect, the disclosure features methods that include administering a binding agent or composition (e.g., a cell composition, antibody-drug conjugate, or antibody-radioisotope conjugate) disclosed herein to a subject in need thereof (e.g., a subject having, or identified or diagnosed as having a cancer characterized by overexpression and/or hypoglycosylation of MUC1 in cancer cells (e.g., a subject identified using any of the examples of methods described herein), e.g., pancreatic cancer, epithelial cancer, breast cancer, colon cancer, lung cancer, ovarian cancer, or epithelial adenocarcinoma). In some embodiments, the subject is identified as being a subject that expresses hypoglycosylated MUC1 (e.g., using any of the methods described herein) or has an elevated level of a hypoglycosylated MUC1 protein (e.g., as compared to reference level, e.g., a level of a hypoglycosylated MUC1 protein in a MUC1 protein produced by a healthy subject, a level of a hypoglycosylated MUC1 protein in MUC1 protein produced by a non-cancerous, e.g., primary, cell, or a threshold level of a hypoglycosylated MUC1 protein, in which a determined level of a hypoglycosylated MUC1 protein that is above this value indicates that the subject should be administered a binding agent described herein).

In yet another aspect, the disclosure features methods of inhibiting or decreasing proliferation of a cell (e.g., a cell that expresses (e.g., overexpresses) and/or hypoglycosylates MUC1) that include contacting the cell with a binding agent (e.g., antibody), nucleic acid, composition, or cell disclosed herein. In another aspect, the disclosure features methods of inhibiting or decreasing proliferation of a cancer cell (e.g., a cancer cell that overexpresses and/or hypoglycosylates MUC1) that include contacting the cancer cell with a binding agent (e.g., antibody), nucleic acid, composition, or cell disclosed herein. A cell can be identified as overexpressing and/or hypoglycosylating MUC1 protein (e.g., any of the examples of forms of a hypoglycosylated MUC1 protein described herein) using any of the examples of methods described herein.

Also provided are methods of imaging a cancer cell (e.g., a cancer cell that overexpresses and/or hypoglycosylates MUC1, e.g., a pancreatic, epithelial, breast, colon, lung, ovarian, or epithelial adenocarcinoma cancer cell) in a subject (e.g., a subject in need thereof, e.g., a subject identified as being at risk for developing a cancer, a subject suspected of having a cancer, or a subject already diagnosed or identified as having a cancer), that include administering to a subject a binding agent (e.g., any of the binding agents described herein, e.g., an antibody) that is conjugated to a detectable label (e.g., any of the examples of detectable labels described herein) and imaging the presence of the cancer cell by detecting the detectable label in the subject. In some embodiments, the detectable label is a fluorophore, a metalloporphyrin, a paramagnetic metal, a superparamagnetic metal, a magnetic particle (e.g., 10-20 nm in diameter), a nitroxide stable free radical, or ferrioxamine methanesulfonate. In some embodiments, the binding agents are conjugated to both a therapeutic agent and a detectable reporter group, to enable imaging of therapy, e.g., to confirm that the therapeutic agent is in the correct location in the subject and/or for ongoing monitoring of the effect of therapy, e.g., to determine the size of a solid tumor over time.

The disclosure also features the binding agents (e.g., antibodies), nucleic acids, compositions, and cells disclosed herein and the use thereof for treatment, prophylaxis, imaging, or diagnosis of a cancer (e.g., pancreatic, epithelial, breast, colon, lung, or ovarian cancer, or epithelial adenocarcinoma). In some embodiments, the cancer expresses (e.g., overexpresses) and/or hypoglycosylates MUC1. In some embodiments, the cancer is a cancer characterized by the presence of a hypoglycosylated MUC1 and/or an elevated level of a hypoglycosylated MUC1 protein (e.g., as compared to a reference level, e.g., the level of a hypoglycosylated MUC1 in a MUC1 protein produced by a healthy subject, a level of a hypoglycosylated MUC1 in a MUC1 protein produced by a non-cancerous cell, or a threshold level of a hypoglycosylated MUC1, in which a determined level of a hypoglycosylated MUC1 that is above the threshold value indicates that the subject should be administered a binding agent, should be identified as having cancer, and/or should be subjected to further testing for the presence of cancer), e.g., a MUC1 protein that lacks glycosylation or has less glycosylation (e.g., as compared to a MUC1 protein produced by a non-cancerous cell) at one or more (e.g., one, two, three, four, or five) (e.g., in any combination) amino acid residues in the MUC repeat (SEQ ID NO: 346) sequences in a MUC1 protein, in the subject.

Non-limiting examples of methods for detecting the presence of a cancer characterized by the presence of a hypoglycosylated MUC1 and/or an increased level of a hypoglycosylated MUC1 protein (e.g., as compared to a reference level, e.g., any of the examples of reference levels described herein, such as the level of a hypoglycosylated MUC1 protein in a MUC1 protein produced by a healthy subject) are described herein. Some embodiments further include selecting a subject identified as having a cancer characterized by the detection of a hypoglycosylated MUC1 protein and/or an elevated level of a hypoglycosylated MUC1 protein (e.g., as compared to any of the reference levels described herein, such as a level of a hypoglycosylated MUC1 protein in a MUC1 protein produced by a healthy subject) (e.g., using any of the examples of methods described herein).

In another aspect, the disclosure features therapeutic, prophylactic, and/or diagnostic compositions for a cancer (e.g., pancreatic, epithelial, breast, colon, lung, or ovarian cancer, or epithelial adenocarcinoma) that include a binding agent (e.g., antibody), polynucleotide, or cell disclosed herein. In some embodiments, the composition is formulated for intravenous administration. In some embodiments, the cancer expresses (e.g., overexpresses) and/or hypoglycosylates MUC1. In some embodiments, the cancer is characterized by the presence of a hypoglycosylated MUC1 and/or an elevated level of a hypoglycosylated MUC1 protein (e.g., as compared to a reference level, e.g., a level of a hypoglycosylated MUC1 protein in a MUC1 protein produced by a healthy subject) produced by the cancer cells (e.g., pancreatic, epithelial, breast, colon, lung, ovarian, or epithelial adenocarcinoma cancer cells). The hypoglycosylated MUC1 protein can be any of the specific examples of hypoglycosylated MUC1 proteins described herein.

In a further aspect, the disclosure features methods for treatment of a cancer (e.g., a cancer characterized by overexpression and/or hypoglycosylation of MUC1 in cancer cells) (e.g., pancreatic, epithelial, breast, colon, lung, or ovarian cancer, or an epithelial adenocarcinoma), that include administering a binding agent (e.g., antibody), nucleic acid, composition, or cell disclosed herein to a subject with a cancer in a therapeutically effective amount. In some embodiments, the cancer expresses (e.g., overexpresses) and/or hypoglycosylates MUC1. In some embodiments, the cancer is characterized by the presence of a hypoglycosylated MUC1 and/or an elevated level of a hypoglycosylated MUC1 protein (e.g., as compared to a reference level, e.g., a level of a hypoglycosylated MUC1 protein in a MUC1 protein produced by a healthy subject), e.g., a MUC1 protein that lacks glycosylation or has less glycosylation (e.g., as compared to a MUC1 protein produced by a non-cancerous cell) at one or more (e.g., one, two, three, four, or five) (e.g., in any combination) amino acid residues in the MUC repeat (SEQ ID NO: 346) sequences in a MUC1 protein, in the subject.

Non-limiting examples of a hypoglycosylated MUC1 protein are described herein. Non-limiting examples of methods for detecting the presence of a cancer characterized by the detection of a hypoglycosylated MUC1 and/or an elevated level of a hypoglycosylated MUC1 protein (e.g., as compared to a reference level, e.g., a level of a hypoglycosylated MUC1 protein in a MUC1 protein produced by a healthy subject) are described herein. Some embodiments further include selecting a subject identified as having a cancer characterized by the presence or expression of a hypoglycosylated MUC1 protein and/or an elevated level of a hypoglycosylated MUC1 protein (e.g., as compared to a reference level, e.g., a level of a hypoglycosylated MUC1 protein in a MUC1 protein produced by a healthy subject) (e.g., using any of the examples of methods described herein), and selectively administering to a subject identified as having a cancer characterized by the presence or expression of a hypoglycosylated MUC1 protein and/or an elevated level of a hypoglycosylated MUC1 protein (e.g., as compared to the reference level) at least one of any of the binding agents described herein.

In yet another aspect, the disclosure features methods for cancer prophylaxis (or reducing a subject's risk of developing a cancer characterized by overexpression and/or hypoglycosylation of MUC1 protein in cancer cells, e.g., pancreatic, epithelial, breast, colon, lung, or ovarian cancer, or an epithelial adenocarcinoma) (e.g., as compared to a subject at risk for developing cancer but receiving no treatment or receiving a different treatment) that include administering a binding agent (e.g., antibody), nucleic acid, composition, or cell disclosed herein to a subject in need thereof in a prophylactically effective amount. In some embodiments, the cancer expresses (e.g., overexpresses) and/or hypoglycosylates MUC1 protein. In some embodiments of any of these methods, the subject is identified as having an elevated risk of developing cancer (e.g., a subject having one or more lineal family members having a cancer characterized by overexpression and/or hypoglycosylation of MUC1 in cancer cells, e.g., pancreatic, epithelial, breast, colon, lung, or ovarian cancer, or an epithelial adenocarcinoma). In some embodiments, the cancer is characterized by the presence or expression of a hypoglycosylated MUC1 and/or an elevated level of a hypoglycosylated MUC1 protein (e.g., as compared to a reference level, e.g., a level of a hypoglycosylated MUC1 protein in a MUC1 protein produced by a healthy subject). Non-limiting examples of a hypoglycosylated MUC1 protein are described herein.

In yet another embodiment, the disclosure features methods of diagnosing a cancer (e.g., a cancer characterized by overexpression and/or hypoglycosylation of MUC1 protein in cancer cells, e.g., pancreatic, epithelial, breast, colon, lung, or ovarian cancer, or an epithelial adenocarcinoma) that include contacting a sample (e.g., a sample containing cells, e.g., a biopsy sample) from an individual (e.g., a subject suspected of having a cancer or presenting with one or more symptoms of a cancer) with a binding agent (e.g., antibody) or composition disclosed herein and detecting binding of the binding agent to a MUC1 protein (e.g., a hypoglycosylated MUC1 protein) in the sample, wherein detecting binding of the binding agent to the MUC1 protein (e.g., hypoglycosylated MUC1 protein, e.g., any of the hypoglycosylated MUC1 proteins described herein) in the sample is indicative of cancer in the individual from whom the sample was obtained. In some embodiments, the binding agent is linked to a detectable label. In some embodiments, the cancer expresses MUC1 (e.g., hypoglycosylated MUC1 protein). Some embodiments further include performing further testing for the presence of cancer (e.g., any of the examples of methods for further testing for the presence of cancer described herein) on a subject having detectable MUC1 protein (e.g., detectable hypoglycosylated MUC1 protein). Some embodiments further include administering a treatment for cancer (e.g., any of the examples of treatments for cancer, e.g., administration of a binding agent described herein) to a subject having detectable MUC1 protein (e.g., detectable hypoglycosylated MUC1 protein).

In yet another embodiment, the disclosure features methods of diagnosing a cancer (e.g., a cancer characterized by elevated levels of a hypoglycosylated MUC1 protein in cancer cells, e.g., pancreatic, epithelial, breast, colon, lung, or ovarian cancer, or an epithelial adenocarcinoma, as compared to MUC1 protein produced by non-cancerous cells) that include providing a sample (e.g., a sample containing cells, e.g., a biopsy sample) from an individual, determining the level of a hypoglycosylated MUC1 protein (e.g., any of the hypoglycosylated MUC1 proteins described herein) in the sample using any of the binding agents described herein, comparing the level of a hypoglycosylated MUC1 protein in the sample to a reference level of MUC1 protein (e.g., a level of a hypoglycosylated MUC1 protein in a MUC1 protein produced by a non-cancerous cell), and identifying a subject having an elevated level of a hypoglycosylated MUC1 protein in the sample as compared to the reference level as having a cancer (e.g., a cancer characterized by an elevated level of hypoglycosylation of MUC1 protein, e.g., pancreatic, epithelial, breast, colon, lung, or ovarian cancer). In yet another embodiment, the disclosure features methods of selecting a subject for further testing for the presence of cancer (e.g., a cancer characterized by the detection of a hypoglycosylated MUC1 protein and/or an elevated level of a hypoglycosylated MUC1 protein, e.g., pancreatic, epithelial, breast, colon, lung, or ovarian cancer) that include providing a sample (e.g., a sample containing cells, e.g., a biopsy sample) from an individual (e.g., an individual suspected of having a cancer), detecting the presence of a hypoglycosylated MUC1 protein in the sample or determining the level of a hypoglycosylated MUC1 protein in the sample using any of the binding agents described herein, and selecting an individual having detectable hypoglycosylated MUC1 protein or having an elevated level of a hypoglycosylated MUC1 protein in the sample as compared to the reference level (e.g., a level of a hypoglycosylated MUC1 protein in a MUC1 protein produced by a healthy subject) for further testing for the presence of cancer (e.g., a cancer characterized by detection of a hypoglycosylated MUC1 protein and/or an elevated level of a hypoglycosylated MUC1 protein, e.g., pancreatic, epithelial, breast, colon, lung, or ovarian cancer).

Some embodiments further include performing further testing for the presence of cancer on the selected subject. In some embodiments, the further testing for the presence of cancer includes: imaging (e.g., magnetic resonance imaging, ultrasound, radiography, nuclear medicine, computed tomography, and positron emission tomography), exploratory surgery, and/or detection of one or more additional markers (e.g., protein markers) of the cancer. In some embodiments, the binding agent is linked to a detectable label. In some embodiments, the reference level can be a level of a hypoglycosylated MUC1 protein in a sample from a healthy subject or a level of a hypoglycosylated MUC1 protein, in which a person having a level of a hypoglycosylated MUC1 protein that is greater than the level is identified as having a cancer (e.g., a cancer characterized by overexpression and/or hypoglycosylation of MUC1 protein in cancer cells).

In one aspect, the disclosure provides methods for inhibiting or decreasing cell proliferation or growth and/or inducing cell death in cancer cells (e.g., pancreatic, epithelial, breast, colon, lung, or ovarian tumor cells, or epithelial adenocarcinoma cancer cells) that express (e.g., overexpress) MUC1 proteins (e.g., hypoglycosylated MUC1 protein, e.g., any of the specific hypoglycosylated proteins described herein) that include the step of contacting the cancer cell with a binding agent (e.g., an antibody), nucleic acid, composition, or cell disclosed herein. In some embodiments, the cell death induced by the binding agent is complement-dependent cytotoxicity and/or cell-dependent cell cytotoxicity. In some embodiments, the binding agent is conjugated to a therapeutic agent (e.g., a cytotoxic agent) and the cell death is induced by the endocytosis of the binding agent into the cancer cells, which in turn triggers the death of the cancer cells.

In another aspect, the disclosure provides methods of selectively inhibiting or decreasing the proliferation or cell growth of cells (e.g., cells, e.g., cancer cells, that overexpress and/or hypoglycosylate MUC1 protein) that include the step of administering to a subject (e.g., a subject in need thereof), an effective amount of a binding agent (e.g., an antibody), nucleic acid, composition, or cell disclosed herein, thereby selectively inhibiting or decreasing proliferation or growth of such cells. In some embodiments, the cells express MUC1 (e.g., hypoglycosylated MUC1). In some embodiments, the subject has or is identified or diagnosed as having a cancer characterized by overexpression of MUC1 protein and/or the presence and/or an elevated level of a hypoglycosylated MUC1 (e.g., any of the examples of a hypoglycosylated MUC1 proteins described herein) in cancer cells, e.g., pancreatic, epithelial, breast, colon, lung, or ovarian cancer, or an epithelial adenocarcinoma. In some embodiments, the cells are pancreatic, epithelial, breast, colon, lung, ovarian, or epithelial adenocarcinoma cancer cells. Some embodiments further include identifying a subject having a cancer characterized by overexpression of MUC1 protein and/or the presence and/or an elevated level of a hypoglycosylated MUC1 (e.g., as compared to any of the examples of reference levels described herein) (e.g., using any of the examples of methods described herein).

In yet another aspect, the disclosure further provides methods of inducing cell death (e.g., death of cells, e.g., cancer cells, that overexpress and/or hypoglycosylate MUC1) that include the step of administering to a subject (e.g., a subject in need thereof) an effective amount of a binding agent (e.g., an antibody), nucleic acid, composition, or cell disclosed herein, thereby selectively inducing cell death. In some embodiments, the subject has or is identified or diagnosed as having a cancer characterized by overexpression of MUC1 protein and/or the presence and/or an elevated level of a hypoglycosylated MUC1 protein (e.g., as compared to any of the examples of reference levels described herein) in cancer cells, e.g., pancreatic, epithelial, breast, colon, lung, or ovarian cancer, or an epithelial adenocarcinoma. In some embodiments, the cell death is death of pancreatic, epithelial, breast, colon, lung, ovarian, or epithelial adenocarcinoma cancer cells.

In another aspect, the disclosure provides methods of selectively inhibiting or decreasing cell proliferation or cell growth that include the step of contacting a cell (e.g., a cancer cell such as, e.g., a pancreatic, epithelial, breast, colon, lung, ovarian, or epithelial adenocarcinoma cancer cell) that expresses (e.g., overexpresses) MUC1 protein and/or has detectable and/or an elevated level (e.g., as compared to any of the examples of reference levels described herein) of a hypoglycosylated MUC1 protein (e.g., any of the examples of MUC1 proteins described herein) with an effective amount of a binding agent (e.g., an antibody), nucleic acid, composition, or cell disclosed herein, thereby selectively inhibiting or decreasing the cell proliferation or cell growth.

The disclosure also includes methods of inducing cell death that include the step of contacting a cell (e.g., a cancer cell, e.g., a pancreatic, epithelial, breast, colon, lung, ovarian, or epithelial adenocarcinoma cancer cell) that expresses (e.g., overexpresses) MUC1 protein and/or has a detectable and/or elevated level of a hypoglycosylated MUC1 protein (e.g., any of the examples of MUC1 proteins described herein) with an effective amount of a binding agent (e.g., an antibody), nucleic acid, composition, or cell disclosed herein, thereby selectively inducing cell death.

In one embodiment, the disclosure further provides methods of treating a subject with a disease involving pathological proliferation of cells (e.g., a cancer, e.g., a cancer characterized by overexpression and/or hypoglycosylation of MUC1 in cancer cells, e.g., pancreatic, epithelial, breast, colon, lung, or ovarian cancer, or an epithelial adenocarcinoma) that include the step of administering to a subject in need thereof an effective amount of a binding agent (e.g., an antibody), nucleic acid, composition, or cell disclosed herein, thereby treating the disease. In some embodiments, the disease is characterized by expression of MUC1. In some embodiments, the subject has or is diagnosed or identified as having a disease involving pathological proliferation of cells (e.g., a cancer, e.g., a cancer characterized by overexpression and/or hypoglycosylation of MUC1 in cancer cells, e.g., pancreatic, epithelial, breast, colon, lung, or ovarian cancer, or an epithelial adenocarcinoma). In some embodiments, the disease involving pathological proliferation of cells is a cancer characterized by the presence and/or elevated level of hypophosphorylated MUC1 protein (e.g., any of the examples of hypophosphorylated MUC1 proteins described herein) in the cancer cells (e.g., as compared to any of the examples of reference levels described herein, e.g., a level of a hypoglycosylated MUC1 protein produced by a healthy subject).

In some embodiments of the above aspects, the MUC1 is hypoglycosylated.

The compositions disclosed herein can provide fully human binding agents (e.g., monoclonal antibodies or chimeric antigen receptors) against MUC1. Fully human binding agents can avoid immune responses that may occur in patients administered antibodies with non-human components. In any of the embodiments of the compositions or human binding agents described herein, a fully human binding agent can be conjugated to a cytotoxic drug or radioisotope, or can be conjugated to an agent that increases the half-life of the binding agent in vivo (e.g., human bovine serum albumin or a polymer, e.g., a polyethylene glycol). Any of the compositions described herein that include a fully human binding agent can further include a non-naturally occurring pharmaceutical excipient or carrier. Any of the fully human binding proteins described herein can contain a glycosylation pattern (and/or a phosphorylation pattern) that differs from the glycosylation pattern (and/or phosphorylation pattern) of the same binding protein produced by a human body or by a human cell in vitro.

In some embodiments of any of the methods described herein, a binding agent (e.g., any of the binding agent described herein) is bonded (e.g., covalently bonded, hydrogen bonded, or ionic bonded) to a surface (e.g., a microfluidic device, a chromatography resin, an array, polymer, or a bead). In some embodiments of any of the methods described herein, the binding agent (e.g., any of the binding agents described herein) is contacted with a sample and/or a cell and the binding of the binding agent to MUC1 protein in the sample is performed using an immunoassay (e.g., an enzyme-linked immunosorbent assay), fluorescence-assisted cell sorting, microfluidics, and chromatography.

The binding agents can bind, e.g., specifically and selectively bind to a hypoglycosylated MUC1 protein, which provides for the selective treatment of a disease associated with the unwanted proliferation of cells expressing a hypoglycosylated MUC1 (e.g., any of the examples of forms of cancer described herein). The binding agents provided herein, when administered to a subject, result in a decrease in non-specific, negative side effects that are often observed in cancer treatments (e.g., a decrease in the cell damage or cell death of cells not expressing a hypoglycosylated MUC1 protein).

Technical and scientific terms used herein have the meaning commonly understood by one of skill in the art to which the present disclosure pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of antibody technology include Greenfield, Ed., Antibodies: A Laboratory Manual, 2d Ed., Cold Spring Harbor Laboratory Press, New York (2014); Coligan et al., Eds., Current Protocols in Immunology, DOI: 10.1002/0471142735 (February 2014); and Lo, Ed., Antibody Engineering: Methods and Protocols, Humana Press, Totawa, N.J. (2004). Standard reference works setting forth the general principles of pharmacology include Goodman and Gilman's The Pharmacological Basis of Therapeutics, 11th Ed., McGraw Hill Companies Inc., New York (2006). The above reference works are incorporated by reference herein in their entireties.

As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. Where combinations of alternatives are provided (e.g., combinations of alternative CDR sequences or combinations of alternative light and/or heavy chain sequences), the description includes each combination taken individually, as well as combinations of subsets of the alternatives.

The term "hypoglycosylated MUC1" as used herein means a glycoform of MUC1 protein (e.g., human MUC1 protein) that lacks detectable glycosylation at one or more amino acid residues that typically are glycosylated in a form of MUC1 protein (e.g., human MUC1 protein) produced by a non-cancerous mammalian cell (e.g., a non-cancerous human cell) or has less glycosylation at one or more amino acids residues in a MUC1 protein as compared to a form of MUC1 protein (e.g., human MUC1 protein) produced by a non-cancerous mammalian cell (e.g., a non-cancerous human cell). The term "healthy subject" as used herein means a subject who does not have cancer, does not have an elevated risk of developing cancer, and/or is undiagnosed or not identified as having cancer.

Further aspects, advantages, and embodiments are described in more detail below.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

SEQUENCE LISTING

The Sequence Listing [Sequence Listing, Jan. 12, 2016, 365 kilobytes], submitted to the U.S. Patent and Trademark Office as an ASCII text file on Jan. 12, 2016, is incorporated by reference herein.

BRIEF DESCRIPTION OF THE DRAWING

FIG. 1 is a set micrographs of two stage I pancreatic adenocarcinomas and normal pancreatic tissue stained by immunohistochemistry with antibodies 4H5, M8, and M23.

DETAILED DESCRIPTION

This disclosure describes anti-MUC1 binding agents and compositions and methods utilizing the same.

MUC1 is a membrane-bound protein that is a member of the mucin family. Mucins are O-glycosylated proteins that play a role in forming protective mucous barriers on epithelial surfaces and also play a role in intracellular signaling.

MUC1 is expressed on the apical surface of epithelial cells that line the mucosal surfaces of many different tissues including lung, breast, stomach, and pancreas. MUC1 is proteolytically cleaved into alpha and beta subunits that form a heterodimeric complex. The N-terminal alpha subunit is believed to function in cell-adhesion, and the C-terminal beta subunit is believed to be involved in cell signaling. Overexpression, aberrant intracellular localization, and changes in glycosylation (e.g., hypoglycosylation) of this protein have been associated with diverse cancer types, including carcinomas. An example of a sequence of human MUC1 polypeptide precursor (UniProt P15941) is provided as SEQ ID NO: 1.

An example of an alpha subunit of MUC1 consists of residues 24-1097 or 28-1097 of SEQ ID NO: 1. An example of a beta subunit of MUC1 consists of residues 1098-1255 of SEQ ID NO: 1. Additionally, several naturally-occurring isoforms of MUC1 produced by alternative splicing have been identified (see UniProt P15941, version 151).

Examples of antibodies that bind to MUC1 are disclosed in Example 1. Additional antibody pairings disclosed herein are based on binding data and/or variable region homology between chains.

As used herein, by "binding agent" is meant a molecule including, without limitation, an organic molecule such as a polypeptide (e.g., an antibody, as defined herein) or a polynucleotide, or an inorganic molecule such as a small chemical molecule or a synthetic polymer, that is capable of binding to a reference target molecule. In some embodiments, the binding agent specifically binds to the reference target molecule, where the phrase "specifically binds" is defined herein. It shall be understood that the binding agent can specifically bind to an epitope located anywhere on the target molecule. Thus, a binding agent that binds to a fragment of a target molecule necessarily binds the larger target molecule (e.g., a binding agent that specifically binds an extracellular domain of MUC1 also binds to the entire (i.e., full length) MUC1 protein).

As used herein, by "specifically binding" or "specifically binds" means that a binding agent (e.g., an antibody) interacts with its target molecule (e.g., MUC1), where the interaction is dependent upon the presence of a particular structure (i.e., the antigenic determinant or epitope) on the target molecule; in other words, the reagent is recognizing and binding to a specific structure rather than to all molecules in general. By "binding fragment thereof" means a fragment or portion of a binding reagent (e.g., an antigen binding domain of an antibody) that specifically binds the target molecule. A binding agent that specifically binds to the target molecule may be referred to as a target-specific binding agent. For example, an antibody that specifically binds to a MUC1 molecule may be referred to as a MUC1-specific antibody or an anti-MUC1 antibody.

By "purified" (or "isolated") refers to a molecule such as a nucleic acid (e.g., a polynucleotide) or a polypeptide that is removed or separated from other components present in its natural environment. For example, a purified antibody is one that is separated from other components of a eukaryotic cell, bodily fluid, or culture medium. An isolated antibody-encoding polynucleotide is one that is separated from other nuclear components (e.g., histones) and/or from upstream or downstream nucleic acid sequences (e.g., an isolated antibody-encoding polynucleotide may be separated from the endogenous heavy chain or light chain promoter). An isolated nucleic acid or purified polypeptide may be at least 60% free, or at least 75% free, or at least 90% free, or at least 95% free from other components present in natural environment of the indicated nucleic acid sequence or amino acid sequence.

Native antibodies (also called immunoglobulins) are made up of two classes of polypeptide chains, light chains and heavy chains. A non-limiting antibody of the disclosure can be an intact, four immunoglobulin chain antibody comprising two heavy chains and two light chains. The heavy chain of the antibody can be of any isotype including IgM, IgG, IgE, IgA or IgD or sub-isotype including IgG1, IgG2, IgG2a, IgG2b, IgG3, IgG4, IgE1, IgE2, etc. The light chain can be a kappa light chain or a lambda light chain. A single native antibody comprises two identical copies of a light chain and two identical copies of a heavy chain. The heavy chains, which each contain one variable domain ($V_H$) and multiple constant domains, bind to one another via disulfide bonding within their constant domains to form the "stem" of the antibody. The light chains, which each contain one variable domain ($V_L$) and one constant domain, each bind to one heavy chain via disulfide binding. The variable domain of each light chain is aligned with the variable domain of the heavy chain to which it is bound. The variable regions of both the light chains and heavy chains contain three hypervariable regions sandwiched between four more conserved framework regions (FR). These hypervariable regions, known as the complementary determining regions (CDRs), form loops that comprise the principle antigen binding surface of the antibody (see Kabat, E. A. et al., Sequences of Proteins of Immunological Interest, National Institutes of Health, Bethesda, Md., (1987)). The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding domain.

Thus, as used herein, the term "antibody" is meant to include intact immunoglobulin molecules (e.g., IgG1, IgG2a, IgG2b, IgG3, IgM, IgD, IgE, IgA) for any species (e.g., human, rodent, camelid), as well as antigen binding domain fragments thereof, such as Fab, Fab', F(ab')$_2$; variants thereof such as scFv, Fv, Fd, dAb, bispecific scFvs, diabodies, linear antibodies (see U.S. Pat. No. 5,641,870; Zapata et al., 1999, Protein Eng., 8:1057-62); single-chain antibody molecules; and multispecific antibodies formed from antibody fragments; and any polypeptide that includes a binding domain which is, or is homologous to, an antibody binding domain.

By "antigen binding domain" is meant any portion of an antibody that retains specific binding activity of the intact antibody (i.e., any portion of an antibody that is capable of specific binding to an epitope on the intact antibody's target molecule). An "epitope" is smallest portion of a target molecule capable being specifically bound by the antigen binding domain of an antibody. The minimal size of an epitope may be about five or six to seven amino acids. Non-limiting antigen binding domains include the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody. Antibodies disclosed herein include but are not limited to polyclonal, monoclonal, monospecific, polyspecific antibodies and fragments thereof and chimeric antibodies that include an immunoglobulin binding domain fused to another polypeptide.

In some embodiments, an antibody that specifically binds to a target molecule provide a detection signal at least 5-, 10-, or 20-fold higher than a detection signal provided with other proteins when used in an immunochemical assay. In some embodiments, antibodies that specifically bind to a target molecule do not detect other proteins in immunochemical assays and can immunoprecipitate the target molecule from solution.

In some embodiments, an antibody (e.g., any of the examples of antibodies described herein) specifically binds to human MUC1 protein with a $K_D$ of less than $1 \times 10^{-6}$, less than $1 \times 10^{-7}$, less than $1 \times 10^{-8}$ M, less than $1 \times 10^{-9}$ M, or less than $1 \times 10^{-10}$ M (e.g., as measured using surface plasmon resonance in phosphate buffered saline).

In some embodiments an immunoglobulin chain (e.g., a heavy chain or a light chain) may include in order from amino terminus to carboxy terminus a variable region and a constant region. The variable region may include three complementarity determining regions (CDRs), with interspersed framework (FR) regions for a structure FR1, CDR1, FR2, CDR2, FR3, CDR3 and FR4. Also within the disclosure are antibodies that include heavy or light chain variable regions, framework regions and CDRs. The antibody may comprise a heavy chain constant region that comprises some or all of a CH1 region, hinge, CH2 and/or CH3 region. The antibody may comprise a light chain constant region that comprises some or all of a CL region.

Antibodies disclosed herein can be derived from any species of animal, including mammals. Non-limiting examples of native antibodies include antibodies derived from human, camelids (e.g., camels and llamas), chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Native antibodies are the antibodies produced by a host animal. "Genetically altered antibodies" refer to antibodies wherein the amino acid sequence has been varied from that of a native antibody. Because of the relevance of recombinant DNA techniques to this application, one need not be confined to the sequences of amino acids found in native antibodies; antibodies can be redesigned to obtain desired characteristics. The possible variations are many and range from the changing of just one or a few amino acids to the complete redesign of, for example, the variable or constant region. Changes in the constant region can be made to improve or alter characteristics, such as complement fixation, interaction with membranes, and other effector functions (e.g., complement-dependent cytotoxicity (CDC), antibody-dependent cellular cytotoxicity (ADCC), and antibody-dependent cell phagocytosis (ADCP)). Additionally, changes in the variable region can be made to improve or alter characteristics, such as antigen binding.

In some embodiments, the binding agent is glycosylated. For example, the binding agent can have a human glycosylation pattern, that is, a glycosylation pattern also found on native antibodies produced by the human body, or an altered or non-human glycosylation pattern. Furthermore, the binding agent may comprise a glycosylation pattern that modulates (e.g., enhances) one or more activities thereof. For example, the glycosylation pattern may enhance the binding agent's affinity towards its specific epitope, and/or its affinity towards its downstream receptors such as Fc receptors, in particular Fc gamma, Fc alpha or Fc epsilon receptors. Additionally or alternatively, the glycosylation pattern may enhance complement dependent cytotoxicity (CDC) and/or antibody-dependent cell-mediated cytotoxicity (ADCC). To this end, the glycosylation pattern of the binding agent may be engineered or optimized, for example by using specific cell lines that are capable of producing a desired glycosylation pattern. Such cell lines include, for example, K562, KG1, MUTZ-3, NM-F9 [DSM ACC2606], NM-D4 [DSM ACC2605], NM-H9D8 [DSM ACC 2806], NM-H9D8-E6 [DSM ACC 2807], NM H9D8-E6Q12 [DSM ACC 2856], and GT-2X [DSM ACC 2858]. In some embodiments, the binding agent can have a glycosylation pattern as provided when expressed in one of these cell lines.

The antibody or fragment or derivative thereof can be useful in medicine, in particular in therapy, diagnosis, prognosis and/or monitoring of a disease, in particular a disease as described herein, preferably cancer (e.g., any of the cancers described herein, e.g., a cancer characterized by overexpression and/or hypoglycosylation of MUC1 in cancer cells).

Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789,208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target molecule. In view of the assays and epitopes disclosed herein, those skilled in the art can generate or select antibodies or mixtures of antibodies that are applicable for an intended purpose and desired need.

Recombinant antibodies are also included in the present application. These recombinant antibodies are engineered to have the same amino acid sequence as the native antibodies or to have altered amino acid sequences of the native antibodies in the present application. They can be made in any expression systems including both prokaryotic and eukaryotic expression systems or using phage display methods (see, e.g., PCT Publication No. WO91/17271, PCT Publication No. WO92/01047; U.S. Pat. No. 5,969,108; U.S. Pat. No. 6,331,415; U.S. Pat. No. 7,498,024, and U.S. Pat. No. 7,485,291, which are herein incorporated by reference in their entirety).

Antibodies can be engineered in numerous ways. They can be made as single-chain antibodies (including small modular immunopharmaceuticals or SMIPs), Fab and F(ab')$_2$ fragments, etc. Antibodies can be humanized, chimerized, deimmunized, or fully human. Numerous publications set forth the many types of antibodies and the methods of engineering such antibodies. For example, see U.S. Patent Publication No. 20060099204; U.S. Pat. Nos. 6,355,245; 6,180,370; 5,693,762; 6,407,213; 6,548,640; 5,565,332; 5,225,539; 6,103,889; and 5,260,203.

The genetically altered antibodies should be functionally equivalent to the above-mentioned native antibodies. In certain embodiments, modified antibodies provide improved stability or/and therapeutic efficacy. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this application can be modified post-translationally (e.g., acetylation, and/or phosphorylation) or can be modified synthetically (e.g., the attachment of a labeling group, a cytotoxic drug, or a radiolabel).

Antibodies with engineered or variant constant or Fc regions can be useful in modulating effector functions, such as, for example, antigen-dependent cytotoxicity (ADCC) and complement-dependent cytotoxicity (CDC).

In certain embodiments, genetically altered antibodies are chimeric antibodies and humanized antibodies.

The chimeric antibody is an antibody having portions derived from different antibodies. For example, a chimeric antibody may have a variable region and a constant region derived from two different antibodies. The donor antibodies may be from different species.

The genetically altered antibodies disclosed herein include CDR grafted humanized antibodies. In one embodiment, the humanized antibody comprises heavy and/or light chain CDRs of a non-human donor immunoglobulin and heavy chain and light chain frameworks and constant regions of a human acceptor immunoglobulin. Non-limiting methods for making humanized antibody are disclosed in U.S. Pat. Nos. 5,530,101; 5,585,089; 5,693,761; 5,693,762; and 6,180,370 each of which is incorporated herein by reference in its entirety.

In some embodiments, an antibody disclosed herein will comprise substantially all of at least one, and typically two, variable domains (such as Fab, Fab', F(ab')2, Fabc, Fv) in which one or more of the CDR regions are synthetic amino acid sequences that specifically bind to the target molecule, and all or substantially all of the framework regions are those of a human immunoglobulin consensus sequence. The framework regions can also be those of a native human immunoglobulin sequence. Other CDR regions in the antibody can be selected to have human immunoglobulin consensus sequences for such CDRs or the sequence of a native human antibody. The antibody can also comprise at least a portion of an immunoglobulin constant region (Fc) of a human immunoglobulin. Often, an antibody will contain both the light chain as well as at least the variable domain of a heavy chain. The antibody also may include the CH1, hinge, CH2, CH3, and CH4 regions of the heavy chain.

In one embodiment of the disclosure, the antibody fragments are truncated chains (e.g., truncated at the carboxyl end). In certain embodiments, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dAb fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemical techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining VL- and VH-coding regions with a DNA that encodes a peptide linker connecting the VL and VH protein fragments "Fv" usually refers to the minimum antibody fragment that contains a complete antigen-recognition and -binding site. This region consists of a dimer of one heavy- and one light-chain variable domain (i.e., a VL domain and a VH domain) in tight, non-covalent association. It is in this configuration that the three CDRs of each variable domain interact to define an antigen-binding site on the surface of the $V_H$-$V_L$ dimer. Collectively, the CDRs confer antigen-binding specificity to the antibody. However, even a single variable domain (or half of an Fv comprising three CDRs specific for an antigen) has the ability to recognize and bind antigen, although likely at a lower affinity than the entire binding site. "Single-chain Fv" or "scFv" antibody fragments comprise the $V_H$ and $V_L$ domains of an antibody, wherein these domains are present in a single polypeptide chain. In certain embodiments, the Fv polypeptide further comprises a polypeptide linker between the $V_H$ and $V_L$ domains that enables the scFv to form the desired structure for antigen binding. For a review of scFv see Pluckthun in The Pharmacology of Monoclonal Antibodies, vol. 113, Rosenburg and Moore, eds. (Springer-Verlag: New York, 1994), pp. 269-315.

Papain digestion of an intact antibody produces two identical antigen-binding fragments, called "Fab" fragments, each with a single antigen-binding site, and a residual "Fc" fragment, whose name reflects its ability to crystallize readily. The Fab fragment contains the entire light chain (i.e., the constant domain (CL) and variable domain (VL) of the light chain) together with the first constant domain (CH1) and variable region (VH) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. For example, pepsin treatment of an antibody yields an F(ab')$_2$ fragment that has two antigen-combining sites and is still capable of cross-linking antigen. In other words, an F(ab')$_2$ fragment comprises two disulfide linked Fab fragments. Other chemical couplings of antibody fragments are also known.

SMIPs are a class of single-chain peptides engineered to include a target binding region and effector domain (CH2 and CH3 domains). See, e.g., U.S. Patent Application Publication No. 20050238646. The target-binding region may be derived from the variable region or CDRs of an antibody, e.g., a MUC1-specific antibody disclosed herein. Alternatively, the target-binding region is derived from a protein that binds the indicated target (e.g., a non-immunoglobulin molecule that binds to MUC1).

Bispecific antibodies may be monoclonal, human or humanized antibodies that have binding specificities for at least two different epitopes. In the present case, one of the binding specificities is for the indicated target (e.g., MUC1), the other one is for any other antigen, such as for example, a cell-surface protein or receptor or receptor subunit. In some embodiments, the binding specificities can be for independent epitopes on MUC1. Alternatively, a therapeutic agent may be placed on one arm. The therapeutic agent can be a drug, toxin, enzyme, DNA, radionuclide, etc.

In some embodiments, the antigen-binding fragment can be a diabody. The term "diabody" refers to a small antibody fragment with two antigen-binding sites, which fragment comprises a heavy-chain variable domain ($V_H$) connected to a light-chain variable domain ($V_L$) in the same polypeptide chain ($V_H$-$V_L$). Diabodies can be prepared by constructing scFv fragments with short linkers (about 5-10 residues) between the VH and VL domains such that inter-chain but not intra-chain pairing of the V domains is achieved, resulting in a multivalent fragment, i.e., a fragment having two antigen-binding sites. Since the linker is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90: 6444-6448 (1993).

Camelid antibodies refer to a unique type of antibodies that are devoid of light chain, initially discovered from animals of the camelid family. The heavy chains of these so-called heavy-chain antibodies bind their antigen by one single domain, the variable domain of the heavy immunoglobulin chain, referred to as VHH. VHHs show homology with the variable domain of heavy chains of the human VHIII family. The VHHs obtained from an immunized camel, dromedary, or llama have a number of advantages, such as effective production in microorganisms such as *Saccharomyces cerevisiae*.

In certain embodiments, single chain antibodies, and chimeric, humanized or primatized (CDR-grafted) antibodies, as well as chimeric or CDR-grafted single chain antibodies, comprising portions derived from different species, are also encompassed by the present disclosure as antigen-binding fragments of an antibody. The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., U.S. Pat. Nos. 4,816,567 and 6,331,415; U.S. Pat. No. 4,816,397; European Patent No. 0,120,694; WO 86/01533; European Patent No. 0,194,276 B1; U.S. Pat. No. 5,225,539; and European Patent No. 0,239,400 B1. See also, Newman et al., BioTechnology, 10: 1455-1460 (1992), regarding primatized antibody. See, e.g., Ladner et al., U.S. Pat. No. 4,946,778; and Bird et al., Science, 242: 423-426 (1988), regarding single chain antibodies.

In addition, functional fragments of antibodies, including fragments of chimeric, humanized, primatized or single chain antibodies, can also be produced. Functional fragments of the subject antibodies retain at least one antigen binding domain function and/or modulation function of the full-length (i.e., intact) antibody from which they are derived. Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins or conjugates having novel properties.

Human antibodies (e.g., those with fully human sequences) may be made by means known in the art, e.g., by phage display using human antibody library sequences or by use of mice genetically engineered to produce antibodies from human gene sequences. Additionally, human antibodies may be derived from antibodies or cells in circulation, e.g., using the methods described in WO 2010/011337 and/or US 2012/0308555.

Non-immunoglobulin binding polypeptides are also contemplated. For example, CDRs from an antibody disclosed herein may be inserted into a suitable non-immunoglobulin scaffold to create a non-immunoglobulin binding polypeptide. Suitable candidate scaffold structures may be derived from, for example, members of fibronectin type III and cadherin superfamilies.

Methods for identifying the CDR regions of an antibody by analyzing the amino acid sequence of the antibody are well known (see, e.g., Wu, T. T. and Kabat, E. A. (1970) J. Exp. Med. 132: 211-250; Martin et al., Methods Enzymol. 203:121-53 (1991); Morea et al., Biophys Chem. 68(1-3): 9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007)).

Also contemplated are other equivalent non-antibody molecules, such as protein binding domains, peptide aptamers (see, e.g., U.S. Pat. No. 6,004,746), DARPins (see, e.g., U.S. Pat. No. 7,417,130), tetranectins (see, e.g., US 2004/0132094), affibodies (see, e.g., U.S. Pat. No. 5,831,012), transbodies (see, e.g., US 2004/0023334), anticalins (see, e.g., U.S. Pat. No. 7,250,297), adnectins or monobodies (see, e.g., U.S. Pat. No. 6,818,418), affilins (see, e.g., U.S. Pat. No. 7,838,629), microbodies (see, e.g., U.S. Pat. No. 7,186,524) stradobodies (see, e.g., US 2010/0239633), avimers or maxibodies (see, e.g., U.S. Pat. No. 7,803,907), evibodies (see, e.g., U.S. Pat. No. 7,166,697), or fynomers (see, e.g., US 20100119446) that specifically bind to a MUC1 (e.g., a hypoglycosylated MUC1) and include one or more sequences disclosed herein (e.g., any one or more of SEQ ID NOs: 3, 5-13, 15-21, 23-26, 28-31, 33-37, 39, 40, 42-45, 47-55, 57-64, 66-68, 70-73, 75-78, 80, 81, 83-85, 87-90, 92-99, 101-104, 106, 107, 109-113, 115-117, 119-121, 123-125, 127-130, 132, 136-138, 139, 141-143, 145, 146, 148-156, 158-160, 162-165, 167, 168, 170-172, 174-182, 184-188, 190, 191, 193-201, 203-206, 208, 209, 211-213, 215-218, 220-223, 225-227, 229-232, 234-240, 242-244, 246-248, 250-253, 255-259, 261-268, 270-273, 275-277, 279-281, 283-289, 291-295, 297-301, 303-306, 308-313, 315-317, 319-321, 323-326, 328-331, 333-338, 340-342, and 358-370). Peptide aptamers, e.g., typically consist of a variable peptide loop attached at both ends to a protein scaffold. This double structural constraint generally increases the binding affinity of the peptide aptamer to levels comparable to an antibody (nanomolar range).

Other examples of binding agents include chimeric antigen receptors that specifically bind to a MUC1 (e.g., a hypoglycosylated MUC1) and include one or more sequences disclosed herein (e.g., any one or more of SEQ ID NOs: 3, 5-13, 15-21, 23-26, 28-31, 33-37, 39, 40, 42-45, 47-55, 57-64, 66-68, 70-73, 75-78, 80, 81, 83-85, 87-90, 92-99, 101-104, 106, 107, 109-113, 115-117, 119-121, 123-125, 127-130, 132, 136-138, 139, 141-143, 145, 146, 148-156, 158-160, 162-165, 167, 168, 170-172, 174-182, 184-188, 190, 191, 193-201, 203-206, 208, 209, 211-213, 215-218, 220-223, 225-227, 229-232, 234-240, 242-244, 246-248, 250-253, 255-259, 261-268, 270-273, 275-277, 279-281, 283-289, 291-295, 297-301, 303-306, 308-313, 315-317, 319-321, 323-326, 328-331, 333-338, 340-342, and 358-370).

Examples of chimeric antigen receptors include one or more antibody binding domains (e.g., an scFv that includes one or more sequences disclosed herein) linked by a transmembrane domain to at least one T cell receptor (TCR) signaling domain (e.g., a TCR zeta domain) and, optionally, one or more costimulatory signaling domains (e.g., a CD28, CD37 (4-1BB), or CD134 (OX40) signaling domain). A chimeric antigen receptor can also contain a spacer between the antibody binding domains and the transmembrane domain. Non-limiting examples of sequences that can be used for the transmembrane domain, the spacer, and the TCR signaling domain are described in, e.g., Becker et al., *Cell* 58:911-921, 1989; Goverman et al., *Cell* 60:929-939, 1990; Gross et al., *Proc. Natl. Acad. Sci. U.S.A.* 86:10024-10028, 1989; Kuwana et al., *Biochem. Biophys. Res. Commun.* 149:960-968, 1987; Letourneur et al., *Proc. Natl. Acad. Sci. U.S.A.* 88:8905-8909, 1991; Hwu et al., *J. Exp. Med.* 178:361-366, 1993; Ren-Heidenreich et al., *Cancer Immunol. Immunother.* 51:417-432, 2002; Nolan et al., *Clin. Cancer Res.* 5:3928-3941, 1999; and Zhao et al., *J. Immunol.* 183:5563-5574, 2009. Additional examples of the sequences that can be used for the transmembrane domain, the spacer, the TCR signaling domain, and the costimulatory signaling domains are described in US 2014/0134142, US 2014/0106449, US 2014/0037628, US 2013/0287752, US 2013/0287748, US 2013/0280220, US 2013/0225668, US 2012/0213783. In some embodiments, T cells expressing such a chimeric antigen receptor can be produced and used for treatment of a tumor that expresses MUC1. In an example of such a method, T cells are obtained from a subject and a chimeric antigen receptor-expressing polynucleotide is introduced into the cells, e.g., by transfection or transduction (e.g., transduction with a viral vector, e.g., a lentiviral or retroviral vector). The T cells thus transfected or transduced express the chimeric antigen receptor and can be reintroduced to the subject for treatment of a tumor that expresses MUC1.

In various embodiments, the binding agent is an antibody that specifically binds to MUC1 protein. In some embodiments, the binding agent is an antibody having one or more polypeptide sequences selected from any one of SEQ ID NOs: 3, 5-13, 15-21, 23-26, 28-31, 33-37, 39, 40, 42-45, 47-55, 57-64, 66-68, 70-73, 75-78, 80, 81, 83-85, 87-90, 92-99, 101-104, 106, 107, 109-113, 115-117, 119-121, 123-125, 127-130, 132, 136-138, 139, 141-143, 145, 146, 148-156, 158-160, 162-165, 167, 168, 170-172, 174-182, 184-188, 190, 191, 193-201, 203-206, 208, 209, 211-213, 215-218, 220-223, 225-227, 229-232, 234-240, 242-244, 246-248, 250-253, 255-259, 261-268, 270-273, 275-277, 279-281, 283-289, 291-295, 297-301, 303-306, 308-313, 315-317, 319-321, 323-326, 328-331, 333-338, 340-342, and 358-370. In various embodiments, the binding agent includes at least one complementary determining region (CDR), wherein the CDR includes a sequence selected from any one of SEQ ID NOs: 7, 9, 11, 16, 17, 19, 24, 29, 34, 36, 43, 49, 51, 53, 59, 61, 63, 67, 72, 76, 77, 84, 89, 94, 96, 98, 103, 110, 112, 116, 120, 124, 129, 138, 150, 152, 154, 159, 163, 176, 178, 180, 185, 187, 195, 197, 199, 204, 205, 216, 217, 221, 226, 230, 236, 238, 247, 251, 257, 263, 265, 267, 271, 276, 285, 287, 288, 292, 293, 299, 304, 310, 311, 316, 320, 325, 329, 335, 337, 342, and 358-370. In various embodiments, the binding agent includes at least one variable region that includes a sequence selected from any one of SEQ ID NOs: 5, 15, 23, 28, 33, 39, 42, 47, 57, 66, 70, 75, 80, 83, 87, 92, 101, 106, 109, 115, 119, 123, 127, 132, 141, 145, 148, 158, 162, 167, 170, 174, 184, 190, 193, 203, 208, 211, 215, 220, 225, 229, 234, 242, 246, 250, 255, 261, 270, 275, 279, 283, 291, 297, 303, 308, 315, 319, 323, 328, 333, and 340.

In further embodiments, the binding agent specifically binds to an epitope within SEQ ID NO: 2.

The binding agents of the present disclosure include antibodies having the amino acid sequences set forth herein (whether or not including a leader sequence), and binding agents that may include at least six contiguous amino acids encompassing the amino acid sequence of one or more CDR domains (either from the heavy chain or the light chain, or both) disclosed herein, as well as polypeptides that are at least 80% identical, or at least 85% identical, or at least 90%, 95%, 96%, 97%, 98% or 99% identical to those described above (e.g., at least 80% identical, at least 85% identical, at least 90% identical, or at least 95% identical, or at least 96%, 97%, 98% or 99% identical to any one of SEQ ID NOs: 3, 5, 13, 15, 21, 23, 26, 28, 31, 33, 37, 39, 40, 42, 45, 47, 55, 57, 64, 66, 68, 70, 73, 75, 78, 80, 81, 83, 85, 87, 90, 92, 99, 101, 104, 106, 107, 109, 113, 115, 117, 119, 121, 123, 125, 127, 130, 132, 139, 141, 143, 145, 146, 148, 156, 158, 160, 162, 165, 167, 168, 170, 172, 174, 182, 184, 188, 190, 191, 193, 201, 203, 206, 208, 209, 211, 213, 215, 218, 220, 223, 225, 227, 229, 232, 234, 240, 242, 244, 246, 248, 250, 253, 255, 259, 261, 268, 270, 273, 275, 277, 279, 281, 283, 289, 291, 295, 297, 301, 303, 306, 308, 313, 315, 317, 319, 321, 323, 326, 328, 331, 333, 338, or 340.

By "% identical" (or "% identity") for two polypeptides or two polynucleotides is intended a similarity score produced by comparing the amino acid sequences of the two polypeptides or by comparing the nucleotides sequences of the two polynucleotides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (*Advances in Applied Mathematics* 2: 482-489 (1981)) to find the best segment of similarity between two sequences.

General techniques for measuring the affinity of an antibody for an antigen include ELISA, RIA, and surface plasmon resonance. Kinetic parameters, such as dissociation constant, on rate, and off rate, may be measured by surface plasmon resonance using, e.g., a BIAcore sensor.

As used herein, the terms "polypeptide," "peptide," and "protein" are used interchangeably herein to refer to polymers of amino acids of any length. The polymer may be linear or branched, and it may comprise modified amino acids. Where the amino acid sequence is provided, unless otherwise specified, the sequence is in an N-terminal to C-terminal orientation. In some embodiments, the polymer may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides disclosed herein are based upon antibodies, the polypeptides can occur as single chains or associated chains.

The terms "polynucleotide," "nucleic acid molecule," and "nucleic acid sequence" are used interchangeably herein to refer to polymers of nucleotides of any length, and include, without limitation, DNA, RNA, DNA/RNA hybrids, and modifications thereof. Unless otherwise specified, where the nucleotide sequence is provided, the nucleotides are set forth in a 5' to 3' orientation. Thus, the nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or aralkyl. Not all linkages in a polynucleotide need be identical. The preceding description applies to all polynucleotides referred to herein, including RNA and DNA.

The present application also provides the polynucleotide molecules encoding analogs of the binding agents (e.g., antibodies) described herein. Because of the degeneracy of the genetic code, a number of different nucleic acid sequences may encode each antibody amino acid sequence. The desired nucleic acid sequences can be produced by de novo solid-phase DNA synthesis or by PCR mutagenesis of an earlier prepared variant of the desired polynucleotide. In one embodiment, the codons that are used comprise those that are typical for human, rabbit, or mouse (see, e.g., Nakamura, Y., Nucleic Acids Res. 28: 292 (2000)).

In addition, the present disclosure provides, in part, isolated polynucleotides that encode a binding agent disclosed herein, nucleotide probes that hybridize to such polynucleotides, and methods, vectors, and host cells for utilizing such polynucleotides to produce recombinant fusion polypeptides.

Some nucleotide sequences and polypeptide sequences disclosed herein may have been determined using an automated peptide sequencer. As is known in the art for any DNA sequence determined by this automated approach, any nucleotide sequence determined herein may contain some errors. Nucleotide sequences determined by automation are typically at least about 90% identical, and more typically at least about 95% to about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion. Unless otherwise indicated, each nucleotide sequence set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having a sequence disclosed herein is intended to indicate an RNA molecule having a sequence in which each deoxyribonucleotide A, G or C of the sequence has been replaced by the corresponding ribonucleotide A, G or C, and each deoxyribonucleotide T has been replaced by a ribonucleotide U.

In some embodiments, the disclosure provides isolated polynucleotides (and isolated polynucleotides complementary thereto) that include a nucleotide sequence at least about 80% identical (e.g., at least about 85%, 90%, 95%, 97%, 98%, 99%, or 100% identical) to the sequence of any one of SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339. In some embodiments, the disclosure provides an isolated polynucleotide (or an isolated polynucleotide complementary thereto) that includes a nucleotide sequence at least about 80% identical (e.g., at least about 85%, 90%, 95%, 97%, 98%, 99%, or 100% identical) identical to nucleotide sequence encoding an antibody (or fragment thereof) comprising an amino acid sequence disclosed herein.

Using the information provided herein, such as the nucleotide sequences set forth in SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, and 339, a nucleic acid molecule encoding a polypeptide binding agent (e.g., an antibody) as disclosed herein may be obtained using standard cloning and screening procedures, such as those for cloning cDNAs using mRNA as starting material.

As indicated, the present disclosure provides, in part, full-length antibodies. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present disclosure provides, in part, nucleotide sequences (e.g., DNA) encoding a heavy or light chain that includes any one of SEQ ID NOs: 3, 5, 13, 15, 21, 23, 26, 28, 31, 33, 37, 39, 40, 42, 45, 47, 55, 57, 64, 66, 68, 70, 73, 75, 78, 80, 81, 83, 85, 87, 90, 92, 99, 101, 104, 106, 107, 109, 113, 115, 117, 119, 121, 123, 125, 127, 130, 132, 139, 141, 143, 145, 146, 148, 156, 158, 160, 162, 165, 167, 168, 170, 172, 174, 182, 184, 188, 190, 191, 193, 201, 203, 206, 208, 209, 211, 213, 215, 218, 220, 223, 225, 227, 229, 232, 234, 240, 242, 244, 246, 248, 250, 253, 255, 259, 261, 268, 270, 273, 275, 277, 279, 281, 283, 289, 291, 295, 297, 301, 303, 306, 308, 313, 315, 317, 319, 321, 323, 326, 328, 331, 333, 338, or 340, with additional nucleic acid residues located 5' to the 5'-terminal residues of the coding sequence. Likewise, the disclosure provides nucleotide sequences (e.g., DNA) encoding CDRs, with additional nucleic acid residues located 5' to the 5'-terminal residues of a polynucleotide (e.g., additional nucleic acid residues that do not naturally adjoin an antibody mRNA or genomic light or heavy chain sequence in the human body) that encodes a variable region disclosed herein (e.g., a variable region including the sequence set forth in any one of SEQ ID NOs: 5, 15, 23, 28, 33, 39, 42, 47, 57, 66, 70, 75, 80, 83, 87, 92, 101, 106, 109, 115, 119, 123, 127, 132, 141, 145, 148, 158, 162, 167, 170, 174, 184, 190, 193, 203, 208, 211, 215, 220, 225, 229, 234, 242, 246, 250, 255, 261, 270, 275, 279, 283, 291, 297, 303, 308, 315, 319, 323, 328, 333, and 340) and/or CDR disclosed herein (e.g., a CDR comprising the amino acid sequence set forth in any one of SEQ ID NOs: 7, 9, 11, 16, 17, 19, 24, 29, 34, 36, 43, 49, 51, 53, 59, 61, 63, 67, 72, 76, 77, 84, 89, 94, 96, 98, 103, 110, 112, 116, 120, 124, 129, 138, 150, 152, 154, 159, 163, 176, 178, 180, 185, 187, 195, 197, 199, 204, 205, 216, 217, 221, 226, 230, 236, 238, 247, 251, 257, 263, 265, 267, 271, 276, 285, 287, 288, 292, 293, 299, 304, 310, 311, 316, 320, 325, 329, 335, 337, 342, and 358-370). Examples of leader (e.g., heterologous leader) coding sequences that may be used for expression and secretion of the binding agents disclosed herein include SEQ ID NO: 343, SEQ ID NO: 344, and sequences at least 60% identical (e.g., at least 70%, 75%, 80%, 85%, 90%, 95%, or 99% identical) to either. In some embodiments, the polynucleotides (e.g., DNA) lack one or more naturally-occurring introns, e.g., introns found between the leader- and variable region-encoding sequences, between the variable- and constant region-encoding sequences, and within the constant region-encoding sequence. In some embodiments, the polynucleotides (e.g., DNA) including one or more non-naturally-occurring introns, e.g., within the variable-region-encoding sequence.

In some embodiments, the antibody-encoding or binding agent-encoding polynucleotide comprises the nucleotide sequence set forth in SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339. In some embodiments, the antibody-encoding or binding agent-encoding polynucleotide (e.g., DNA) comprises a nucleotide sequence that encodes a variable region having the amino acid sequence set forth in any one of SEQ ID NOs: 5, 15, 23, 28, 33, 39, 42, 47, 57, 66, 70, 75, 80, 83, 87, 92, 101, 106, 109, 115, 119, 123, 127, 132, 141, 145, 148, 158, 162, 167, 170, 174, 184, 190, 193, 203, 208, 211, 215, 220, 225, 229, 234, 242, 246, 250, 255, 261, 270, 275, 279, 283, 291, 297, 303, 308, 315, 319, 323, 328, 333, and 340 and/or a CDR having the amino acid sequence set forth in any one of SEQ ID NOs: 7, 9, 11, 16, 17, 19, 24, 29, 34, 36, 43, 49, 51, 53, 59, 61, 63, 67, 72, 76, 77, 84, 89, 94, 96, 98, 103, 110, 112, 116, 120, 124, 129, 138, 150, 152, 154, 159, 163, 176, 178, 180, 185, 187, 195, 197, 199, 204, 205, 216, 217, 221, 226, 230, 236, 238, 247, 251, 257, 263, 265, 267, 271, 276, 285, 287, 288, 292, 293, 299, 304, 310, 311, 316, 320, 325, 329, 335, 337, 342, and 358-370.

In some embodiments, the polynucleotide encodes a polypeptide having the amino acid sequence set forth in any one of SEQ ID NOs: 3, 5, 13, 15, 21, 23, 26, 28, 31, 33, 37, 39, 40, 42, 45, 47, 55, 57, 64, 66, 68, 70, 73, 75, 78, 80, 81, 83, 85, 87, 90, 92, 99, 101, 104, 106, 107, 109, 113, 115, 117, 119, 121, 123, 125, 127, 130, 132, 139, 141, 143, 145, 146, 148, 156, 158, 160, 162, 165, 167, 168, 170, 172, 174, 182, 184, 188, 190, 191, 193, 201, 203, 206, 208, 209, 211, 213, 215, 218, 220, 223, 225, 227, 229, 232, 234, 240, 242, 244, 246, 248, 250, 253, 255, 259, 261, 268, 270, 273, 275, 277, 279, 281, 283, 289, 291, 295, 297, 301, 303, 306, 308, 313, 315, 317, 319, 321, 323, 326, 328, 331, 333, 338, or 340.

As indicated, polynucleotides of the present disclosure may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

Isolated polynucleotides of the disclosure may be nucleic acid molecules, DNA or RNA, which have been removed from their native environment. For example, recombinant DNA molecules contained in a vector are considered isolated for the purposes of the present disclosure. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present disclosure. Isolated nucleic acid molecules according to the present disclosure further include such molecules produced synthetically.

Isolated polynucleotides of the disclosure can include at least one modified nucleotide (e.g., any of the modified nucleotides described herein). A nucleic acid encoding an antibody or any of the other binding agents described herein can be operably linked to a heterologous promoter in an expression vector (e.g., any of the expression vectors known in the art or any of the heterologous promoters described herein).

Polynucleotides of the disclosure include the nucleic acid molecules having the sequences set forth in SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339, nucleic acid molecules comprising the coding sequence for the antibodies and binding agents of the disclosure that include a sequence different from those described above but which, due to the degeneracy of the genetic code, still encode an antibody or binding agent disclosed herein. The genetic code is well known in the art. Thus, it would be routine for one skilled in the art to generate such degenerate variants.

The disclosure further provides isolated polynucleotides comprising nucleotide sequences having a sequence complementary to one of the binding agent-encoding or antibody-encoding polynucleotides disclosed herein. Such isolated molecules, particularly DNA molecules, are useful as probes for gene mapping, by in situ hybridization with chromosomes, and for detecting expression of the antibody in tissue (e.g., human tissue), for instance, by northern blot analysis.

In some embodiments, the binding agents (e.g., antibodies) of the disclosure are encoded by at least a portion of the nucleotide sequences set forth herein. As used herein, a "portion" or "fragment" means a sequence fragment comprising a number of contiguous amino acid residues (if a polypeptide fragment (which may also be referred to herein a peptide)) or a sequence fragment comprising a number of nucleotide residues (if a polynucleotide fragment) that is less than the number of such residues in the whole sequence (e.g., a 50 nucleotide sequence is a portion of a 100 nucleotide long sequence). In other words, fragment of an indicated molecule that is smaller than the indicated molecule. For example, the binding agent-encoding polynucleotides and/or the antibody-encoding polynucleotides disclosed herein may comprise portions of intron sequences that do not encode any amino acids in the resulting binding agent or antibody. A fragment of a polynucleotide may be at least about 15 nucleotides, or at least about 20 nucleotides, or at least about 30 nucleotides, or at least about 40 nucleotides in length, which are useful as diagnostic probes and primers as discussed herein. Of course, larger fragments of about 50-1500 nucleotides in length are also useful according to the present disclosure, as are fragments corresponding to most, if not all, of the antibody-encoding or binding agent-encoding nucleotide sequence of the cDNAs having sequences set forth in SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339. By "a fragment at least 20 nucleotides in length", for example, is meant fragments that include 20 or more contiguous nucleotides from the respective nucleotide sequences from which the fragments are derived.

Polynucleotide fragments are useful as nucleotide probes for use diagnostically according to conventional DNA hybridization techniques or for use as primers for amplification of a target sequence by the polymerase chain reaction (PCR), as described, for instance, in MOLECULAR CLONING, A LABORATORY MANUAL, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference. Of course, a polynucleotide which hybridizes only to a poly A sequence or to a complementary stretch of T (or U) resides, would not be included in a polynucleotide of the disclosure used to hybridize to a portion of a nucleic acid disclosed herein, since such a polynucleotide would hybridize to any nucleic acid molecule containing a poly (A) stretch or the complement thereof (e.g., practically any double-stranded cDNA clone). Generation of such DNA fragments is routine to the skilled artisan, and may be accomplished, by way of example, by restriction endonuclease cleavage or shearing by sonication of DNA obtainable from the cDNA clone described herein or synthesized according to the sequence disclosed herein. Alternatively, such fragments can be directly generated synthetically. Any of the polynucleotide fragments described herein can be covalently attached to a detectable label (e.g., a radioisotope, a luminescent molecule, a fluorophore, or a quencher).

In another aspect, the disclosure provides an isolated polynucleotide (e.g., a nucleotide probe, e.g., a nucleotide probe that is covalently conjugated to a detectable label) that hybridizes under stringent conditions to a binding agent-encoding or a antibody-encoding polynucleotide disclosed herein (e.g., any one of SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339). The term "stringent conditions" with respect to nucleotide sequence or nucleotide probe hybridization conditions is the "stringency" that occurs within a range from about $T_m$ minus 5° C. (i.e., 5° C. below the melting temperature ($T_m$) of the probe or sequence) to about 20° C. to 25° C. below $T_m$. Typical stringent conditions are: overnight incubation at 42° C. in a solution comprising: 50% formamide, 5×.SSC (750 mM NaCl, 75 mM trisodium citrate), 50 mM sodium phosphate (pH 7.6), 5×Denhardt's solution, 10% dextran sulfate, and 20 micrograms/ml denatured, sheared salmon sperm DNA, followed by washing the filters in 0.1×SSC at about 65° C. As will be understood by those of skill in the art, the stringency of hybridization may be altered in order to identify or detect identical or related polynucleotide sequences.

By a polynucleotide or nucleotide probe that hybridizes to a reference polynucleotide is intended that the polynucleotide or nucleotide probe (e.g., DNA, RNA, or a DNA-RNA hybrid) hybridizes along the entire length of the reference polynucleotide or hybridizes to a portion of the reference polynucleotide that is at least about 15 nucleotides (nt), or to at least about 20 nt, or to at least about 30 nt, or to about 30-70 nt of the reference polynucleotide. These nucleotide probes of the disclosure are useful as diagnostic probes and primers (e.g. for PCR) as discussed herein.

Of course, polynucleotides hybridizing to a larger portion of the reference polynucleotide, for instance, a portion 50-750 nt in length, or even to the entire length of the reference polynucleotide, are useful as probes according to the present disclosure, as are polynucleotides corresponding to most, if not all, of the nucleotide sequence of the cDNAs described herein or the nucleotide sequences set forth in SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339.

As indicated, nucleic acid molecules of the present disclosure, which encode binding agents disclosed herein, may include but are not limited to those encoding the amino acid sequence of the mature intact polypeptide, by itself; fragments thereof; the coding sequence for the mature polypeptide and additional sequences, such as those encoding the leader or secretory sequence, such as a pre-, or pro- or pre-pro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence (e.g., a non-human heterologous marker sequence), such as a sequence encoding a peptide that facilitates purification of the fused polypeptide. In certain embodiments of this aspect of the disclosure, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86: 821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the binding agents and/or antibodies of the disclosure fused to an Fc domain at the N- or C-terminus.

The present disclosure further relates to variants of the nucleic acid molecules disclosed herein, which encode portions, analogs or derivatives of a binding agent or antibody disclosed herein. Variants may occur naturally, such as a natural allelic variant. By an "allelic variant" is intended one of several alternate forms of a gene occupying a given locus on a chromosome of an organism. See, e.g. GENES II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Some alterations included in the disclosure are silent substitutions, additions and deletions, which do not alter the properties and activities (e.g. specific binding activity) of the binding agent and/or antibody disclosed herein.

Further embodiments of the disclosure include isolated polynucleotides comprising a nucleotide sequence at least 80% identical, e.g., at least 85%, 90%, 95%, 96%, 97%, 98% or 99% identical, to a binding agent-encoding or antibody-encoding polynucleotide of the disclosure.

As a practical matter, whether any particular nucleic acid molecule is at least 80%, 85%, 90%, 95%, 96%, 97%, 98% or 99% identical to, for example, the nucleotide sequences set forth in SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339 or to a nucleotide sequence that encodes a polypeptide disclosed herein can be determined conventionally using known computer programs such as the Bestfit program (Wisconsin Sequence Analysis Package, Version 8 for Unix, Genetics Computer Group, University Research Park, 575 Science Drive, Madison, Wis. 53711).

Due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the cDNAs described herein, to the nucleic acid sequences set forth in SEQ ID NOs: 4, 14, 22, 27, 32, 38, 41, 46, 56, 65, 69, 74, 79, 82, 86, 91, 100, 105, 108, 114, 118, 122, 126, 131, 140, 144, 147, 157, 161, 166, 169, 173, 183, 189, 192, 202, 207, 210, 214, 219, 224, 228, 233, 241, 245, 249, 254, 260, 269, 274, 278, 282, 290, 296, 302, 307, 314, 318, 322, 327, 332, or 339 or to nucleic acid sequences encoding a polypeptide disclosed herein will encode a polypeptide having specific binding activity (e.g., in combination with a cognate heavy or light chain). In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide that retains the specific binding activity of the reference binding agent or antibody of the disclosure. This is because the skilled artisan is fully aware of amino acid substitutions that are either less likely or not likely to significantly effect protein function (e.g., replacing one aliphatic amino acid with a second aliphatic amino acid). For example, guidance concerning how to make phenotypically silent amino acid substitutions is provided in Bowie et al., "Deciphering the Message in Protein Sequences: Tolerance to Amino Acid Substitutions," *Science* 247: 1306-1310 (1990), which describes two main approaches for studying the tolerance of an amino acid sequence to change. Skilled artisans familiar with such techniques also appreciate which amino acid changes are likely to be permissive at a certain position of the protein. For example, most buried amino acid residues require nonpolar side chains, whereas few features of surface side chains are generally conserved. Other such phenotypically silent substitutions are described in Bowie et al., supra., and the references cited therein.

Methods for DNA sequencing that are well known and generally available in the art may be used to practice any polynucleotide embodiments of the disclosure. The methods may employ such enzymes as the Klenow fragment of DNA polymerase I, SEQUENASE (US Biochemical Corp, Cleveland, Ohio), Taq polymerase (Invitrogen), thermostable T7 polymerase (Amersham, Chicago, Ill.), or combinations of recombinant polymerases and proofreading exonucleases such as the ELONGASE Amplification System marketed by Gibco BRL (Gaithersburg, Md.). The process may be automated with machines such as the Hamilton Micro Lab 2200 (Hamilton, Reno, Nev.), Peltier Thermal Cycler (PTC200; MJ Research, Watertown, Mass.), ABI 377 DNA sequencers (Applied Biosystems), and 454 sequencers (Roche).

Polynucleotide sequences encoding a binding agent or antibody disclosed herein may be extended utilizing a partial nucleotide sequence and employing various methods known in the art to detect upstream sequences such as promoters and regulatory elements. For example, one method that may be employed, "restriction-site" PCR, uses universal primers to retrieve unknown sequence adjacent to a known locus (Sarkar, G., *PCR Methods Applic.* 2: 318-322 (1993)). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia et al., *Nucleic Acids Res.* 16: 8186 (1988)). The primers may be designed using OLIGO 4.06 Primer Analysis software (National Biosciences Inc., Plymouth, Minn.), or another appropriate program, to be 22-30 nucleotides in length, to have a GC content of 50% or more, and to anneal to the target sequence at temperatures about 68-72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al., 1991, PCR Methods Applic., 1:111-119). In this method, multiple restriction enzyme digestions and ligations may also be used to place an engineered double-stranded sequence into an unknown portion of the DNA molecule before performing PCR. Another method which may be used to retrieve unknown sequences is that described in Parker et al., 1991, Nucleic Acids Res., 19:3055-60). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, libraries that have been size-selected to include larger cDNAs may be used or random-primed libraries, which contain more sequences that contain the 5' regions of genes. A randomly primed library is useful for situations in which an oligo d(T) library does not yield a full-length cDNA. Genomic libraries may be useful for extension of sequence into the 5' and 3' non-transcribed regulatory regions.

Capillary electrophoresis systems, which are commercially available, may be used to analyze the size or confirm the nucleotide sequence of sequencing or PCR products. In particular, capillary sequencing may employ flowable polymers for electrophoretic separation, four different fluorescent dyes (one for each nucleotide) that are laser activated, and detection of the emitted wavelengths by a charge coupled device camera. Output/light intensity may be converted to electrical signal using appropriate software (e.g., GENOTYPER and SEQUENCE NAVIGATOR, Applied Biosystems) and the entire process from loading of samples to computer analysis and electronic data display may be computer controlled. Capillary electrophoresis is useful for the sequencing of small pieces of DNA that might be present in limited amounts in a particular sample.

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant binding agent polypeptides (e.g., antibodies) or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as encoded polypeptide in a host cell introduced with the expression vector. Thus, in an expression vector, the polynucleotide of interest is positioned for expression in the vector by being operably linked with regulatory elements such as a promoter, enhancer, poly-A tail, etc., either within the vector or in the genome of the host cell at or near or flanking the integration site of the polynucleotide of interest such that the polynucleotide of interest will be translated in the host cell introduced with the expression vector.

By "introduced" is meant that a vector is inserted into the host cell by any means including, without limitation, electroporation, fusion with a vector-containing liposomes, chemical transfection (e.g., DEAE-dextran), transformation, transvection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some embodiments, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. In the latter case, viral propagation generally will occur only in complementing virus packaging cells. Suitable systems are disclosed, for example, in Fisher-Hoch et al., 1989, Proc. Natl. Acad. Sci. USA 86:317-321; Flexner et al., 1989, Ann. N.Y. Acad Sci. 569:86-103; Flexner et al., 1990, Vaccine 8:17-21; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner-Biotechniques 6:616-627, 1988; Rosenfeld et al., 1991, Science 252:431-434; Kolls et al., 1994, Proc. Natl. Acad. Sci. USA 91:215-219; Kass-Eisler et al., 1993, Proc. Natl. Acad. Sci. USA 90:11498-11502; Guzman et al., 1993, Circulation 88:2838-2848; and Guzman et al., 1993, Cir. Res. 73:1202-1207. Techniques for incorporating DNA into such expression systems are well known to those of ordinary skill in the art. The DNA may also be "naked," as described, for example, in Ulmer et al., 1993, Science 259:1745-1749, and reviewed by Cohen, 1993, Science 259:1691-1692. The uptake of naked DNA may be increased by coating the DNA onto biodegradable beads that are efficiently transported into the cells.

The polynucleotides can be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells. The methods disclosed herein may be practiced with vectors comprising cis-acting control regions to the polynucleotide of interest. Appropriate trans-acting factors may be supplied by the host, supplied by a complementing vector or supplied by the vector itself upon introduction into the host. In certain embodiments in this regard, the vectors provide for specific expression, which may be inducible and/or cell type-specific (e.g., those inducible by environmental factors that are easy to manipulate, such as temperature and nutrient additives).

For expression, the DNA insert comprising an antibody-encoding or polypeptide-encoding polynucleotide disclosed herein can be operatively linked to an appropriate promoter (e.g., a heterologous promoter), such as the phage lambda PL promoter, the *E. coli* lac, trp and tac promoters, the SV40 early and late promoters and promoters of retroviral LTRs, to name a few. Other suitable promoters are known to the skilled artisan. The expression constructs can further contain sites for transcription initiation, termination and, in the transcribed region, a ribosome binding site for translation.

The coding portion of the mature transcripts expressed by the constructs may include a translation initiating at the beginning and a termination codon (UAA, UGA or UAG) appropriately positioned at the end of the polypeptide to be translated.

As indicated, the expression vectors may include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells; insect cells such as *Drosophila* S2 and *Spodoptera* Sf9 cells; animal cells such as CHO, COS, Bowes melanoma, and HK 293 cells; and plant cells. Appropriate culture mediums and conditions for the above-described host cells are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast *Saccharomyces cerevisiae*, a number of vectors containing constitutive or inducible promoters such as alpha factor, alcohol oxidase, and PGH may be used. For reviews, see Ausubel et al. (1989) CURRENT PROTOCOLS IN MOLECULAR BIOLOGY, John Wiley & Sons, New York, N.Y., and Grant et al., *Methods Enzymol.* 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., BASIC METHODS IN MOLECULAR BIOLOGY (1986).

Transcription of DNA encoding a binding agent or antibody of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide (e.g., binding agent or antibody) may be expressed in a modified form, such as a fusion protein (e.g., a GST-fusion), and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

In one non-limiting example, a binding agent or antibody of the disclosure may comprise a heterologous region from an immunoglobulin that is useful to solubilize proteins. For example, U.S. Pat. No. 7,253,264 discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties.

The binding agents and antibodies can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography. In some embodiments, high performance liquid chromatography ("HPLC") is employed for purification. Polypeptides of the present disclosure include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present disclosure may be glycosylated or may be non-glycosylated. In addition, polypeptides of the disclosure may also include an initial modified methionine residue, in some cases as a result of host-mediated processes.

Accordingly, in another embodiment, the disclosure provides methods for producing recombinant binding agents or antibodies by culturing a recombinant host cell (as described above) under conditions suitable for the expression of the fusion polypeptide and recovering the polypeptide. Culture conditions suitable for the growth of host cells and the expression of recombinant polypeptides from such cells are well known to those of skill in the art. See, e.g., CURRENT PROTOCOLS IN MOLECULAR BIOLOGY, Ausubel F M et al., eds., Volume 2, Chapter 16, Wiley Interscience.

The disclosure also provides immortalized cell lines that produce an antibody disclosed herein. For example, hybridoma clones, constructed as described above, that produce monoclonal antibodies to the target molecule disclosed herein are also provided.

Similarly, the disclosure includes recombinant cells producing an antibody as disclosed herein, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.).

The disclosure also provides binding agents, particularly antibodies that specifically bind to an epitope on a target molecule. Likewise, the disclosure provides epitopes useful for identifying the binding agents that specifically bind to a target molecule comprising the epitope.

Epitope mapping can be done using standard methods. For example, phage display is an in vitro selection technique in which a peptide is genetically fused to a coat protein of a bacteriophage resulting in display of a fused protein on the exterior of the virion. Biopanning of these virions by incubating the pool of phage displayed variants with a specific antibody of interest, which has been immobilized on a plate. The unbound phage is then washed away and the specifically bound phage is then eluted. The eluted phage is then amplified in *E. coli* and the process is repeated, resulting in enrichment of the phage pool in favor of the tightest binding sequences.

An advantage of this technology is that it allows for the screening of greater than $10^9$ sequences in an unbiased way. Phage display is especially useful if the immunogen is unknown or a large protein fragment.

One of the limitations to phage display includes cross-contamination between phage particles. Cross contamination between phage particles may enrich for sequences that do not specifically bind the antibody. Additionally, sequences that are not found in nature will be present in the phage displayed peptide library. These sequences may not resemble the immunizing peptide at all and may bind tightly to the antibody of interest. Retrieving sequences that do not resemble the immunizing peptide can be very confounding and it is difficult to decipher whether these peptides are contamination or unnatural peptides with high binding affinity to the antibody of interest.

Methods of Use

The binding agents of the present disclosure may be employed in various methods. For example, the binding agents of the disclosure may be used in any known assay method, such competitive binding assays, direct and indirect sandwich assays, and immunoprecipitation assays. Zola, Monoclonal Antibodies: A Manual of Techniques, pp. 147-158 (CRC Press, Inc. 1987). For use in such methods (e.g., for use in in vitro assays), the binding agents may be detectably labeled (e.g., with a fluorophore such as FITC or phycoerythrin or with an enzyme substrate, such as a substrate for horse radish peroxidase) for easy detection. As discussed herein, the binding agents of the disclosure can be used for in vivo diagnostic assays, such as in vivo imaging. In some embodiments, the antibody is labeled with a radionucleotide (such as $^3$H, $^{111}$In, $^{14}$C, $^{32}$P, or $^{123}$I) so that the cells or tissue of interest can be localized and/or imaged using immunoscintigraphy. Methods of conjugating labels to a binding agent (such as an antibody) are known in the art. In other embodiments of the disclosure, binding agents disclosed herein need not be labeled, and the presence thereof can be detected using a labeled antibody, which binds to the binding agent.

For example, provided herein are methods of detecting a MUC1 protein (e.g., a hypoglycosylated MUC1 protein) in a sample (e.g., a sample containing mammalian cells, e.g., a biopsy sample) that include contacting a sample with a binding agent (e.g., antibody) disclosed herein and detecting binding of the agent to the sample, thereby detecting a MUC1 protein (e.g., hypoglycosylated MUC1 protein) in the sample. In any of the methods described herein, a hypoglycosylated MUC1 protein can be a MUC1 protein that lacks glycosylation or has less glycosylation (e.g., as compared to a MUC1 protein produced by a non-cancerous cell) at one or more (e.g., one, two, three, four, or five, e.g., in any combination) amino acid residues in the MUC repeat (SEQ ID NO: 346) sequences in a MUC1 protein. For example, in any of the methods described herein a hypoglycosylated MUC1 protein can be a MUC1 protein that lacks glycosylation or has less glycosylation (e.g., as compared to a MUC1 protein produced by a non-cancerous cell or cells in a healthy subject) at one or more (e.g., one, two, three, four, or five, e.g., in any combination) of threonine at amino acid position 4 of SEQ ID NO: 346, serine at amino acid position 5 of SEQ ID NO: 346, threonine at amino acid position 9 of SEQ ID NO: 346, serine at amino acid position 15 of SEQ ID NO: 346, and threonine at amino acid position 16 of SEQ ID NO: 346. Some embodiments further include recording the detection or non-detection of MUC1 protein (e.g., the presence, the detection, the non-detection, and/or level of a hypoglycosylated MUC1 protein) in the clinical records of a subject from whom the sample was obtained. In some embodiments, the clinical record is stored on a computer readable medium, e.g., a disc, tape, or computer memory. Some embodiments further include administering any one of the binding agents described herein to a subject identified as having detectable hypoglycosylated MUC1 protein or an elevated level of a hypoglycosylated MUC1 protein (e.g., as compared to a reference level, e.g., a level of a hypoglycosylated MUC1 protein in a MUC1 protein produced by a non-cancerous cell) in his or her sample. Some embodiments further include performing further testing for the presence of cancer (e.g., any of the methods for further testing for the presence of cancer described herein) on a subject identified as having detectable hypoglycosylated MUC1 protein or an elevated level of a hypoglycosylated MUC1 protein. Additional examples of reference values are described herein.

In another aspect, the disclosure features methods that include administering a binding agent or composition (e.g., a cell composition, antibody-drug conjugate, or antibody-radioisotope conjugate) disclosed herein to a subject in need thereof (e.g., a subject having, or identified or diagnosed as having a cancer characterized by overexpression and/or hypoglycosylation of MUC1 in cancer cells (e.g., a subject identified using any of the examples of methods described herein), e.g., pancreatic cancer, epithelial cancer, breast cancer, colon cancer, lung cancer, ovarian cancer, or epithelial adenocarcinoma). In some embodiments, the subject is identified as being a subject that expresses hypoglycosylated MUC1 (e.g., using any of the methods described herein) or has an elevated level of a hypoglycosylated MUC1 protein (e.g., as compared to reference level, e.g., a level of a hypoglycosylated MUC1 protein in a MUC1 protein produced by a healthy subject, a level of a hypoglycosylated MUC1 protein in MUC1 protein produced by a non-cancerous, e.g., primary, cell, or a threshold level of a hypoglycosylated MUC1 protein, in which a determined level of a hypoglycosylated MUC1 protein that is above this value indicates that the subject should be administered a binding agent described herein).

In yet another aspect, the disclosure features methods of inhibiting or decreasing proliferation of a cell (e.g., a cell that expresses (e.g., overexpresses) and/or hypoglycosylates MUC1) that include contacting the cell with a binding agent (e.g., antibody), nucleic acid, composition, or cell disclosed herein. In another aspect, the disclosure features methods of inhibiting or decreasing proliferation of a cancer cell (e.g., a cancer cell that overexpresses and/or hypoglycosylates MUC1) that include contacting the cancer cell with a binding agent (e.g., antibody), nucleic acid, composition, or cell disclosed herein. A cell can be identified as overexpressing and/or hypoglycosylating MUC1 protein (e.g., any of the examples of forms of a hypoglycosylated MUC1 protein described herein) using any of the examples of methods described herein.

Also provided are methods of imaging a cancer cell (e.g., a cancer cell that overexpresses and/or hypoglycosylates MUC1, e.g., a pancreatic, epithelial, breast, colon, lung, ovarian, or epithelial adenocarcinoma cancer cell) in a subject (e.g., a subject in need thereof, e.g., a subject identified as being at risk for developing a cancer, a subject suspected of having a cancer, or a subject already diagnosed or identified as having a cancer), that include administering to a subject a binding agent (e.g., any of the binding agents described herein, e.g., an antibody) that is conjugated to a detectable label (e.g., any of the examples of detectable labels described herein) and imaging the presence of the cancer cell by detecting the detectable label in the subject. In some embodiments, the detectable label is a fluorophore, a metalloporphyrin, a paramagnetic metal, a superparamagnetic metal, a magnetic particle (e.g., 10-20 nm in diameter), a nitroxide stable free radical, or ferrioxamine methanesulfonate, or a metal, e.g., gold.

The methods of detection and diagnosis may be performed on any biological sample (e.g., a sample containing mammalian cells), e.g., a sample from an individual having a cancer or suspected of having a cancer. The biological sample can be, e.g., a biopsy (e.g., needle biopsy), tissue section, or a bodily fluid (e.g., lung gavage, urine, saliva, blood, tears, semen, or breast milk).

The antibody may also be used as staining reagent in pathology, following techniques well known in the art.

In another aspect, the disclosure provides methods for detecting a MUC1 polypeptide (e.g., a hypoglycosylated MUC1 polypeptide). The methods include contacting a sample (e.g., a sample containing mammalian cells, e.g., a biopsy sample) suspected of containing MUC1 (e.g., hypoglycosylated MUC1) with a binding agent disclosed herein and detecting specific binding of the binding agent to the sample, wherein presence of specific binding of the binding agent to the sample identifies the sample as containing MUC1 polypeptide (e.g., hypoglycosylated MUC1 protein).

Such detection of specific binding by the binding agent to the sample (e.g., detection of a binding agent:sample complex) may be made by any known method including, without limitation, western blotting analysis, immunohistochemistry (IHC) analysis, immunofluorescence (IF) analysis, flow cytometry analysis, FACS analysis, ELISA, and immunoprecipitation. See, generally, Immunological Methods, Vols. I and II (Lefkovits and Pernis, eds., Academic Press, N Y, 1979 and 1981, herein incorporated by reference.

As used herein, an "individual," also referred to herein as a "subject," or "patient" is a human or non-human animal. Non-human animals include, without limitation, to, farm animals (such as cows, pigs, and chicken), domestic animals (such as cats, parrots, turtles, lizards, dogs, and horses), primates (such as chimpanzees and gorillas), and rodents (such as mice and rats). The patient may or may not be afflicted with a condition (e.g., a cancer) and/or may or may not presently show symptoms. In some embodiments, the subject has a cancer or suspected cancer. In some embodiments, the subject is at risk for a cancer. In some embodiments, the subject is undergoing or has undergone additional treatment (e.g., treatment with radiotherapy or chemotherapy).

Cellular extracts of the foregoing biological samples may be prepared, either crude or partially (or entirely) purified, in accordance with standard techniques, and used in the methods of the disclosure. Alternatively, biological samples comprising whole cells may be utilized in assay formats such as immunohistochemistry (IHC), flow cytometry (FC), and immunofluorescence (IF).

The binding agents disclosed herein may be used for therapeutic treatment of cancer in patients. The binding agents can be naked antibodies. In other embodiments, the binding agents can be antibodies that are conjugated (e.g., covalently bonded, e.g., covalently bonded through a linker moiety, e.g., a peptide linker moiety) to a therapeutic agent, e.g., a cytotoxic drug. The term cytotoxic drug refers to any agent that kills cells for example, without being limited, a radioactive isotope. The antibodies can be used to target other molecules to the cancer cells. Examples for cytotoxic drugs are, without limitation, maytansinoids (e.g., emtansine, mertansine), calicheamicins (e.g., ozogamicin), auristatins (e.g., monomethyl auristatin E), pyrrolobenzodiazepines, ansamitocins, doxorubicins, daunorubicins, taxanes, bromodeoxyuridine (BUdR), 5-iododeoxyuridine (IUdR), bromodeoxycytidine, fluorodeoxyuridine (FudR), hydroxyurea, and cisplatin. Additional information regarding cytotoxic agents, linkers, and production of antibody-drug conjugates may be found, e.g., in WO 2013/055990, WO 2013/055993, WO 2012/123423, WO 2012/041805, WO 2011/130613, WO 2011/130616, WO 2009/117531, WO 2007/103288, WO 2007/011968, WO 2007/008603, WO 2007/008848, WO 2006/132670, WO 2006/065533, WO 2005/084390, WO 2005/082023, WO 2005/081711, WO 2005/077090, WO 2005/070457, WO 2004/010957, WO 2003/026577, WO 2012/177837, WO 2012/1445112, WO 2012/138749, WO 2012/135517, WO 2012/135522, WO 2012/128868, WO 2012/112708, WO 2012/112687, WO 2012/078868, WO 2012/061590, WO 2010/141566, WO 2010/126551, WO 2010/126552, WO 2010/091150, WO 2009/134870, WO 2009/134977, WO 2009/134952, WO 2009/134976, WO 2009/080831, WO 2007/056550, WO 2007/024536, WO 2006/086733, WO 2006/078809, WO 2006/078368, WO 2005/037992, WO 2005/020883, WO 2004/110498, WO 2004/103272, WO 2004/016801, WO 2004/013093, WO 2002/098883, and WO 2001/024763, each of which are incorporated herein by reference in its entirety. Examples of methods that can be used to conjugate a therapeutic agent (e.g., a cytotoxic agent) and/or a detectable label to a binding agent (e.g., an antibody) are described in Greg T. Hermanson, Bioconjugate Techniques, Third Edition, 2013, Elsevier, Waltham, Mass. For example, a therapeutic agent and/or a detectable label can be conjugated to a binding agent (e.g., an antibody) using, e.g., NHS ester-maleimide-mediated conjugation, glutaraldehyde-mediated conjugation, or reductive amination-mediated conjugation.

In some embodiments, a cytotoxic drug is conjugated to a binding agent (e.g., any of the binding agents described herein) through a bond that is sensitive to irradiation (e.g., near infra-red irradiation). For example, the binding agent can be conjugated or bound to a nanoparticle or vesicle containing the cytotoxic drug, and once the binding agent is located proximal to the cancer cells in the body of a subject, the specific area encompassing the cancer cells is irradiated with near infra-red light (as described in, e.g., Melancon et al., *Acc. Chem. Res.* 44:947-956, 2011, Zasadzinski et al., U.S. Patent Application Publication No. 2011/0052671) or UV light (Puneet Kollipara et al., *Chem. Eng. News* 91:10, 2013) to release the drug in the vicinity of the cancer cells.

As used herein, by an "effective amount" is an amount or dosage sufficient to effect beneficial or desired results including halting, slowing, halting, retarding, or inhibiting progression of a neoplasm, e.g., a cancer. An effective amount will vary depending upon, e.g., an age and a body weight of a subject to which the a binding agent, binding agent-encoding polynucleotide, vector comprising the polynucleotide and/or compositions thereof is to be administered, a severity of symptoms and a route of administration, and thus administration is determined on an individual basis. In general, the daily adult dosage for oral administration is about 0.1 to 1000 mg, given as a single dose or in divided doses. For continuous intravenous administration, the compositions can be administered in the range of 0.01 µg/kg/min to 1.0 µg/kg/min, desirably 0.025 µg/kg/min to 0.1 µg/kg/min.

An effective amount can be administered in one or more administrations. By way of example, an effective amount of a binding agent is an amount sufficient to ameliorate, stop, stabilize, reverse, inhibit, slow and/or delay progression of a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount of a binding agent may vary, depending on, inter alia, patient history as well as other factors such as the type (and/or dosage) of binding agent used.

Effective amounts and schedules for administering the binding agents, binding agent-encoding polynucleotides, and/or compositions disclosed herein may be determined empirically, and making such determinations is within the skill in the art. Those skilled in the art will understand that the dosage that must be administered will vary depending on, for example, the mammal that will receive the binding agents, binding agent-encoding polynucleotides, and/or compositions disclosed herein, the route of administration, the particular type of binding agents, binding agent-encoding polynucleotides, and/or compositions disclosed herein used and other drugs being administered to the mammal. Where the patient is administered an antibody and/or a composition comprising an antibody, guidance in selecting appropriate doses for antibody is found in the literature on therapeutic uses of antibodies, e.g., Handbook of Monoclonal Antibodies, Ferrone et al., eds., Noges Publications, Park Ridge, N. J., 1985, ch. 22 and pp. 303-357; Smith et al., Antibodies in Human Diagnosis and Therapy, Haber et al., eds., Raven Press, New York, 1977, pp. 365-389.

A typical daily dosage of an effective amount of a binding agent used alone might range from about 1 µg/kg to up to 100 mg/kg of body weight or more per day, depending on the factors mentioned above. Generally, any of the following doses may be used: a dose of at least about 50 mg/kg body weight; at least about 10 mg/kg body weight; at least about 3 mg/kg body weight; at least about 1 mg/kg body weight; at least about 750 µg/kg body weight; at least about 500 µg/kg body weight; at least about 250 µg/kg body weight; at least about 100 µg/kg body weight; at least about 50 µg/kg body weight; at least about 10 µg/kg body weight; at least about 1 µg/kg body weight, or more, is administered. In some embodiments, a dose of a binding agent (e.g., antibody) provided herein is between about 0.01 mg/kg and about 50 mg/kg, between about 0.05 mg/kg and about 40 mg/kg, between about 0.1 mg and about 30 mg/kg, between about 0.1 mg and about 20 mg/kg, between about 0.5 mg and about 15 mg, or between about 1 mg and 10 mg. In some embodiments, the dose is between about 1 mg and 5 mg. In some alternative embodiments, the dose is between about 5 mg and 10 mg.

In some embodiments, the methods described herein further comprise the step of treating the subject with an additional form of therapy. In some embodiments, the additional form of therapy is an additional anti-cancer composition. In some embodiments the methods described herein further comprise the step of treating the subject with radiotherapy, a chemotherapeutic compound, and/or a kinase inhibitor. In some embodiments, the methods described herein further comprise the step of treating the subject with an inhibitor of the PI3K-AKT mTOR pathway, e.g., rapamycin, temsirolimus, everolimus, ridaforolimus, Torin1, Torin2, PP242, KU63794, WYE354, NVP-BEZ235, XL765, GDC-0491, GDC-0980, GSK2126458, AZD8055, OSI-027, CH5132799, PF-05212384, or ZSTK474. See also WO 2012/054748; U.S. Pat. No. 8,394,818; McCubrey et al., 2012, Oncotarget, 3:1068-1111. In some embodiments the binding agent (e.g., antibody), binding agent-encoding polypeptide or vector is administered at substantially the same time as the additional anti-cancer composition. In some embodiments, the binding agent (e.g., antibody), binding agent-encoding polypeptide, or vector is formulated together with one or more additional anti-cancer compositions.

The methods described herein (including therapeutic methods) can be accomplished by a single direct injection or infusion at a single time point or multiple time points to a single or multiple sites. Administration can also be nearly simultaneous to multiple sites. Frequency of administration may be determined and adjusted over the course of therapy, and is based on accomplishing desired results. In some cases, sustained continuous release formulations of binding agents (including antibodies), polynucleotides, and pharmaceutical compositions disclosed herein may be appropriate. Various formulations and devices for achieving sustained release are known in the art.

The binding agent (e.g., an antibody), binding agent-encoding polynucleotide, and/or vector containing such a polynucleotide may be administered to the patient in a carrier; preferably a pharmaceutically-acceptable carrier (e.g., a non-natural pharmaceutically-acceptable carrier). Thus, in further aspects, the disclosure provides a composition (e.g., a pharmaceutical composition) comprising a pharmaceutically acceptable carrier (e.g., a non-naturally occurring carrier) and (a) a binding agent disclosed herein, (b) a binding agent-encoding polynucleotide disclosed herein and/or (c) a vector (e.g., a viral vector) comprising a binding agent-encoding polynucleotide.

As used herein, "pharmaceutically acceptable carrier" or "pharmaceutically acceptable excipient" includes any material which, when combined with an active ingredient, allows the ingredient to retain biological activity and is non-reactive with the subject's immune system and non-toxic to the subject when delivered. Examples include, but are not limited to, any of the standard pharmaceutical carriers such as a phosphate buffered saline solution, water, emulsions such as oil/water emulsion, and various types of wetting agents. Non-limiting examples of diluents for aerosol or parenteral administration are phosphate buffered saline, normal (0.9%) saline, Ringer's solution and dextrose solution. In some embodiments, the pH of the solution may be from about 5 to about 8, or from about 7 to about 7.5. In some embodiments, an excipient comprises one or more of sodium chloride, sodium phosphate, sodium citrate, citric acid, mannitol, sucrose, trehalose, polysorbate (e.g., polysorbate 20 or polysorbate 80), poloxamer (e.g., poloxamer 188), and an amino acid (e.g., glycine, L-histidine, or L-arginine). Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of antibody being administered. Compositions comprising such carriers are formulated by well-known conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000, each of which is incorporated herein by reference).

While any suitable carrier known to those of ordinary skill in the art may be employed in the pharmaceutical compositions of this disclosure, the type of carrier will vary depending on the mode of administration. Numerous delivery techniques for the pharmaceutical compositions of the disclosure (i.e., containing a binding agent or a binding agent-encoding polynucleotide) are well known in the art, such as those described by Rolland, 1998, Crit. Rev. Therap. Drug Carrier Systems 15:143-198, and references cited therein.

Compositions that include the binding agent and/or binding agent-encoding polynucleotide disclosed herein may be formulated for any appropriate manner of administration, including for example, systemic, topical, oral, nasal, intravenous, intracranial, intraperitoneal, subcutaneous or intramuscular administration, or by other methods, such as infusion, which ensure its delivery to the bloodstream in an effective form. The compositions may also be administered by isolated perfusion techniques, such as isolated tissue perfusion, to exert local therapeutic effects. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. In some embodiments, for oral administration, the formulation of the compositions is resistant to decomposition in the digestive tract, for example, as microcapsules encapsulating the binding agent (or binding agent-encoding polynucleotide or vector comprising such a polynucleotide) within liposomes. Biodegradable microspheres (e.g., polylactate polyglycolate) may also be employed as carriers for the pharmaceutical compositions of this disclosure. Suitable biodegradable microspheres are disclosed, for example, in U.S. Pat. Nos. 4,897,268 and 5,075,109.

The compositions may also comprise buffers (e.g., neutral buffered saline or phosphate buffered saline), carbohydrates (e.g., glucose, mannose, sucrose or dextran), mannitol, proteins, polypeptides or amino acids such as glycine, antioxidants, chelating agents such as EDTA or glutathione, adjuvants (e.g., aluminum hydroxide) and/or preservatives. Alternatively, the compositions may be formulated as a lyophilizate (e.g., for reconstitution prior to administration).

In some embodiments, the binding agent and/or binding agent-encoding polynucleotide also may be entrapped in microcapsules prepared, for example, by coacervation techniques or by interfacial polymerization (for example, hydroxymethylcellulose or gelatin-microcapsules and poly (methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000. To increase the serum half life of the binding agent (e.g., an antibody), one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, and IgG4) that is responsible for increasing the in vivo serum half-life of the IgG molecule.

The binding agents (and/or binding agent-encoding polynucleotides) disclosed herein may also be formulated as liposomes. Liposomes containing the binding agents (and/or binding agent-encoding polynucleotides) are prepared by methods known in the art, such as described in Epstein et al., 1985, Proc. Natl. Acad. Sci. USA 82:3688; Hwang et al., 1980, Proc. Natl Acad. Sci. USA 77:4030; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. In addition, where the binding agent is an antibody, antibodies (including antigen binding domain fragments such as Fab' fragments) can be conjugated to the liposomes as described in Martin et al., 1982, J. Biol. Chem. 257:286-288, via a disulfide interchange reaction. Administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding a polypeptide or antibody disclosed herein can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. (USA) (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides of the present disclosure can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Examples of viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Examples of naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0 524 968. Additional approaches are described in Philip, Mol. Cell Biol. (1994) 14:2411, and in Woffendin, Proc. Natl. Acad. Sci. (1994) 91:1581.

The compositions described herein can be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated.

The compositions of the disclosure include bulk drug compositions useful in the manufacture of non-pharmaceutical compositions (e.g., impure or non-sterile compositions) and pharmaceutical compositions (i.e., compositions that are suitable for administration to a subject or patient) that can be used in the preparation of unit dosage forms.

The compositions and methods disclosed herein can be used for treatment of patients having or at risk for a cancer, e.g., epithelial, colon, lung, breast, ovarian, or pancreatic cancer, or an epithelial adenocarcinoma.

The following examples are provided to illustrate, but not to limit, the invention.

EXAMPLES

Example 1. Isolation and Characterization of Anti-MUC1 Antibodies

Heavy and light chains of antibodies reactive against MUC1 were generated from plasma of individuals vaccinated with a 100 aa-long synthetic MUC1 peptide (100-mer) representing the unglycosylated tumor associated MUC1 antigen (Kimura et al., 2013, Cancer Prev. Res. (Phila.), 6:18-26). Binding of monoclonal antibodies produced by combinatorial pairing of chains was characterized by ELISA using the vaccine 100-mer peptide consisting of the following sequence (GVTSAPDTRPAPGSTAPPAH)$_5$ (SEQ ID NO: 2). Briefly, 96-well high-binding ELISA plates were coated with 50 µl of the peptide diluted in carbonate buffer at 2 µg/ml. The wells were washed then blocked with 5% fat-free milk in phosphate-buffered saline (PBS). Antibodies were diluted in 5% milk in PBS with 0.1% TWEEN 20 (PBS-T) and then added to the peptide-coated, blocked wells and incubated at 37° C. for 2 hours, after which the wells were washed. Binding of antibody was probed with an anti-human IgG goat antibody conjugated to horseradish peroxidase (HRP), and signal was detected with 3,3',5,5'-tetramethylbenzidine (TMB) substrate, which was neutralized with an acid, then the 450 nm absorbance was read. Twenty-three monoclonal antibodies (as a result of pairing 13 gamma chains [SEQ ID NOs: 3, 21, 37, 45, 64, 68, 78, 85, 90, 104, 107, 117, and 121] with 2 lambda [SEQ ID NOs: 182 and 188] and 10 kappa [SEQ ID NOs: 146, 160, 213, 223, 253, 259, 268, 273, 277, and 301] chains) showed significant peptide binding specificity by ELISA (Table 1). Additionally, the EC$_{50}$ of each antibody was approximated by ELISA titration (Table 1).

TABLE 1

Characterization of anti-MUC1 antibodies

| Antibody | VH | VL | ELISA EC$_{50}$ (ng/ml) |
|---|---|---|---|
| M1  | SEQ ID NO: 5   | SEQ ID NO: 148 | 11 |
| M2  | SEQ ID NO: 5   | SEQ ID NO: 162 | 7 |
| M3  | SEQ ID NO: 23  | SEQ ID NO: 184 | 11 |
| M4  | SEQ ID NO: 39  | SEQ ID NO: 190 | 4 |
| M5  | SEQ ID NO: 47  | SEQ ID NO: 215 | 100 |
| M6  | SEQ ID NO: 47  | SEQ ID NO: 225 | 12 |
| M7  | SEQ ID NO: 47  | SEQ ID NO: 255 | 11 |
| M8  | SEQ ID NO: 66  | SEQ ID NO: 261 | 4 |
| M9  | SEQ ID NO: 70  | SEQ ID NO: 270 | 4 |
| M10 | SEQ ID NO: 70  | SEQ ID NO: 279 | 4 |
| M11 | SEQ ID NO: 80  | SEQ ID NO: 261 | 10 |
| M12 | SEQ ID NO: 119 | SEQ ID NO: 270 | 2 |
| M13 | SEQ ID NO: 119 | SEQ ID NO: 279 | 2 |
| M14 | SEQ ID NO: 123 | SEQ ID NO: 261 | 2 |
| M15 | SEQ ID NO: 123 | SEQ ID NO: 270 | 5 |
| M16 | SEQ ID NO: 123 | SEQ ID NO: 275 | 11 |
| M17 | SEQ ID NO: 87  | SEQ ID NO: 261 | n.d. |
| M18 | SEQ ID NO: 87  | SEQ ID NO: 270 | n.d. |
| M19 | SEQ ID NO: 87  | SEQ ID NO: 279 | n.d. |
| M20 | SEQ ID NO: 92  | SEQ ID NO: 303 | 4 |
| M21 | SEQ ID NO: 106 | SEQ ID NO: 303 | 11 |
| M22 | SEQ ID NO: 109 | SEQ ID NO: 303 | 7 |
| M23 | SEQ ID NO: 119 | SEQ ID NO: 261 | n.d. |

This example demonstrates the generation of human antibodies reactive with MUC1.

Example 2. Characterization of Anti-MUC1 Antibodies

All ELISA-positive antibodies are tested for cell surface binding to ZR-75, T47D, and MCF-7, breast epithelial cancer cell lines that overexpress hypoglycosylated MUC1 at high levels. The antibodies are also tested for cell surface binding to MCF-10A, a nontransformed mammary epithelia cell line that expresses low levels of normal, fully glycosylated MUC1 and to LS-174T, a colon epithelial cell line with low to no expression of MUC1, as the negative control cell line. Cells are cultured in 384-well plates with their respective media types overnight. The medium is removed, and supernatant with antibody is applied to the wells containing live cells and incubated at 37° C. for 1 hour. The mouse monoclonal antibody HMFG1 is used as a positive control for surface binding (Arklie et al., 1981, Int. J. Cancer, 28:23-29). The antibody is aspirated, then the cells are fixed with formaldehyde, washed with PBS-T (0.1% TWEEN 20), and blocked with 5% goat serum and 0.3% TRITON-X100 in PBS. FITC-conjugated anti-human IgG goat antibody is used for detection of bound antibody. Antibodies are identified that show cell surface binding in ZR-75, T47D, and MCF-7 cells and moderate binding in MCF-10A cells, but do not stain or only minimally stain LS-174T cells.

The antibodies were further characterized for their surface binding to MUC1-expressing human cancer cell lines HPAF (pancreatic), MCF-7 (breast), BT-20 (breast), PANC-1 (pancreatic), and MS (breast) cell lines that express very low levels of MUC1 and was transfected with MUC1 cDNA (MS+MUC1). MCF-10A, a human nontransformed mammary epithelial cell line that expresses normal MUC1, was used as a predicted negative control for tumor MUC1 (hypoglycosylated MUC1)-specific staining Cells were grown attached to tissue culture plates, trypsinized, washed with PBS and 1% FBS and stained with each antibody for 30 minutes on ice. Cells were then washed 2 times with PBS and 1% FBS and stained with appropriate allophycocyanin (APC)-labeled secondary antibodies. Cells were washed again 2 times with PBS and 1% FBS and then analyzed by flow cytometry. Thirty-thousand events were collected for each sample and gated for viability by forward and side scatter. Live cells were then gated for APC+ staining as compared to an appropriate secondary antibody only control. The percentage of APC+ stained cells are listed for each cell line and antibody in Table 2. Several antibodies showed staining of the MUC1+ cancer cell lines and very low levels of staining of the MCF-10A normal cells.

This example demonstrates cell surface binding capacity and cancer specificity of the anti-MUC1 antibodies disclosed herein.

Example 3. Antibody Specificity

This example shows characterization of specific epitope recognition by each antibody on the 100 me vaccine peptide. Selected antibodies from Table 1 were further characterized for binding to synthetic MUC1 glycopeptides that were synthesized with the GalNac or GaNac-Gal carbohydrates on various serines and threonines along the MUC1 tandem repeat. If placed within the specific epitope recognized by an antibody, the antibody would not bind that particular glycopeptide. Synthetic peptides (GVTSAPDTRPAPG-STAPPAH)$_2$ (SEQ ID NO: 345), HGVTSAPDTRPAPG-STAPP (SEQ ID NO: 346), and SEQ ID NO: 346 with Thomsen-Friedenreich antigen (TF-antigen) (Galβ1-3Gal-NAc-Ser/Thr) or Tn-antigen (GaNAcα-Ser/Thr) glycosylation at residues Thr4, Ser5, Thr9, and/or Thr16, and BSA were coated onto a microplate, and the indicated antibodies were added to the plate at 0.01 mg/ml and detected using appropriate secondary antibodies with absorbance at 450 nm. Antibodies VU-3C6 (Abcam) and VU-4H5 (Abnova) were used as controls for MUC1 binding. VU-3C6 binding is not affected by glycosylation and is expected to bind to all glycopeptides. VU-3C6 is also not a tumor MUC1-specific antibody, as it stains MUC1 on normal cells as well as tumor cells. VU-4H5 is a tumor-specific antibody recognizing the epitope containing the sequence PDTRP (SEQ ID NO: 347) and glycosylation within or near that sequence would be expected to prevent its binding to the glycopeptides. Average ELISA absorbances of three experiments are indicated in Table 3. Antibodies M8, M14, M18, and M23 showed identical glycospecificity as the mouse antibody VU-4H5, as binding was blocked by TF glycosylation at Thr9 but not at Thr4, Ser5, or Thr16.

This example demonstrates specificity of these antibodies for different epitopes, including the previously defined tumor-specific MUC1 epitope (e.g., a hypoglycosylated MUC1 epitope) recognized by 4H5.

TABLE 2

Binding of anti-MUC1 antibodies to MUC1+ cell lines[1]

| Cell line | M1 | M2 | M3 | M7 | M16 | M20 | M21 | M22 | M8 | M14 | M18 | M23 | Hu-2nd. | 3C6[2] | 4H5[3] | M-2nd. |
|---|---|---|---|---|---|---|---|---|---|---|---|---|---|---|---|---|
| HPAF | 44.3 | 39.7 | 42.1 | 51.5 | 5.93 | 4.36 | 2.6 | 2.99 | 21.8 | 6.81 | 6.75 | 5.71 | 1.02 | 98.4 | 6.99 | 0.77 |
| MCF-7 | 43.8 | 45 | 79.6 | 83.5 | 18.3 | 29.2 | 5 | 5.68 | 34.2 | 20.8 | 21.7 | 16.1 | 1.73 | 98.7 | 27.8 | 1.39 |
| BT20 | 13.9 | 36 | 14.8 | 12.2 | 5.17 | 9.86 | 4.06 | 3.39 | 37.3 | 22.9 | 30.5 | 23 | 1.17 | 92.3 | 32.9 | 1.74 |
| SKBR-3 | 8.79 | 8.65 | 5.71 | 1.65 | 2.68 | 1.91 | 0.99 | 1.34 | 20.9 | 22.3 | 27.6 | 18.6 | 0.96 | 99.9 | 24.1 | 1.67 |
| PANC-1 | 3.1 | 16.7 | 1.55 | 0.41 | 0.76 | 0.39 | 0.75 | 0.7 | 2.08 | 55.2 | 61.2 | 45.1 | 2.01 | 98.8 | 54.3 | 3.45 |
| MS + MUC1 | 29.7 | 19.7 | 22 | 22.4 | 7.03 | 6.32 | 4.41 | 5.78 | 30.9 | 28.4 | 26.9 | 33.8 | 0.55 | 99.4 | 24.6 | 0.46 |
| MCF10a | 1.05 | 0.94 | 3.14 | 0.95 | 4.65 | 4.45 | 2.67 | 2.17 | 2.26 | 1.85 | 1.58 | 3.29 | 0.25 | 99.2 | 3.85 | 0.6 |

[1]Results are expressed as Mean Fluorescence Intensity (MFI). The higher the number, the higher level of abnormal (e.g., hypoglycosylated) MUC1 expression.
[2]Mouse anti-MUC1 antibody that binds to all forms of MUC1.
[3]Mouse anti-MUC1 antibody that binds only to abnormal (tumor) (e.g., hypoglycosylated) forms of MUC1.

TABLE 3

Binding of anti-MUC1 antibodies to synthetic glycopeptides

| Peptide | M1 | M2 | M3 | M7 | M16 | M20 | M21 | M22 | M8 | M14 | M18 | M23 | 3C6 | 4H5 |
|---|---|---|---|---|---|---|---|---|---|---|---|---|---|---|
| 345 | 3.2 | 3.4 | 3.1 | 3.5 | 3.3 | 2.8 | 3.0 | 3.1 | 3.0 | 2.9 | 3.3 | 2.9 | 2.3 | 2.5 |
| 346 | 0.1 | 0.1 | 0.1 | 0.1 | 2.2 | 1.9 | 2.1 | 2.1 | 2.1 | 2.1 | 2.4 | 2.0 | 1.5 | 1.9 |
| $T4^{TF}$ | 0.1 | 0.1 | 0.1 | 0.1 | 0.1 | 2.0 | 2.1 | 2.2 | 1.6 | 1.6 | 1.5 | 1.7 | 2.0 | 1.8 |
| $S5^{TF}$ | 0.1 | 0.1 | 0.1 | 0.1 | 1.3 | 2.1 | 2.1 | 2.2 | 2.1 | 2.1 | 2.7 | 2.4 | 2.0 | 1.8 |
| $T9^{TF}$ | 0.1 | 0.1 | 0.1 | 0.1 | 0.1 | 1.9 | 2.1 | 2.3 | 0.1 | 0.1 | 0.1 | 0.2 | 2.4 | 0.1 |
| $T16^{TF}$ | 0.1 | 0.1 | 0.1 | 0.1 | 2.2 | 0.1 | 0.1 | 0.1 | 2.5 | 2.4 | 2.5 | 2.5 | 1.5 | 1.9 |
| $T4^{TF}/T9^{TF}$ | 0.1 | 0.1 | 0.1 | 0.1 | 0.1 | 1.9 | 2.2 | 2.3 | 0.1 | 0.1 | 0.1 | 0.1 | 2.4 | 0.1 |
| $T4^{Tn}/T9^{Tn}/T16^{Tn}$ | 0.1 | 0.1 | 0.1 | 0.1 | 0.1 | 0.1 | 0.1 | 0.1 | 0.1 | 0.1 | 0.1 | 0.2 | 2.4 | 0.1 |
| BSA | 0.1 | 0.1 | 0.1 | 0.1 | 0.1 | 0.1 | 0.1 | 0.1 | 0.1 | 0.1 | 0.1 | 0.1 | 0.2 | 0.1 |

Example 4. Antibody Internalization

Internalization of the antibodies was measured using immunofluorescence. Briefly, MS-MUC1 cells were stained with 10 ug/ml of antibody or isotype control (a) for one hour at 4° C. or (b) for one hour at 4° C. followed by a wash and one hour at 37° C. Following staining, the cells are fixed and permeabilized, and antibody is detected using a fluorescent secondary antibody. Antibodies M1, M8, M14, M16, M17, M18, and M23 were tested and stained the cells using protocol (a), indicating that all bound to the cells. Antibodies M1, M8, M17, and M23 retained staining using protocol (b), indicating that these antibodies were internalized.

This example demonstrates internalization activity of anti-MUC1 antibodies disclosed herein.

Example 5. Staining of Human Tumor Samples

To determine if these antibodies recognize MUC1 on human tumors, colon tumor tissue microarrays were obtained from Biochain Institute, Inc. and stained using the two control mouse antibodies HMPV (BD Biosciences) and VU-4H5 and human antibodies M8, M14, and M23 with appropriate secondary antibodies. Secondary antibodies alone were used as negative controls. Following staining, the microarrays were analyzed using CELLPROFILER cell image analysis software (Broad Institute). The colon microarrays contained 150 samples: 6 normal, 6 benign, and 138 malignant. Of these, 3 of 6 normal samples, 3 of 6 benign samples, and 114 of 138 malignant samples were MUC1+ by HMPV staining and negative for secondary antibody only control. Staining of these MUC1+ samples by the indicated antibodies is shown in Table 4.

TABLE 4

Immunohistochemistry of colon tumor samples

| Antibody | Normal | Benign | Malignant |
|---|---|---|---|
| HMPV[1] | 3/3 | 3/3 | 114/114 |
| 4H5 | 0/3 | 2/3 | 49/114 |
| M8 | 0/3 | 2/3 | 59/114 |
| M14 | 0/3 | 2/3 | 56/114 |
| M23 | 0/3 | 2/3 | 76/114 |

[1]Mouse anti-MUC1 antibody that binds to all forms of MUC1.

Mouse anti-MUC1 antibody that binds only to abnormal (tumor) (e.g., hypoglycosylated) forms of MUC1.

Similar experiments were performed using pancreatic tumor tissue microarrays and antibodies M1, M8, M14, M16, M18, and M23. Tumor-specific staining was observed for all antibodies tested. Representative results for antibodies M8 and M23 are shown in FIG. 1.

This example demonstrates human tumor-specific staining by anti-MUC1 antibodies disclosed herein.

Example 6. Chimeric Antigen Receptor Constructs (CAR)

Lentiviral CAR expression constructs (Table 5) are generated for each anti-MUC1 antibody using standard PCR and isothermal assembly cloning methods. The antibody heavy and light chains are fused together by a glycine-serine linker (GS-linker) to create single chain variable fragments (scFv) comprising the targeting component of the CAR. The CARS are expressed as a single coding region from the human EF1alpha promoter cloned into the EcoRI and BsRGI sites of pSICO-EF1, a derivative of pSICO (Addgene, Ventura et al., 2004, Proc. Natl. Acad. Sci. USA, 101:10380-85). The coding region includes the MUC1 scFV, linker domains, accessory T cell receptor signaling domains, and the TagBFP gene fused by the co-translational t2a cleavage peptide to monitor expression and will consist of the following parts directly fused in order: [Kozak-κLeader]-[VH]-[GS-linker]-[VL]-[IgG4linker]-[CD28TM, cyto]-[4-1BBcyto]-[CD3zeta]-[t2a]-[TagBFP]. Gene fragments for CAR components are purchased from Integrated DNA Technologies. Constructs are packaged into lentivirus using standard methods and transduced into human primary T cells for functional testing. Cells are assayed for CAR expression of TagBFP and staining with ALEXA FLUOR 488 labeled MUC1 100-mer peptide by flow cytometry. Cells are then tested for MUC1-induced T cell activation marker expression (CD69, CD154, and CD62L) and cytokine release (IL-2 and IFN-gamma) in co-incubation assays with MS+MUC1 or MS target cells. CAR T cells and target cells will be co-incubated for 24 hours at ratios of 1:1, 5:1, 10:1 and assayed by flow cytometry for (CD69, CD154, and CD62L). The supernatants are collected and analyzed by ELISA for IL-2 and IFN-gamma. The ability of the cells to perform specific lysis of MUC1+ cells is tested in co-incubation assays of CAR T cells with carboxyfluorescein succinimidyl ester (CFSE)-labeled MS+MUC1 cells and 5-(6)-(((4-chloromethyl)benzoyl)amino)tetramethylrhodamine (CMTMR)-labeled MS cells. The cells are analyzed by flow cytometry, and a decreased ratio of MS+MUC1 to MUC1 cells indicates specific lysis. The CAR T cells are tested for their ability to shrink tumors in vivo in a mouse model. MS+MUC1 or MS cells expressing firefly luciferase are injected into immunocompromised mice. After two weeks CAR-modified T cells are infused into the mice and tumor growth is monitored using bioluminescence imaging.

TABLE 5

DNA sequences of CAR components and expression construct

| DNA part | SEQ ID NO: |
|---|---|
| Kozak-κLeader | 348 |
| GS-linker | 349 |
| IgG4 linker | 350 |
| CD28-TM, cyto | 351 |
| 4-1BBcyto | 352 |
| CD3zeta | 353 |
| t2a | 354 |
| TagBFP | 355 |
| pSICO-EF1 | 356 |

Example 7. Antibody Chain Sequences

For each antibody chain, the full-length antibody chain (HC or LC), variable region nucleic acid sequence (Nuc), variable region (VH or VL), framework regions (FR1-FR4), and complementarity determining regions (CDR1-CDR3) are provided.

The sequences for heavy chain 1 are HC (SEQ ID NO: 3), Nuc (SEQ ID NO: 4), VH (SEQ ID NO: 5), FR1 (SEQ ID NO: 6), CDR1 (SEQ ID NO: 7), FR2 (SEQ ID NO: 8), CDR2 (SEQ ID NO: 9), FR3 (SEQ ID NO: 10), CDR3 (SEQ ID NO: 11), and FR4 (SEQ ID NO: 12).

The sequences for heavy chain 2 are HC (SEQ ID NO: 13), Nuc (SEQ ID NO: 14), VH (SEQ ID NO: 15), FR1 (SEQ ID NO: 6), CDR1 (SEQ ID NO: 16), FR2 (SEQ ID NO: 8), CDR2 (SEQ ID NO: 17), FR3 (SEQ ID NO: 18), CDR3 (SEQ ID NO: 19), and FR4 (SEQ ID NO: 20).

The sequences for heavy chain 3 are HC (SEQ ID NO: 21), Nuc (SEQ ID NO: 22), VH (SEQ ID NO: 23), FR1 (SEQ ID NO: 6), CDR1 (SEQ ID NO: 16), FR2 (SEQ ID NO: 8), CDR2 (SEQ ID NO: 24), FR3 (SEQ ID NO: 25), CDR3 (SEQ ID NO: 19), and FR4 (SEQ ID NO: 20).

The sequences for heavy chain 4 are HC (SEQ ID NO: 26), Nuc (SEQ ID NO: 27), VH (SEQ ID NO: 28), FR1 (SEQ ID NO: 6), CDR1 (SEQ ID NO: 29), FR2 (SEQ ID NO: 30), CDR2 (SEQ ID NO: 24), FR3 (SEQ ID NO: 25), CDR3 (SEQ ID NO: 19), and FR4 (SEQ ID NO: 20).

The sequences for heavy chain 5 are HC (SEQ ID NO: 31), Nuc (SEQ ID NO: 32), VH (SEQ ID NO: 33), FR1 (SEQ ID NO: 6), CDR1 (SEQ ID NO: 34), FR2 (SEQ ID NO: 35), CDR2 (SEQ ID NO: 17), FR3 (SEQ ID NO: 18), CDR3 (SEQ ID NO: 36), and FR4 (SEQ ID NO: 20).

The sequences for heavy chain 6 are HC (SEQ ID NO: 37), Nuc (SEQ ID NO: 38), VH (SEQ ID NO: 39), FR1 (SEQ ID NO: 6), CDR1 (SEQ ID NO: 16), FR2 (SEQ ID NO: 8), CDR2 (SEQ ID NO: 17), FR3 (SEQ ID NO: 18), CDR3 (SEQ ID NO: 36), and FR4 (SEQ ID NO: 20).

The sequences for heavy chain 7 are HC (SEQ ID NO: 40), Nuc (SEQ ID NO: 41), VH (SEQ ID NO: 42), FR1 (SEQ ID NO: 6), CDR1 (SEQ ID NO: 16), FR2 (SEQ ID NO: 8), CDR2 (SEQ ID NO: 43), FR3 (SEQ ID NO: 44), CDR3 (SEQ ID NO: 36), and FR4 (SEQ ID NO: 20).

The sequences for heavy chain 8 are HC (SEQ ID NO: 45), Nuc (SEQ ID NO: 46), VH (SEQ ID NO: 47), FR1 (SEQ ID NO: 48), CDR1 (SEQ ID NO: 49), FR2 (SEQ ID NO: 50), CDR2 (SEQ ID NO: 51), FR3 (SEQ ID NO: 52), CDR3 (SEQ ID NO: 53), and FR4 (SEQ ID NO: 54).

The sequences for heavy chain 9 are HC (SEQ ID NO: 55), Nuc (SEQ ID NO: 56), VH (SEQ ID NO: 57), FR1 (SEQ ID NO: 58), CDR1 (SEQ ID NO: 59), FR2 (SEQ ID NO: 60), CDR2 (SEQ ID NO: 61), FR3 (SEQ ID NO: 62), CDR3 (SEQ ID NO: 63), and FR4 (SEQ ID NO: 20).

The sequences for heavy chain 10 are HC (SEQ ID NO: 64), Nuc (SEQ ID NO: 65), VH (SEQ ID NO: 66), FR1 (SEQ ID NO: 58), CDR1 (SEQ ID NO: 59), FR2 (SEQ ID NO: 60), CDR2 (SEQ ID NO: 67), FR3 (SEQ ID NO: 62), CDR3 (SEQ ID NO: 63), and FR4 (SEQ ID NO: 20).

The sequences for heavy chain 11 are HC (SEQ ID NO: 68), Nuc (SEQ ID NO: 69), VH (SEQ ID NO: 70), FR1 (SEQ ID NO: 58), CDR1 (SEQ ID NO: 59), FR2 (SEQ ID NO: 60), CDR2 (SEQ ID NO: 61), FR3 (SEQ ID NO: 71), CDR3 (SEQ ID NO: 72), and FR4 (SEQ ID NO: 20).

The sequences for heavy chain 12 are HC (SEQ ID NO: 73), Nuc (SEQ ID NO: 74), VH (SEQ ID NO: 75), FR1 (SEQ ID NO: 58), CDR1 (SEQ ID NO: 59), FR2 (SEQ ID NO: 60), CDR2 (SEQ ID NO: 76), FR3 (SEQ ID NO: 71), CDR3 (SEQ ID NO: 77), and FR4 (SEQ ID NO: 20).

The sequences for heavy chain 13 are HC (SEQ ID NO: 78), Nuc (SEQ ID NO: 79), VH (SEQ ID NO: 80), FR1 (SEQ ID NO: 58), CDR1 (SEQ ID NO: 59), FR2 (SEQ ID NO: 60), CDR2 (SEQ ID NO: 61), FR3 (SEQ ID NO: 71), CDR3 (SEQ ID NO: 77), and FR4 (SEQ ID NO: 20).

The sequences for heavy chain 14 are HC (SEQ ID NO: 81), Nuc (SEQ ID NO: 82), VH (SEQ ID NO: 83), FR1 (SEQ ID NO: 58), CDR1 (SEQ ID NO: 59), FR2 (SEQ ID NO: 60), CDR2 (SEQ ID NO: 61), FR3 (SEQ ID NO: 71), CDR3 (SEQ ID NO: 84), and FR4 (SEQ ID NO: 20).

The sequences for heavy chain 15 are HC (SEQ ID NO: 85), Nuc (SEQ ID NO: 86), VH (SEQ ID NO: 87), FR1 (SEQ ID NO: 88), CDR1 (SEQ ID NO: 59), FR2 (SEQ ID NO: 60), CDR2 (SEQ ID NO: 61), FR3 (SEQ ID NO: 71), CDR3 (SEQ ID NO: 89), and FR4 (SEQ ID NO: 20).

The sequences for heavy chain 16 are HC (SEQ ID NO: 90), Nuc (SEQ ID NO: 91), VH (SEQ ID NO: 92), FR1 (SEQ ID NO: 93), CDR1 (SEQ ID NO: 94), FR2 (SEQ ID NO: 95), CDR2 (SEQ ID NO: 96), FR3 (SEQ ID NO: 97), CDR3 (SEQ ID NO: 98), and FR4 (SEQ ID NO: 12).

The sequences for heavy chain 17 are HC (SEQ ID NO: 99), Nuc (SEQ ID NO: 100), VH (SEQ ID NO: 101), FR1 (SEQ ID NO: 48), CDR1 (SEQ ID NO: 49), FR2 (SEQ ID NO: 50), CDR2 (SEQ ID NO: 51), FR3 (SEQ ID NO: 102), CDR3 (SEQ ID NO: 103), and FR4 (SEQ ID NO: 12).

The sequences for heavy chain 18 are HC (SEQ ID NO: 104), Nuc (SEQ ID NO: 105), VH (SEQ ID NO: 106), FR1 (SEQ ID NO: 48), CDR1 (SEQ ID NO: 49), FR2 (SEQ ID NO: 50), CDR2 (SEQ ID NO: 51), FR3 (SEQ ID NO: 52), CDR3 (SEQ ID NO: 103), and FR4 (SEQ ID NO: 12).

The sequences for heavy chain 19 are HC (SEQ ID NO: 107), Nuc (SEQ ID NO: 108), VH (SEQ ID NO: 109), FR1 (SEQ ID NO: 48), CDR1 (SEQ ID NO: 49), FR2 (SEQ ID NO: 50), CDR2 (SEQ ID NO: 110), FR3 (SEQ ID NO: 111), CDR3 (SEQ ID NO: 112), and FR4 (SEQ ID NO: 20).

The sequences for heavy chain 20 are HC (SEQ ID NO: 113), Nuc (SEQ ID NO: 114), VH (SEQ ID NO: 115), FR1 (SEQ ID NO: 58), CDR1 (SEQ ID NO: 59), FR2 (SEQ ID NO: 60), CDR2 (SEQ ID NO: 67), FR3 (SEQ ID NO: 62), CDR3 (SEQ ID NO: 116), and FR4 (SEQ ID NO: 20).

The sequences for heavy chain 21 are HC (SEQ ID NO: 117), Nuc (SEQ ID NO: 118), VH (SEQ ID NO: 119), FR1 (SEQ ID NO: 58), CDR1 (SEQ ID NO: 59), FR2 (SEQ ID NO: 60), CDR2 (SEQ ID NO: 61), FR3 (SEQ ID NO: 71), CDR3 (SEQ ID NO: 120), and FR4 (SEQ ID NO: 20).

The sequences for heavy chain 22 are HC (SEQ ID NO: 121), Nuc (SEQ ID NO: 122), VH (SEQ ID NO: 123), FR1 (SEQ ID NO: 58), CDR1 (SEQ ID NO: 59), FR2 (SEQ ID NO: 60), CDR2 (SEQ ID NO: 61), FR3 (SEQ ID NO: 71), CDR3 (SEQ ID NO: 124), and FR4 (SEQ ID NO: 20).

The sequences for heavy chain 23 are HC (SEQ ID NO: 125), Nuc (SEQ ID NO: 126), VH (SEQ ID NO: 127), FR1 (SEQ ID NO: 58), CDR1 (SEQ ID NO: 59), FR2 (SEQ ID NO: 60), CDR2 (SEQ ID NO: 67), FR3 (SEQ ID NO: 62), CDR3 (SEQ ID NO: 129), and FR4 (SEQ ID NO: 20).

The sequences for heavy chain 24 are HC (SEQ ID NO: 130), Nuc (SEQ ID NO: 131), VH (SEQ ID NO: 132), FR1 (SEQ ID NO: 58), CDR1 (SEQ ID NO: 59), FR2 (SEQ ID NO: 128), CDR2 (SEQ ID NO: 67), FR3 (SEQ ID NO: 62), CDR3 (SEQ ID NO: 129), and FR4 (SEQ ID NO: 20).

The sequences for heavy chain 25 are HC (SEQ ID NO: 139), Nuc (SEQ ID NO: 140), VH (SEQ ID NO: 141), FR1 (SEQ ID NO: 58), CD1 (SEQ ID NO: 59), FR2 (SEQ ID NO: 60), CDR2 (SEQ ID NO: 61), FR3 (SEQ ID NO: 142), CDR3 (SEQ ID NO: 124), and FR4 (SEQ ID NO: 20).

The sequences for heavy chain 26 are HC (SEQ ID NO: 143), Nuc (SEQ ID NO: 144), VH (SEQ ID NO: 145), FR1 (SEQ ID NO: 58), CDR1 (SEQ ID NO: 59), FR2 (SEQ ID NO: 60), CDR2 (SEQ ID NO: 61), FR3 (SEQ ID NO: 142), CDR3 (SEQ ID NO: 124), and FR4 (SEQ ID NO: 20).

The sequences for light chain 1 are LC (SEQ ID NO: 146), Nuc (SEQ ID NO: 147), VL (SEQ ID NO: 148), FR1 (SEQ ID NO: 149), CDR1 (SEQ ID NO: 150), FR2 (SEQ ID NO: 151), CDR2 (SEQ ID NO: 152), FR3 (SEQ ID NO: 153), CDR3 (SEQ ID NO: 154), and FR4 (SEQ ID NO: 155).

The sequences for light chain 2 are LC (SEQ ID NO: 156), Nuc (SEQ ID NO: 157), VL (SEQ ID NO: 158), FR1 (SEQ ID NO: 149), CDR1 (SEQ ID NO: 159), FR2 (SEQ ID NO: 151), CDR2 (SEQ ID NO: 152), FR3 (SEQ ID NO: 153), CDR3 (SEQ ID NO: 154), and FR4 (SEQ ID NO: 155).

The sequences for light chain 3 are LC (SEQ ID NO: 160), Nuc (SEQ ID NO: 161), VL (SEQ ID NO: 162), FR1 (SEQ ID NO: 149), CDR1 (SEQ ID NO: 150), FR2 (SEQ ID NO: 151), CDR2 (SEQ ID NO: 152), FR3 (SEQ ID NO: 153), CDR3 (SEQ ID NO: 163), and FR4 (SEQ ID NO: 164).

The sequences for light chain 4 are LC (SEQ ID NO: 165), Nuc (SEQ ID NO: 166), VL (SEQ ID NO: 167), FR1 (SEQ ID NO: 149), CDR1 (SEQ ID NO: 150), FR2 (SEQ ID NO: 151), CDR2 (SEQ ID NO: 152), FR3 (SEQ ID NO: 153), CDR3 (SEQ ID NO: 163), and FR4 (SEQ ID NO: 164).

The sequences for light chain 5 are LC (SEQ ID NO: 168), Nuc (SEQ ID NO: 169), VL (SEQ ID NO: 170), FR1 (SEQ ID NO: 149), CDR1 (SEQ ID NO: 150), FR2 (SEQ ID NO: 151), CDR2 (SEQ ID NO: 152), FR3 (SEQ ID NO: 171), CDR3 (SEQ ID NO: 163), and FR4 (SEQ ID NO: 164).

The sequences for light chain 6 are LC (SEQ ID NO: 172), Nuc (SEQ ID NO: 173), VL (SEQ ID NO: 174), FR1 (SEQ ID NO: 175), CDR1 (SEQ ID NO: 176), FR2 (SEQ ID NO: 177), CDR2 (SEQ ID NO: 178), FR3 (SEQ ID NO: 179), CDR3 (SEQ ID NO: 180), and FR4 (SEQ ID NO: 181).

The sequences for light chain 7 are LC (SEQ ID NO: 182), Nuc (SEQ ID NO: 183), VL (SEQ ID NO: 184), FR1 (SEQ ID NO: 175), CDR1 (SEQ ID NO: 185), FR2 (SEQ ID NO: 186), CDR2 (SEQ ID NO: 187), FR3 (SEQ ID NO: 179), CDR3 (SEQ ID NO: 180), and FR4 (SEQ ID NO: 181).

The sequences for light chain 8 are LC (SEQ ID NO: 188), Nuc (SEQ ID NO: 189), VL (SEQ ID NO: 190), FR1 (SEQ ID NO: 136), CDR1 (SEQ ID NO: 185), FR2 (SEQ ID NO: 137), CDR2 (SEQ ID NO: 138), FR3 (SEQ ID NO: 179), CDR3 (SEQ ID NO: 180), and FR4 (SEQ ID NO: 181).

The sequences for light chain 9 are LC (SEQ ID NO: 191), Nuc (SEQ ID NO: 192), VL (SEQ ID NO: 193), FR1 (SEQ ID NO: 194), CDR1 (SEQ ID NO: 195), FR2 (SEQ ID NO: 196), CDR2 (SEQ ID NO: 197), FR3 (SEQ ID NO: 198), CDR3 (SEQ ID NO: 199), and FR4 (SEQ ID NO: 200).

The sequences for light chain 10 are LC (SEQ ID NO: 201), Nuc (SEQ ID NO: 202), VL (SEQ ID NO: 203), FR1 (SEQ ID NO: 194), CDR1 (SEQ ID NO: 204), FR2 (SEQ ID NO: 196), CDR2 (SEQ ID NO: 205), FR3 (SEQ ID NO: 198), CDR3 (SEQ ID NO: 199), and FR4 (SEQ ID NO: 200).

The sequences for light chain 11 are LC (SEQ ID NO: 206), Nuc (SEQ ID NO: 207), VL (SEQ ID NO: 208), FR1 (SEQ ID NO: 194), CDR1 (SEQ ID NO: 195), FR2 (SEQ ID NO: 196), CDR2 (SEQ ID NO: 205), FR3 (SEQ ID NO: 198), CDR3 (SEQ ID NO: 199), and FR4 (SEQ ID NO: 200).

The sequences for light chain 12 are LC (SEQ ID NO: 209), Nuc (SEQ ID NO: 210), VL (SEQ ID NO: 211), FR1 (SEQ ID NO: 194), CDR1 (SEQ ID NO: 195), FR2 (SEQ ID NO: 196), CDR2 (SEQ ID NO: 205), FR3 (SEQ ID NO: 212), CDR3 (SEQ ID NO: 199), and FR4 (SEQ ID NO: 200).

The sequences for light chain 13 are LC (SEQ ID NO: 213), Nuc (SEQ ID NO: 214), VL (SEQ ID NO: 215), FR1 (SEQ ID NO: 194), CDR1 (SEQ ID NO: 216), FR2 (SEQ ID NO: 196), CDR2 (SEQ ID NO: 217), FR3 (SEQ ID NO: 198), CDR3 (SEQ ID NO: 199), and FR4 (SEQ ID NO: 200).

The sequences for light chain 14 are LC (SEQ ID NO: 218), Nuc (SEQ ID NO: 219), VL (SEQ ID NO: 220), FR1 (SEQ ID NO: 194), CDR1 (SEQ ID NO: 195), FR2 (SEQ ID NO: 196), CDR2 (SEQ ID NO: 205), FR3 (SEQ ID NO: 198), CDR3 (SEQ ID NO: 221), and FR4 (SEQ ID NO: 222).

The sequences for light chain 15 are LC (SEQ ID NO: 223), Nuc (SEQ ID NO: 224), VL (SEQ ID NO: 225), FR1 (SEQ ID NO: 194), CDR1 (SEQ ID NO: 195), FR2 (SEQ ID NO: 196), CDR2 (SEQ ID NO: 205), FR3 (SEQ ID NO: 198), CDR3 (SEQ ID NO: 226), and FR4 (SEQ ID NO: 222).

The sequences for light chain 16 are LC (SEQ ID NO: 227), Nuc (SEQ ID NO: 228), VL (SEQ ID NO: 229), FR1 (SEQ ID NO: 194), CDR1 (SEQ ID NO: 230), FR2 (SEQ ID NO: 196), CDR2 (SEQ ID NO: 205), FR3 (SEQ ID NO: 231), CDR3 (SEQ ID NO: 226), and FR4 (SEQ ID NO: 222).

The sequences for light chain 17 are LC (SEQ ID NO: 232), Nuc (SEQ ID NO: 233), VL (SEQ ID NO: 234), FR (SEQ ID NO: 235), CDR1 (SEQ ID NO: 236), FR2 (SEQ ID NO: 237), CDR2 (SEQ ID NO: 238), FR3 (SEQ ID NO: 239), CDR3 (SEQ ID NO: 226), and FR4 (SEQ ID NO: 222).

The sequences for light chain 18 are LC (SEQ ID NO: 240), Nuc (SEQ ID NO: 241), VL (SEQ ID NO: 242), FR1 (SEQ ID NO: 194), CDR1 (SEQ ID NO: 195), FR2 (SEQ ID NO: 196), CDR2 (SEQ ID NO: 205), FR3 (SEQ ID NO: 198), CDR3 (SEQ ID NO: 226), and FR4 (SEQ ID NO: 243).

The sequences for light chain 19 are LC (SEQ ID NO: 244), Nuc (SEQ ID NO: 245), VL (SEQ ID NO: 246), FR1 (SEQ ID NO: 194), CDR1 (SEQ ID NO: 247), FR2 (SEQ ID NO: 196), CDR2 (SEQ ID NO: 205), FR3 (SEQ ID NO: 198), CDR3 (SEQ ID NO: 226), and FR4 (SEQ ID NO: 243).

The sequences for light chain 20 are LC (SEQ ID NO: 248), Nuc (SEQ ID NO: 249), VL (SEQ ID NO: 250), FR1 (SEQ ID NO: 194), CDR1 (SEQ ID NO: 251), FR2 (SEQ ID NO: 252), CDR2 (SEQ ID NO: 205), FR3 (SEQ ID NO: 198), CDR3 (SEQ ID NO: 226), and FR4 (SEQ ID NO: 243).

The sequences for light chain 21 are LC (SEQ ID NO: 253), Nuc (SEQ ID NO: 254), VL (SEQ ID NO: 255), FR1 (SEQ ID NO: 256), CDR1 (SEQ ID NO: 257), FR2 (SEQ ID NO: 252), CDR2 (SEQ ID NO: 238), FR3 (SEQ ID NO: 258), CDR3 (SEQ ID NO: 226), and FR4 (SEQ ID NO: 243).

The sequences for light chain 22 are LC (SEQ ID NO: 259), Nuc (SEQ ID NO: 260), VL (SEQ ID NO: 261), FR1 (SEQ ID NO: 262), CDR1 (SEQ ID NO: 263), FR2 (SEQ ID NO: 264), CDR2 (SEQ ID NO: 265), FR3 (SEQ ID NO: 266), CDR3 (SEQ ID NO: 267), and FR4 (SEQ ID NO: 200).

The sequences for light chain 23 are LC (SEQ ID NO: 268), Nuc (SEQ ID NO: 269), VL (SEQ ID NO: 270), FR1 (SEQ ID NO: 262), CDR1 (SEQ ID NO: 263), FR2 (SEQ ID NO: 264), CDR2 (SEQ ID NO: 265), FR3 (SEQ ID NO: 266), CDR3 (SEQ ID NO: 271), and FR4 (SEQ ID NO: 272).

The sequences for light chain 24 are LC (SEQ ID NO: 273), Nuc (SEQ ID NO: 274), VL (SEQ ID NO: 275), FR1 (SEQ ID NO: 262), CDR1 (SEQ ID NO: 263), FR2 (SEQ ID NO: 264), CDR2 (SEQ ID NO: 265), FR3 (SEQ ID NO: 266), CDR3 (SEQ ID NO: 276), and FR4 (SEQ ID NO: 200).

The sequences for light chain 25 are LC (SEQ ID NO: 277), Nuc (SEQ ID NO: 278), VL (SEQ ID NO: 279), FR1 (SEQ ID NO: 262), CDR1 (SEQ ID NO: 263), FR2 (SEQ ID NO: 264), CDR2 (SEQ ID NO: 265), FR3 (SEQ ID NO: 280), CDR3 (SEQ ID NO: 276), and FR4 (SEQ ID NO: 200).

The sequences for light chain 26 are LC (SEQ ID NO: 281), Nuc (SEQ ID NO: 282), VL (SEQ ID NO: 283), FR1 (SEQ ID NO: 284), CDR1 (SEQ ID NO: 285), FR2 (SEQ ID NO: 286), CDR2 (SEQ ID NO: 287), FR3 (SEQ ID NO: 198), CDR3 (SEQ ID NO: 288), and FR4 (SEQ ID NO: 222).

The sequences for light chain 27 are LC (SEQ ID NO: 289), Nuc (SEQ ID NO: 290), VL (SEQ ID NO: 291), FR1 (SEQ ID NO: 284), CDR1 (SEQ ID NO: 292), FR2 (SEQ ID NO: 286), CDR2 (SEQ ID NO: 293), FR3 (SEQ ID NO: 294), CDR3 (SEQ ID NO: 288), and FR4 (SEQ ID NO: 222).

The sequences for light chain 28 are LC (SEQ ID NO: 295), Nuc (SEQ ID NO: 296), VL (SEQ ID NO: 297), FR1 (SEQ ID NO: 298), CDR1 (SEQ ID NO: 299), FR2 (SEQ ID NO: 196), CDR2 (SEQ ID NO: 205), FR3 (SEQ ID NO: 300), CDR3 (SEQ ID NO: 288), and FR4 (SEQ ID NO: 222).

The sequences for light chain 29 are LC (SEQ ID NO: 301), Nuc (SEQ ID NO: 302), VL (SEQ ID NO: 303), FR1 (SEQ ID NO: 284), CDR1 (SEQ ID NO:285), FR2 (SEQ ID NO:286), CDR2 (SEQ ID NO: 304), FR3 (SEQ ID NO: 305), CDR3 (SEQ ID NO: 288), and FR4 (SEQ ID NO: 222).

The sequences for light chain 30 are LC (SEQ ID NO: 306), Nuc (SEQ ID NO: 307), VL (SEQ ID NO: 308), FR1 (SEQ ID NO: 309), CDR1 (SEQ ID NO: 310), FR2 (SEQ ID NO: 196), CDR2 (SEQ ID NO: 311), FR3 (SEQ ID NO: 312), CDR3 (SEQ ID NO: 267), and FR4 (SEQ ID NO: 272).

The sequences for light chain 31 are LC (SEQ ID NO: 313), Nuc (SEQ ID NO: 314), VL (SEQ ID NO: 315), FR1 (SEQ ID NO: 262), CDR1 (SEQ ID NO: 263), FR2 (SEQ ID NO: 264), CDR2 (SEQ ID NO: 265), FR3 (SEQ ID NO: 266), CDR3 (SEQ ID NO: 316), and FR4 (SEQ ID NO: 222).

The sequences for light chain 32 are LC (SEQ ID NO: 317), Nuc (SEQ ID NO: 318), VL (SEQ ID NO: 319), FR1 (SEQ ID NO: 262), CDR1 (SEQ ID NO: 263), FR2 (SEQ ID NO: 264), CDR2 (SEQ ID NO: 265), FR3 (SEQ ID NO: 266), CDR3 (SEQ ID NO: 320), and FR4 (SEQ ID NO: 243).

The sequences for light chain 33 are LC (SEQ ID NO: 321), Nuc (SEQ ID NO: 322), VL (SEQ ID NO: 323), FR1 (SEQ ID NO: 324), CDR1 (SEQ ID NO: 263), FR2 (SEQ ID NO: 264), CDR2 (SEQ ID NO: 265), FR3 (SEQ ID NO: 266), CDR3 (SEQ ID NO: 325), and FR4 (SEQ ID NO: 200).

The sequences for light chain 34 are LC (SEQ ID NO: 326), Nuc (SEQ ID NO: 327), VL (SEQ ID NO: 328), FR1 (SEQ ID NO: 262), CDR1 (SEQ ID NO: 263), FR2 (SEQ ID NO: 264), CDR2 (SEQ ID NO: 265), FR3 (SEQ ID NO: 266), CDR3 (SEQ ID NO: 329), and FR4 (SEQ ID NO: 330).

The sequences for light chain 35 are LC (SEQ ID NO: 331), Nuc (SEQ ID NO: 332), VL (SEQ ID NO: 333), FR1 (SEQ ID NO: 334), CDR1 (SEQ ID NO: 335), FR2 (SEQ ID NO: 264), CDR2 (SEQ ID NO: 265), FR3 (SEQ ID NO: 336), CDR3 (SEQ ID NO: 337), and FR4 (SEQ ID NO: 200).

The sequences for light chain 36 are LC (SEQ ID NO: 338), Nuc (SEQ ID NO: 339), VL (SEQ ID NO: 340), FR1 (SEQ ID NO: 262), CDR1 (SEQ ID NO: 263), FR2 (SEQ ID NO: 264), CDR2 (SEQ ID NO: 265), FR3 (SEQ ID NO: 341), CDR3 (SEQ ID NO: 342), and FR4 (SEQ ID NO: 243).

In some embodiments, a binding agent disclosed herein has:
(a) a heavy chain variable region having CDRs 1, 2, and 3 that include a set of amino acid sequences set forth in
  (i) DYYMS (SEQ ID NO: 59), YISSSG(T/S)T(K/I)YYADSVKG (SEQ ID NO: 357), and E(N/R)(L/I)GYCSGGSCYYYYMDV (SEQ ID NO: 358), respectively;
  (ii) DYYMS (SEQ ID NO: 59), YISSSG(T/S)T(K/I)YYADSVKG (SEQ ID NO: 357), and E(N/R)(L/I)GYCTGGNCFYYYYMDV (SEQ ID NO: 359), respectively;
  (iii) DYYMS (SEQ ID NO: 59), YISSSG(T/S)T(K/I)YYADSVKG (SEQ ID NO: 357), and E(N/R)(L/I)GYC(T/S)GG(N/S)C(F/Y)YYYYMDV (SEQ ID NO: 360), respectively;
  (iv) DYYMS (SEQ ID NO: 59), YISSSG(T/S)T(K/I)YYADSVKG (SEQ ID NO: 357), and E(D/N)(I/L)GYCSGGSCFYYYYMDV (SEQ ID NO: 361), respectively; or
  (v) DYYMS (SEQ ID NO: 59), YISSSG(T/S)T(K/I)YYADSVKG (SEQ ID NO: 357), and E(D/N/R)(L/I)GYC(T/S)GG(N/S)C(F/Y)YYYYMDV (SEQ ID NO: 362), respectively, and
(b) a light chain variable region having CDRs 1, 2, and 3 that include a set of amino acid sequences set forth in
  (i) RSSQSLVHSDGNTYLS (SEQ ID NO: 263), KISNRFS (SEQ ID NO: 265), and (M/L)QATQFP(L/I/F/V)T (SEQ ID NO: 363), respectively;

(ii) RSSQSLV(H/R)SDGNTYLS (SEQ ID NO: 364), KISNRFS (SEQ ID NO: 265), and (M/L)Q(A/G)TQFP(L/I/F/V)T (SEQ ID NO: 365), respectively; or (iii) RSSQSL(V/L)(H/R)S(D/N)G(Y/N)TYL(S/H) (SEQ ID NO: 366), (K/R)(I/V)SN(R/H)(F/L)S (SEQ ID NO: 367), and (M/L)Q(A/G)(T/S)QFP(L/I/F/V)T (SEQ ID NO: 368), respectively.

In some embodiments, a binding agent disclosed herein has:

(a) a heavy chain variable region having CDRs 1, 2, and 3 that include the amino acid sequences set forth in SEQ ID NOs: 7, 9, and 11, respectively, and (b) a light chain variable region having CDRs 1, 2, and 3 that include a set of amino acid sequences set forth in (i) (K/R)SSQ(S/N)(V/L)LY(S/N)SN(N/K)(K/L)NYL(A/S) (SEQ ID NO: 369), WASTRES (SEQ ID NO: 152), and QQYYNTPFT (SEQ ID NO: 154), respectively; or (ii) (K/R)SSQ(S/N)(V/L)LY(S/N)SN(N/K)(K/L)NYL(A/S) (SEQ ID NO: 369), WASTRES (SEQ ID NO: 152), and QQYY(S/N)TPFT (SEQ ID NO: 370), respectively.

Examples of constant region coding sequences are provided below. These sequences can be used to prepare antibody coding sequences without naturally-occurring introns.

An example of a heavy chain constant region coding sequence is SEQ ID NO: 133. An example of a kappa chain constant region coding sequence is SEQ ID NO: 134. An example of a lambda chain constant region coding sequence is SEQ ID NO: 135.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified anti-MUC1 binding agent comprising:
(a) a heavy chain variable region having complementarity determining regions (CDRs) 1, 2, and 3 comprising the amino acid sequences of DYYMS (SEQ ID NO: 59), YISSSG(S/T)T(I/K)YYADSVKG (SEQ ID NO: 357), and E(R/N)(I/L)GYC(S/T)GG(S/N) C(Y/F)YYYYMDV (SEQ ID NO: 360), respectively; and a light chain variable region having CDRs 1, 2, 3, comprising the amino acid sequences of RSSQSL(V/L)(H/R)S(D/N)G(N/Y)TYL(S/H) (SEQ ID NO: 366), (K/R)(I/V)SN(R/H)(F/L)S (SEQ ID NO: 367), and (M/L)Q(A/G)(T/S)QFP(L/I/F/V)T (SEQ ID NO: 368), respectively;
(b) a heavy chain variable region having CDRs 1, 2, and 3 comprising the amino acid sequences set forth in SEQ ID NOs: 7, 9, and 11, respectively; and a light chain variable region having CDRs 1, 2, and 3 comprising a set of amino acid sequences set forth in
(i) SEQ ID NOs: 150, 152, and 154, respectively;
(ii) SEQ ID NOs: 159, 152, and 154, respectively; or
(iii) SEQ ID NOs: 150, 152, and 163, respectively;
(c) a heavy chain variable region having CDRs 1, 2, and 3 comprising a set of amino acid sequences set forth in
(i) SEQ ID NOs: 16, 17, and 19, respectively;
(ii) SEQ ID NOs: 16, 24, and 19, respectively;
(iii) SEQ ID NOs: 29, 24, and 19, respectively;
(iv) SEQ ID NOs: 34, 17, and 36, respectively;
(v) SEQ ID NOs: 16, 17, and 36, respectively; or
(vi) SEQ ID NOs: 16, 43, and 36, respectively; and
a light chain variable region having CDRs 1, 2, and 3 comprising a set of amino acid sequences set forth in
(i) SEQ ID NOs: 176, 178, and 180, respectively;
(ii) SEQ ID NOs: 185, 187, and 180, respectively; or
(iii) SEQ ID NOs: 185, 138, and 180, respectively;
(d) a heavy chain variable region having CDRs 1, 2, and 3 comprising the amino acid sequences set forth in SEQ ID NOs: 49, 51, and 53, respectively; and a light chain variable region having CDRs 1, 2, and 3 comprising a set of amino acid sequences set forth in
(i) SEQ ID NOs: 195, 197, and 199, respectively;
(ii) SEQ ID NOs: 204, 205, and 199, respectively;
(iii) SEQ ID NOs: 195, 205, and 199, respectively;
(iv) SEQ ID NOs: 216, 217, and 199, respectively;
(v) SEQ ID NOs: 195, 205, and 221, respectively;
(vi) SEQ ID NOs: 195, 205, and 226, respectively;
(vii) SEQ ID NOs: 230, 205, and 226, respectively;
(viii) SEQ ID NOs: 236, 238, and 226, respectively;
(ix) SEQ ID NOs: 247, 205, and 226, respectively;
(x) SEQ ID NOs: 251, 205, and 226, respectively; or
(xi) SEQ ID NOs: 257, 238, and 226, respectively;
(e) a heavy chain variable region having CDRs 1, 2, and 3 comprising a set of amino acid sequences set forth in
(i) SEQ ID NOs: 59, 61, and 63, respectively;
(ii) SEQ ID NOs: 59, 67, and 63, respectively;
(iii) SEQ ID NOs: 59, 61, and 72, respectively;
(iv) SEQ ID NOs: 59, 76, and 77, respectively;
(v) SEQ ID NOs: 59, 61, and 77, respectively;
(vi) SEQ ID NOs: 59, 67, and 116, respectively;
(vii) SEQ ID NOs: 59, 61, and 120, respectively;
(viii) SEQ ID NOs: 59, 61, and 84, respectively;
(ix) SEQ ID NOs: 59, 61, and 124, respectively;
(x) SEQ ID NOs: 59, 67, and 129, respectively; or
(xi) SEQ ID NOs: 59, 61, and 89, respectively; and
a light chain variable region having CDRs 1, 2, and 3 comprising a set of amino acid sequences set forth in
(i) SEQ ID NOs: 263, 265, and 267, respectively;
(ii) SEQ ID NOs: 310, 311, and 267, respectively;
(iii) SEQ ID NOs: 263, 265, and 316, respectively;
(iv) SEQ ID NOs: 263, 265, and 320, respectively;
(v) SEQ ID NOs: 263, 265, and 325, respectively;
(vi) SEQ ID NOs: 263, 265, and 329, respectively;
(vii) SEQ ID NOs: 335, 265, and 337, respectively;
(viii) SEQ ID NOs: 263, 265, and 342, respectively;
(ix) SEQ ID NOs: 263, 265, and 271, respectively; or
(x) SEQ ID NOs: 263, 265, and 276, respectively;
(f) a heavy chain variable region having CDRs 1, 2, and 3 comprising a set of amino acid sequences set forth in
(i) SEQ ID NOs: 94, 96, and 98, respectively;
(ii) SEQ ID NOs: 49, 51, and 103, respectively; or
(iii) SEQ ID NOs: 49, 110, and 112, respectively; and
a light chain variable region having CDRs 1, 2, and 3 comprising a set of amino acid sequences set forth in
(i) SEQ ID NOs: 263, 265, and 267, respectively;
(ii) SEQ ID NOs: 310, 311, and 267, respectively;
(iii) SEQ ID NOs: 263, 265, and 271, respectively; or
(iv) SEQ ID NOs: 263, 265, and 276, respectively;
(g) a heavy chain variable region having CDRs 1, 2, and 3 comprising the amino acid sequences set forth in SEQ ID NOs: 7, 9, and 11, respectively; and a light chain variable region having CDRs 1, 2, and 3 comprising the amino acid sequences set forth in SEQ ID NOs: 150, 152, and 163, respectively;
(h) a heavy chain variable region having CDRs 1, 2, and 3 comprising a set of amino acid sequences set forth in
(i) SEQ ID NOs: 59, 61, and 63, respectively;
(ii) SEQ ID NOs: 59, 67, and 63, respectively;
(iii) SEQ ID NOs: 59, 61, and 72, respectively;
(iv) SEQ ID NOs: 59, 76, and 77, respectively;
(v) SEQ ID NOs: 59, 61, and 77, respectively;
(vi) SEQ ID NOs: 59, 67, and 116, respectively;
(vii) SEQ ID NOs: 59, 61, and 120, respectively;
(viii) SEQ ID NOs: 59, 61, and 84, respectively;
(ix) SEQ ID NOs: 59, 61, and 124, respectively;
(x) SEQ ID NOs: 59, 67, and 129, respectively; or
(xi) SEQ ID NOs: 59, 61, and 89, respectively; and
a light chain variable region having CDRs 1, 2, and 3 comprising a set of amino acid sequences set forth in
(i) SEQ ID NOs: 263, 265, and 267, respectively;
(ii) SEQ ID NOs: 310, 311, and 267, respectively;
(iii) SEQ ID NOs: 263, 265, and 316, respectively;
(iv) SEQ ID NOs: 263, 265, and 320, respectively;
(v) SEQ ID NOs: 263, 265, and 325, respectively;
(vi) SEQ ID NOs: 263, 265, and 329, respectively;
(vii) SEQ ID NOs: 335, 265, and 337, respectively; or
(viii) SEQ ID NOs: 263, 265, and 342, respectively;

(i) a heavy chain variable region having CDRs 1, 2, and 3 comprising the amino acid sequences set forth in SEQ ID NOs: 7, 9, and 11, respectively; and a light chain variable region having
  (i) CDR1 comprising an amino acid sequence selected from SEQ ID NO: 150 and SEQ ID NO: 159;
  (ii) CDR2 comprising an amino acid sequence set forth in SEQ ID NO: 152; and
  (iii) CDR3 comprising an amino acid sequence selected from SEQ ID NO: 154 and SEQ ID NO: 163;
(j) a heavy chain variable region having
  (i) CDR1 comprising an amino acid sequence selected from SEQ ID NOs: 16, 29, and 34;
  (ii) CDR2 comprising an amino acid sequence selected from SEQ ID NOs: 17, 24, and 43; and
  (iii) CDR3 comprising an amino acid sequence selected from SEQ ID NO: 19 and SEQ ID NO: 36; and
a light chain variable region having
  (i) CDR1 comprising an amino acid sequence selected from SEQ ID NO: 176 and SEQ ID NO: 185;
  (ii) CDR2 comprising an amino acid sequence selected from SEQ ID NOs: 138, 178, and 187; and
  (iii) CDR3 comprising an amino acid sequence set forth in SEQ ID NO: 180;
(k) a heavy chain variable region having CDRs 1, 2, and 3 comprising the amino acid sequences set forth in SEQ ID NOs: 49, 51, and 53, respectively; and a light chain variable region having
  (i) CDR1 comprising an amino acid sequence selected from SEQ ID NOs: 195, 204, 216, 230, 236, 247, 251, and 257;
  (ii) CDR2 comprising an amino acid sequence selected from SEQ ID NOs: 197, 205, 217, and 238; and
  (iii) CDR3 comprising an amino acid sequence selected from SEQ ID NOs: 199, 221, and 226;
(l) a heavy chain variable region having
  (i) CDR1 comprising an amino acid sequence set forth in SEQ ID NO: 59;
  (ii) CDR2 comprising an amino acid sequence selected from SEQ ID NOs: 61, 67, and 76; and
  (iii) CDR3 comprising an amino acid sequence selected from SEQ ID NOs: 63, 72, 77, 84, 116, 120, 124, and 129; and
a light chain variable region having
  (i) CDR1 comprising an amino acid sequence selected from SEQ ID NOs: 195, 204, 216, 230, 236, 247, 251, and 257;
  (ii) CDR2 comprising an amino acid sequence selected from SEQ ID NO: 265 and SEQ ID NO: 311; and
  (iii) CDR3 comprising an amino acid sequence selected from SEQ ID NOs: 267, 271, 276, 316, 320, 325, 329, 337, and 342;
(m) a heavy chain variable region having
  (i) CDR1 comprising an amino acid sequence selected from SEQ ID NO: 49 and SEQ ID NO: 94;
  (ii) CDR2 comprising an amino acid sequence selected from SEQ ID NOs: 51, 96, and 110; and
  (iii) CDR3 comprising an amino acid sequence selected from SEQ ID NOs: 98, 103, and 112; and
a light chain variable region having
  (i) CDR1 comprising an amino acid sequence selected from SEQ ID NOs: 285, 292, and 299;
  (ii) CDR2 comprising an amino acid sequence selected from SEQ ID NOs: 205, 287, 293, and 304; and
  (iii) CDR3 comprising an amino acid sequence set forth in SEQ ID NO: 288;
(n) a heavy chain variable region having CDRs 1, 2, and 3 comprising a set of amino acid sequences set forth in
  (i) SEQ ID NOs: 59, 357, and 358, respectively;
  (ii) SEQ ID NOs: 59, 357, and 359, respectively;
  (iii) SEQ ID NOs: 59, 357, and 360, respectively;
  (iv) SEQ ID NOs: 59, 357, and 361, respectively; or
  (v) SEQ ID NOs: 59, 357, and 362, respectively; and
a light chain variable region having CDRs 1, 2, and 3 comprising a set of amino acid sequences set forth in
  (i) SEQ ID NOs: 263, 265, and 363, respectively;
  (ii) SEQ ID NOs: 364, 265, and 365, respectively; or
  (iii) SEQ ID NOs: 366, 367, and 368, respectively; or
(o) a heavy chain variable region having CDRs 1, 2, and 3 comprising the amino acid sequences set forth in SEQ ID NOs: 7, 9, and 11, respectively; and a light chain variable region having CDRs 1, 2, and 3 comprising a set of amino acid sequences set forth in
  (i) SEQ ID NOs: 369, 152, and 154, respectively; or
  (ii) SEQ ID NOs: 369, 152, and 370, respectively.

2. The purified anti-MUC1 binding agent of claim 1, wherein the binding agent comprises:
  (a) a heavy chain variable region having CDRs 1, 2, and 3 comprising a set of amino acid sequences set forth in
    (i) SEQ ID NOs: 16, 17, and 19, respectively;
    (ii) SEQ ID NOs: 16, 24, and 19, respectively;
    (iii) SEQ ID NOs: 29, 24, and 19, respectively;
    (iv) SEQ ID NOs: 34, 17, and 36, respectively;
    (v) SEQ ID NOs: 16, 17, and 36, respectively; or
    (vi) SEQ ID NOs: 16, 43, and 36, respectively; and
  (b) a light chain variable region having CDRs 1, 2, and 3 comprising a set of amino acid sequences set forth in
    (i) SEQ ID NOs: 176, 178, and 180, respectively;
    (ii) SEQ ID NOs: 185, 187, and 180, respectively; or
    (iii) SEQ ID NOs: 185, 138, and 180, respectively.

3. The purified anti-MUC1 binding agent of claim 1, wherein the binding agent comprises:
a heavy chain variable region having CDRs 1, 2, and 3 comprising the amino acid sequences set forth in SEQ ID NOs: 49, 51, and 53, respectively; and
a light chain variable region having CDRs 1, 2, and 3 comprising a set of amino acid sequences set forth in
  (i) SEQ ID NOs: 195, 197, and 199, respectively;
  (ii) SEQ ID NOs: 204, 205, and 199, respectively;
  (iii) SEQ ID NOs: 195, 205, and 199, respectively;
  (iv) SEQ ID NOs: 216, 217, and 199, respectively;
  (v) SEQ ID NOs: 195, 205, and 221, respectively;
  (vi) SEQ ID NOs: 195, 205, and 226, respectively;
  (vii) SEQ ID NOs: 230, 205, and 226, respectively;
  (viii) SEQ ID NOs: 236, 238, and 226, respectively;
  (ix) SEQ ID NOs: 247, 205, and 226, respectively;
  (x) SEQ ID NOs: 251, 205, and 226, respectively; or
  (xi) SEQ ID NOs: 257, 238, and 226, respectively.

4. The purified anti-MUC1 binding agent of claim 1, wherein the binding agent comprises:
a heavy chain variable region having CDRs 1, 2, and 3 comprising a set of amino acid sequences set forth in
  (i) SEQ ID NOs: 59, 61, and 63, respectively;
  (ii) SEQ ID NOs: 59, 67, and 63, respectively;
  (iii) SEQ ID NOs: 59, 61, and 72, respectively;
  (iv) SEQ ID NOs: 59, 76, and 77, respectively;
  (v) SEQ ID NOs: 59, 61, and 77, respectively;
  (vi) SEQ ID NOs: 59, 67, and 116, respectively;
  (vii) SEQ ID NOs: 59, 61, and 120, respectively;
  (viii) SEQ ID NOs: 59, 61, and 84, respectively;
  (ix) SEQ ID NOs: 59, 61, and 124, respectively;
  (x) SEQ ID NOs: 59, 67, and 129, respectively; or
  (xi) SEQ ID NOs: 59, 61, and 89, respectively; and a light chain variable region having CDRs 1, 2, and 3
comprising a set of amino acid sequences set forth in
(i) SEQ ID NOs: 263, 265, and 267, respectively;
(ii) SEQ ID NOs: 310, 311, and 267, respectively;
(iii) SEQ ID NOs: 263, 265, and 316, respectively;
(iv) SEQ ID NOs: 263, 265, and 320, respectively;
(v) SEQ ID NOs: 263, 265, and 325, respectively;
(vi) SEQ ID NOs: 263, 265, and 329, respectively;
(vii) SEQ ID NOs: 335, 265, and 337, respectively;
(viii) SEQ ID NOs: 263, 265, and 342, respectively;
(ix) SEQ ID NOs: 263, 265, and 271, respectively; or
(x) SEQ ID NOs: 263, 265, and 276, respectively.

5. The purified anti-MUC1 binding agent of claim 1, wherein the binding agent comprises:
a heavy chain variable region having CDRs 1, 2, and 3 comprising a set of amino acid sequences set forth in
(i) SEQ ID NOs: 94, 96, and 98, respectively;
(ii) SEQ ID NOs: 49, 51, and 103, respectively; or
(iii) SEQ ID NOs: 49, 110, and 112, respectively; and
a light chain variable region having CDRs 1, 2, and 3 comprising a set of amino acid sequences set forth in
(i) SEQ ID NOs: 263, 265, and 267, respectively;
(ii) SEQ ID NOs: 310, 311, and 267, respectively;
(iii) SEQ ID NOs: 263, 265, and 271, respectively; or
(iv) SEQ ID NOs: 263, 265, and 276, respectively.

6. The purified anti-MUC1 binding agent of claim 1, wherein the binding agent comprises:
a heavy chain variable region having CDRs 1, 2, and 3 comprising the amino acid sequences set forth in SEQ ID NOs: 7, 9, and 11, respectively, and
a light chain variable region having CDRs 1, 2, and 3 comprising the amino acid sequences set forth in SEQ ID NOs: 150, 152, and 163, respectively.

7. The purified anti-MUC1 binding agent of claim 1, wherein the binding agent comprises:
a heavy chain variable region having CDRs 1, 2, and 3 comprising a set of amino acid sequences set forth in
(i) SEQ ID NOs: 59, 61, and 63, respectively;
(ii) SEQ ID NOs: 59, 67, and 63, respectively;
(iii) SEQ ID NOs: 59, 61, and 72, respectively;
(iv) SEQ ID NOs: 59, 76, and 77, respectively;
(v) SEQ ID NOs: 59, 61, and 77, respectively;
(vi) SEQ ID NOs: 59, 67, and 116, respectively;
(vii) SEQ ID NOs: 59, 61, and 120, respectively;
(viii) SEQ ID NOs: 59, 61, and 84, respectively;
(ix) SEQ ID NOs: 59, 61, and 124, respectively;
(x) SEQ ID NOs: 59, 67, and 129, respectively; or
(xi) SEQ ID NOs: 59, 61, and 89, respectively; and
a light chain variable region having CDRs 1, 2, and 3 comprising a set of amino acid sequences set forth in
(i) SEQ ID NOs: 263, 265, and 267, respectively;
(ii) SEQ ID NOs: 310, 311, and 267, respectively;
(iii) SEQ ID NOs: 263, 265, and 316, respectively;
(iv) SEQ ID NOs: 263, 265, and 320, respectively;
(v) SEQ ID NOs: 263, 265, and 325, respectively;
(vi) SEQ ID NOs: 263, 265, and 329, respectively;
(vii) SEQ ID NOs: 335, 265, and 337, respectively; or
(viii) SEQ ID NOs: 263, 265, and 342, respectively.

8. The purified anti-MUC1 binding agent of claim 1, wherein the binding agent comprises:
a heavy chain variable region having CDRs 1, 2, and 3 comprising the amino acid sequences set forth in SEQ ID NOs: 7, 9, and 11, respectively; and
a light chain variable region having
(i) CDR1 comprising an amino acid sequence selected from SEQ ID NO: 150 and SEQ ID NO: 159;
(ii) CDR2 comprising an amino acid sequence set forth in SEQ ID NO: 152; and
(iii) CDR3 comprising an amino acid sequence selected from SEQ ID NO: 154 and SEQ ID NO: 163.

9. The purified anti-MUC1 binding agent of claim 1, wherein the binding agent comprises:
a heavy chain variable region having
(i) CDR1 comprising an amino acid sequence selected from SEQ ID NOs: 16, 29, and 34;
(ii) CDR2 comprising an amino acid sequence selected from SEQ ID NOs: 17, 24, and 43; and
(iii) CDR3 comprising an amino acid sequence selected from SEQ ID NO: 19 and SEQ ID NO: 36; and
a light chain variable region having
(i) CDR1 comprising an amino acid sequence selected from SEQ ID NO: 176 and SEQ ID NO: 185;
(ii) CDR2 comprising an amino acid sequence selected from SEQ ID NOs: 138, 178, and 187; and
(iii) CDR3 comprising an amino acid sequence set forth in SEQ ID NO: 180.

10. The purified anti-MUC1 binding agent of claim 1, wherein the binding agent comprises:
a heavy chain variable region having CDRs 1, 2, and 3 comprising the amino acid sequences set forth in SEQ ID NOs: 49, 51, and 53, respectively; and
a light chain variable region having
(i) CDR1 comprising an amino acid sequence selected from SEQ ID NOs: 195, 204, 216, 230, 236, 247, 251, and 257;
(ii) CDR2 comprising an amino acid sequence selected from SEQ ID NOs: 197, 205, 217, and 238; and
(iii) CDR3 comprising an amino acid sequence selected from SEQ ID NOs: 199, 221, and 226.

11. The purified anti-MUC1 binding agent of claim 1, wherein the binding agent comprises:
a heavy chain variable region having
(i) CDR1 comprising an amino acid sequence set forth in SEQ ID NO: 59;
(ii) CDR2 comprising an amino acid sequence selected from SEQ ID NOs: 61, 67, and 76; and
(iii) CDR3 comprising an amino acid sequence selected from SEQ ID NOs: 63, 72, 77, 84, 116, 120, 124, and 129; and
a light chain variable region having
(i) CDR1 comprising an amino acid sequence selected from SEQ ID NOs: 195, 204, 216, 230, 236, 247, 251, and 257;
(ii) CDR2 comprising an amino acid sequence selected from SEQ ID NO: 265 and SEQ ID NO: 311; and
(iii) CDR3 comprising an amino acid sequence selected from SEQ ID NOs: 267, 271, 276, 316, 320, 325, 329, 337, and 342.

12. The purified anti-MUC1 binding agent of claim 1, wherein the binding agent comprises:
a heavy chain variable region having
(i) CDR1 comprising an amino acid sequence selected from SEQ ID NO: 49 and SEQ ID NO: 94;
(ii) CDR2 comprising an amino acid sequence selected from SEQ ID NOs: 51, 96, and 110; and
(iii) CDR3 comprising an amino acid sequence selected from SEQ ID NOs: 98, 103, and 112, and
a light chain variable region having
(i) CDR1 comprising an amino acid sequence selected from SEQ ID NOs: 285, 292, and 299;
(ii) CDR2 comprising an amino acid sequence selected from SEQ ID NOs: 205, 287, 293, and 304; and (iii) CDR3 comprising an amino acid sequence set forth in SEQ ID NO: 288.

13. The purified anti-MUC1 binding agent of claim 1, wherein the binding agent comprises:
a heavy chain variable region having CDRs 1, 2, and 3 comprising a set of amino acid sequences set forth in
(i) SEQ ID NOs: 59, 357, and 358, respectively;
(ii) SEQ ID NOs: 59, 357, and 359, respectively;
(iii) SEQ ID NOs: 59, 357, and 360, respectively;
(iv) SEQ ID NOs: 59, 357, and 361, respectively; or
(v) SEQ ID NOs: 59, 357, and 362, respectively, and
a light chain variable region having CDRs 1, 2, and 3 comprising a set of amino acid sequences set forth in
(i) SEQ ID NOs: 263, 265, and 363, respectively;
(ii) SEQ ID NOs: 364, 265, and 365, respectively; or
(iii) SEQ ID NOs: 366, 367, and 368, respectively.

14. The purified anti-MUC1 binding agent of claim 1, wherein the binding agent comprises:
a heavy chain variable region having CDRs 1, 2, and 3 comprising the amino acid sequences set forth in SEQ ID NOs: 7, 9, and 11, respectively; and
a light chain variable region having CDRs 1, 2, and 3 comprising a set of amino acid sequences set forth in
(i) SEQ ID NOs: 369, 152, and 154, respectively; or
(ii) SEQ ID NOs: 369, 152, and 370, respectively.

15. A purified anti-MUC1 binding agent comprising
(a) a heavy chain variable region comprising the amino acid sequence of SEQ ID NO: 5; and a light chain variable region comprising the amino acid sequence of SEQ ID NO: 148, 158, 162, 167, or 170;
(b) a heavy chain variable region comprising the amino acid sequence of SEQ ID NO: 15, 23, 28, 33, 39, or 42; and a light chain variable region comprising the amino acid sequence of SEQ ID NO: 174, 184, or 190;
(c) a heavy chain variable region comprising the amino acid sequence of SEQ ID NO: 47; and a light chain variable region comprising the amino acid sequence of SEQ ID NO: 193, 203, 208, 211, 215, 220, 225, 229, 234, 242, 246, 250, or 255;
(d) a heavy chain variable region comprising the amino acid sequence of SEQ ID NO: 57, 66, 70, 75, 80, 83, 87, 115, 119, 123, 127, 132, 141, or 145; and a light chain variable region comprising an amino acid sequence the amino acid sequence of SEQ ID NO: 261, 270, 275, 279, 308, 315, 319, 323, 328, 333, or 340; or
(e) a heavy chain variable region comprising an amino acid sequence the amino acid sequence of SEQ ID NO: 92, 101, 106, or 109; and a the amino acid sequence of SEQ ID NO: 283, 291, 297, or 303.

16. The purified anti-MUC1 binding agent of claim 1, comprising:
(a) a heavy chain variable region comprising an amino acid sequence at least 80% identical to SEQ ID NO: 5; and a light chain variable region comprising an amino acid sequence at least 80% identical to SEQ ID NO: 148, 158, 162, 167, or 170;
(b) a heavy chain variable region comprising an amino acid sequence at least 80% identical to SEQ ID NO: 15, 23, 28, 33, 39, or 42; and a light chain variable region comprising an amino acid sequence at least 80% identical to SEQ ID NO: 174, 184, or 190;
(c) a heavy chain variable region comprising an amino acid sequence at least 80% identical to SEQ ID NO: 47; and a light chain variable region comprising an amino acid sequence at least 80% identical to SEQ ID NO: 193, 203, 208, 211, 215, 220, 225, 229, 234, 242, 246, 250, or 255;
(d) a heavy chain variable region comprising an amino acid sequence at least 80% identical to SEQ ID NO: 57, 66, 70, 75, 80, 83, 87, 115, 119, 123, 127, 132, 141, or 145; and a light chain variable region comprising an amino acid sequence at least 80% identical to SEQ ID NO: 261, 270, 275, 279, 308, 315, 319, 323, 328, 333, or 340; or
(e) a heavy chain variable region comprising an amino acid sequence at least 80% identical to SEQ ID NO: 92, 101, 106, or 109; and a light chain variable region comprising an amino acid sequence at least 80% identical to SEQ ID NO: 283, 291, 297, or 303.

17. The purified anti-MUC1 binding agent of claim 16, wherein the binding agent comprises:
a heavy chain variable region comprising an amino acid sequence at least 80% identical to SEQ ID NO: 15, 23, 28, 33, 39, or 42; and
a light chain variable region comprising an amino acid sequence at least 80% identical to SEQ ID NO: 174, 184, or 190.

18. The purified anti-MUC1 binding agent of claim 16, wherein the binding agent comprises:
a heavy chain variable region comprising an amino acid sequence at least 80% identical to SEQ ID NO: 47; and
a light chain variable region comprising an amino acid sequence at least 80% identical to SEQ ID NO: 193, 203, 208, 211, 215, 220, 225, 229, 234, 242, 246, 250, or 255.

19. The purified anti-MUC1 binding agent of claim 16, wherein the binding agent comprises:
a heavy chain variable region comprising an amino acid sequence at least 80% identical to SEQ ID NO: 57, 66, 70, 75, 80, 83, 87, 115, 119, 123, 127, 132, 141, or 145; and
a light chain variable region comprising an amino acid sequence at least 80% identical to SEQ ID NO: 261, 270, 275, 279, 308, 315, 319, 323, 328, 333, or 340.

20. The purified anti-MUC1 binding agent of claim 16, wherein the binding agent comprises:
a heavy chain variable region comprising an amino acid sequence at least 80% identical to SEQ ID NO: 92, 101, 106, or 109; and
a light chain variable region comprising an amino acid sequence at least 80% identical to SEQ ID NO: 283, 291, 297, or 303.

21. The purified anti-MUC1 binding agent of claim 1, comprising:
(a) a heavy chain comprising an amino acid sequence at least 80% to SEQ ID NO: 3; and a light chain comprising an amino acid sequence at least 80% identical to SEQ ID NO: 146, 156, 160, 165, or 168;
(b) a heavy chain comprising an amino acid sequence at least 80% identical to SEQ ID NO: 13, 21, 26, 31, 37, or 40; and a light chain comprising an amino acid sequence at least 80% identical to SEQ ID NO: 172, 182, or 188;
(c) a heavy chain comprising an amino acid sequence at least 80% identical SEQ ID NO: 45; and a light chain comprising an amino acid sequence at least 80% identical to SEQ ID NO: 191, 201, 206, 209, 213, 218, 223, 227, 232, 240, 244, 248, or 253;
(d) a heavy chain comprising an amino acid sequence at least 80% identical to SEQ ID NO: 55, 64, 68, 73, 78, 81, 85, 113, 117, 121, 125, 130, 139, or 143; and a light chain comprising an amino acid sequence at least 80% identical to SEQ ID NO: 259, 268, 273, 277, 306, 313, 317, 321, 326, 331, or 338; or (e) a heavy chain comprising an amino acid sequence at least 80% identical to SEQ ID NO: 90, 99, 104, or 107; and a light chain comprising an amino acid sequence at least 80% identical to SEQ ID NO: 281, 289, 295, or 301.

22. The purified anti-MUC1 binding agent of claim 21, wherein the binding agent comprises:
a heavy chain comprising an amino acid sequence at least 80% identical to SEQ ID NO: 13, 21, 26, 31, 37, or 40; and
a light chain comprising an amino acid sequence at least 80% identical to SEQ ID NO: 172, 182, or 188.

23. The purified anti-MUC1 binding agent of claim 21, wherein the binding agent comprises:
a heavy chain comprising an amino acid sequence at least 80% identical to SEQ ID NO: 45; and
a light chain comprising an amino acid sequence at least 80% identical SEQ ID NO: 191, 201, 206, 209, 213, 218, 223, 227, 232, 240, 244, 248, or 253.

24. The purified anti-MUC1 binding agent of claim 21, wherein the binding agent comprises:
a heavy chain comprising an amino acid sequence at least 80% identical to SEQ ID NO: 55, 64, 68, 73, 78, 81, 85, 113, 117, 121, 125, 130, 139, or 143; and
a light chain comprising an amino acid sequence at least 80% to SEQ ID NO: 259, 268, 273, 277, 306, 313, 317, 321, 326, 331, or 338.

25. The purified anti-MUC1 binding agent of claim 21, wherein the binding agent comprises:
a heavy chain comprising an amino acid sequence at least 80% identical to SEQ ID NO: 90, 99, 104, or 107; and
a light chain comprising an amino acid sequence at least 80% identical to SEQ ID NO: 281, 289, 295, or 301.

26. The binding agent of claim 1, wherein the binding agent is a human antibody.

27. A method of detecting a MUC1 polypeptide in a sample, the method comprising:
contacting a sample with the binding agent of claim 1; and
detecting binding of the binding agent to the sample, thereby detecting a MUC1 polypeptide in the sample.

28. A composition comprising the binding agent of claim 1 conjugated to a cytotoxic drug.

29. A method for treatment of a cancer comprising administering a therapeutically effective amount of the binding agent of claim 1 to a subject with the cancer, thereby treating the cancer, wherein cells in the cancer express MUC-1, and wherein:
a) the binding agent is an antibody or a chimeric antigen receptor, or
b) the binding agent is conjugated to a therapeutic agent.

30. The method of claim 29, wherein the subject is a human.

31. A method of inhibiting proliferation of a cell comprising contacting the cell with the binding agent of claim 1, thereby inhibiting proliferation of the cell, wherein the cell expresses MUC-1, and wherein:
a) the binding agent is an antibody or a chimeric antigen receptor, or
b) the binding agent is conjugated to a therapeutic agent.

32. A polynucleotide that encodes a chimeric antigen receptor comprising a sequence of an anti-MUC1 binding agent of claim 1.

33. A vector comprising the polynucleotide of claim 32.

34. The vector of claim 33, wherein the vector is a lentiviral or retroviral vector.

35. An isolated recombinant cell that expresses a chimeric antigen receptor comprising a sequence of an anti-MUC1 binding agent of claim 1.

36. The recombinant isolated cell of claim 35, wherein the cell is a T cell.

37. The purified anti-MUC-1 binding agent of claim 13, wherein the anti-MUC1 binding agent is a monoclonal antibody or antigen binding fragment thereof.

38. The purified anti-MUC-1 binding agent of claim 37, wherein the antigen binding fragment is a scFV fragment.

39. The purified anti-MUC-1 binding agent of claim 13, wherein the anti-MUC1 binding agent is a chimeric antigen receptor.

40. The purified anti-MUC-1 binding agent of claim 1, wherein the anti-MUC1 binding agent is a chimeric antigen receptor.

41. A polynucleotide comprising a sequence that encodes the scFV of claim 38.

42. A recombinant vector comprising the polynucleotide of claim 41.

43. An isolated cell comprising the vector of claim 42.

44. A method of producing an anti-MUC1 binding agent, the method comprising culturing the cell of claim 43 under conditions where the binding agent is expressed and collecting the binding agent.

* * * * *

UNITED STATES PATENT AND TRADEMARK OFFICE
CERTIFICATE OF CORRECTION

| | | |
|---|---|---|
| PATENT NO. | : 10,208,125 B2 | Page 1 of 1 |
| APPLICATION NO. | : 14/904575 | |
| DATED | : February 19, 2019 | |
| INVENTOR(S) | : Schoen et al. | |

It is certified that error appears in the above-identified patent and that said Letters Patent is hereby corrected as shown below:

In the Specification

Column 1, beginning at Line 15, please insert:
--STATEMENT OF GOVERNMENT SUPPORT
This invention was made with government support under grant number P01CA73743, awarded by the National Institutes of Health. The government has certain rights in the invention.--

Signed and Sealed this
Seventh Day of May, 2019

Andrei Iancu
*Director of the United States Patent and Trademark Office*

SEQUENCE LISTING

```
<160> NUMBER OF SEQ ID NOS: 371

<210> SEQ ID NO 1
<211> LENGTH: 1255
<212> TYPE: PRT
<213> ORGANISM: Homo sapiens

<400> SEQUENCE: 1

Met Thr Pro Gly Thr Gln Ser Pro Phe Phe Leu Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
```

```
            225                 230                 235                 240
Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
                260                 265                 270

Pro Pro Ala His Gly Val Thr Ser Ala Pro Asp Thr Arg Pro Ala Pro
                275                 280                 285

Gly Ser Thr Ala Pro Pro Ala His Gly Val Thr Ser Ala Pro Asp Thr
                290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
                340                 345                 350

Pro Pro Ala His Gly Val Thr Ser Ala Pro Asp Thr Arg Pro Ala Pro
                355                 360                 365

Gly Ser Thr Ala Pro Pro Ala His Gly Val Thr Ser Ala Pro Asp Thr
                370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
                420                 425                 430

Pro Pro Ala His Gly Val Thr Ser Ala Pro Asp Thr Arg Pro Ala Pro
                435                 440                 445

Gly Ser Thr Ala Pro Pro Ala His Gly Val Thr Ser Ala Pro Asp Thr
                450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
                500                 505                 510

Pro Pro Ala His Gly Val Thr Ser Ala Pro Asp Thr Arg Pro Ala Pro
                515                 520                 525

Gly Ser Thr Ala Pro Pro Ala His Gly Val Thr Ser Ala Pro Asp Thr
                530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
                580                 585                 590

Pro Pro Ala His Gly Val Thr Ser Ala Pro Asp Thr Arg Pro Ala Pro
                595                 600                 605

Gly Ser Thr Ala Pro Pro Ala His Gly Val Thr Ser Ala Pro Asp Thr
                610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655
```

```
Gly Val Thr Ser Ala Pro Asp Thr Arg Pro Ala Pro Gly Ser Thr Ala
              660                 665                 670

Pro Pro Ala His Gly Val Thr Ser Ala Pro Asp Thr Arg Pro Ala Pro
        675                 680                 685

Gly Ser Thr Ala Pro Pro Ala His Gly Val Thr Ser Ala Pro Asp Thr
690                 695                 700

Arg Pro Ala Pro Gly Ser Thr Ala Pro Pro Ala His Gly Val Thr Ser
705                 710                 715                 720

Ala Pro Asp Thr Arg Pro Ala Pro Gly Ser Thr Ala Pro Pro Ala His
            725                 730                 735

Gly Val Thr Ser Ala Pro Asp Thr Arg Pro Ala Pro Gly Ser Thr Ala
                740                 745                 750

Pro Pro Ala His Gly Val Thr Ser Ala Pro Asp Thr Arg Pro Ala Pro
        755                 760                 765

Gly Ser Thr Ala Pro Pro Ala His Gly Val Thr Ser Ala Pro Asp Thr
770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
            805                 810                 815

Gly Val Thr Ser Ala Pro Asp Thr Arg Pro Ala Pro Gly Ser Thr Ala
                820                 825                 830

Pro Pro Ala His Gly Val Thr Ser Ala Pro Asp Thr Arg Pro Ala Pro
        835                 840                 845

Gly Ser Thr Ala Pro Pro Ala His Gly Val Thr Ser Ala Pro Asp Thr
850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
            885                 890                 895

Gly Val Thr Ser Ala Pro Asp Thr Arg Pro Ala Pro Gly Ser Thr Ala
                900                 905                 910

Pro Pro Ala His Gly Val Thr Ser Ala Pro Asp Thr Arg Pro Ala Pro
        915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
                965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065
```

```
Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110

Val His Asp Val Glu Thr Gln Phe Asn Gln Tyr Lys Thr Glu Ala
    1115                1120                1125

Ala Ser Arg Tyr Asn Leu Thr Ile Ser Asp Val Ser Val Ser Asp
    1130                1135                1140

Val Pro Phe Pro Phe Ser Ala Gln Ser Gly Ala Gly Val Pro Gly
    1145                1150                1155

Trp Gly Ile Ala Leu Leu Val Leu Val Cys Val Leu Val Ala Leu
    1160                1165                1170

Ala Ile Val Tyr Leu Ile Ala Leu Ala Val Cys Gln Cys Arg Arg
    1175                1180                1185

Lys Asn Tyr Gly Gln Leu Asp Ile Phe Pro Ala Arg Asp Thr Tyr
    1190                1195                1200

His Pro Met Ser Glu Tyr Pro Thr Tyr His Thr His Gly Arg Tyr
    1205                1210                1215

Val Pro Pro Ser Ser Thr Asp Arg Ser Pro Tyr Glu Lys Val Ser
    1220                1225                1230

Ala Gly Asn Gly Gly Ser Ser Leu Ser Tyr Thr Asn Pro Ala Val
    1235                1240                1245

Ala Ala Thr Ser Ala Asn Leu
    1250                1255

<210> SEQ ID NO 2
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gly Val Thr Ser Ala Pro Asp Thr Arg Pro Ala Pro Gly Ser Thr Ala
1               5                   10                  15

Pro Pro Ala His Gly Val Thr Ser Ala Pro Asp Thr Arg Pro Ala Pro
                20                  25                  30

Gly Ser Thr Ala Pro Pro Ala His Gly Val Thr Ser Ala Pro Asp Thr
            35                  40                  45

Arg Pro Ala Pro Gly Ser Thr Ala Pro Pro Ala His Gly Val Thr Ser
        50                  55                  60

Ala Pro Asp Thr Arg Pro Ala Pro Gly Ser Thr Ala Pro Pro Ala His
65                  70                  75                  80

Gly Val Thr Ser Ala Pro Asp Thr Arg Pro Ala Pro Gly Ser Thr Ala
                85                  90                  95

Pro Pro Ala His
            100

<210> SEQ ID NO 3
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 3

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser
            20                  25                  30

Arg Tyr Tyr Trp Gly Trp Ile Arg Gln Pro Pro Gly Lys Gly Leu Glu
                35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Asn Asn Gln Phe
65                  70                  75                  80

Ser Leu Lys Leu Thr Ser Val Thr Ala Ala Asp Thr Ala Val Tyr Tyr
                85                  90                  95

Cys Ala Arg Leu Pro Glu Ser Gly Gly Tyr Ser Gly Trp Phe Asp Pro
                100                 105                 110

Trp Gly Gln Gly Thr Leu Val Thr Val Ser Ser Ala Ser Thr Lys Gly
            115                 120                 125

Pro Ser Val Arg Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

```
                 405                 410                 415
Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 4
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cagctgcagc tgcaggagtc gggcccagga ctggtgaagc cttcggagac cctgtccctc      60
acctgcactg tctctggtgg ctccatcagc agtagtcgtt actactgggg ctggatccgc     120
cagcccccag ggaaggggct ggagtggatt gggagtatct attatagtgg gagcacctac     180
tacaacccgt ccctcaagag tcgagtcacc atatccgtag acacgtccaa caaccagttc     240
tccctgaagc tgacctctgt gaccgccgca gacacggctg tgtattactg tgcgagactc     300
cccgaaagtg ggggctactc ggggtggttc gacccctggg gccagggaac cctggtcacc     360
gtctcctca                                                             369

<210> SEQ ID NO 5
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Arg Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Asn Asn Gln Phe
65                  70                  75                  80

Ser Leu Lys Leu Thr Ser Val Thr Ala Ala Asp Thr Ala Val Tyr Tyr
            85                  90                  95

Cys Ala Arg Leu Pro Glu Ser Gly Gly Tyr Ser Gly Trp Phe Asp Pro
        100                 105                 110

Trp Gly Gln Gly Thr Leu Val Thr Val Ser Ser
    115                 120

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 6

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ser Arg Tyr Tyr Trp Gly
1               5

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ile Arg Gln Pro Pro Gly Lys Gly Leu Glu Trp Ile Gly
1               5                   10

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ile Tyr Tyr Ser Gly Ser Thr Tyr Tyr Asn Pro Ser Leu Lys Ser
1               5                   10                  15

<210> SEQ ID NO 10
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Arg Val Thr Ile Ser Val Asp Thr Ser Asn Asn Gln Phe Ser Leu Lys
1               5                   10                  15

Leu Thr Ser Val Thr Ala Ala Asp Thr Ala Val Tyr Tyr Cys Ala Arg
            20                  25                  30

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Leu Pro Glu Ser Gly Gly Tyr Ser Gly Trp Phe Asp Pro
 1               5                  10
```

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Trp Gly Gln Gly Thr Leu Val Thr Val Ser Ser
 1               5                  10
```

<210> SEQ ID NO 13
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr His Tyr Asn Pro Ser
     50                  55                  60

Leu Lys Arg Arg Val Thr Ile Ser Glu Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Val Val Glu Val Arg Gly Asn His Tyr Tyr Tyr Tyr
            100                 105                 110

Tyr Met Asp Val Trp Gly Lys Gly Thr Thr Val Thr Val Ser Ser Ala
        115                 120                 125

Ser Thr Lys Gly Pro Ser Val Arg Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270
```

```
Val Val Asp Val Ser His Glu Asp Pro Glu Val Lys Phe Asn Trp Tyr
            275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 14
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
cagctgcagc tgcaggagtc gggcccagga ctggtgaagc cttcggagac cctgtccctc      60
acctgcactg tctctggtgg ctccatcagc agtagtagtt actactgggg ctggatccgc     120
cagcccccag ggaaggggtt ggagtggatt gggagtatct attatagtgg gagcacccac     180
tacaacccgt ccctcaagag gcgagtcacc atatcagaag acacgtccaa gaaccagttc     240
tccctgaagc tgagctctgt gaccgccgcg gacacggccg tgtattactg cgagaggg      300 gtggttgagg ttcggggaaa ccactactac tactactaca tggacgtctg gggcaaaggg     360
accacggtca ccgtctcctc a                                               381

<210> SEQ ID NO 15
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
```

```
                35                  40                  45
Trp Ile Gly Ser Ile Tyr Tyr Ser Gly Ser Thr His Tyr Asn Pro Ser
        50                  55                  60

Leu Lys Arg Arg Val Thr Ile Ser Glu Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Gly Val Val Glu Val Arg Gly Asn His Tyr Tyr Tyr Tyr
            100                 105                 110

Tyr Met Asp Val Trp Gly Lys Gly Thr Thr Val Thr Val Ser Ser
            115                 120                 125

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ser Ser Tyr Tyr Trp Gly
1               5

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ile Tyr Tyr Ser Gly Ser Thr His Tyr Asn Pro Ser Leu Lys Arg
1               5                   10                  15

<210> SEQ ID NO 18
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Arg Val Thr Ile Ser Glu Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Val Val Glu Val Arg Gly Asn His Tyr Tyr Tyr Tyr Tyr Met Asp
1               5                   10                  15

Val
```

```
<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Trp Gly Lys Gly Thr Thr Val Thr Val Ser Ser
1               5                   10

<210> SEQ ID NO 21
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Gly Val Val Glu Val Arg Gly Asn His Tyr Tyr Tyr Tyr
            100                 105                 110

Tyr Met Asp Val Trp Gly Lys Gly Thr Thr Val Thr Val Ser Ser Ala
        115                 120                 125

Ser Thr Lys Gly Pro Ser Val Arg Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
```

```
                290                 295                 300
Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
                340                 345                 350

Pro Arg Glu Pro Gln Val Tyr Thr Leu Pro Pro Ser Arg Glu Glu Met
                355                 360                 365

Thr Lys Asn Gln Val Ser Leu Thr Cys Leu Val Lys Gly Phe Tyr Pro
                370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
                420                 425                 430

Phe Ser Cys Ser Val Met His Glu Ala Leu His Asn His Tyr Thr Gln
                435                 440                 445

Lys Ser Leu Ser Leu Ser Pro Gly Lys
    450                 455

<210> SEQ ID NO 22
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
cagctgcagc tgcaggagtc gggcccagga ctggtgaagc cttcggagac cctgtccctc        60
acctgcactg tctctggtgg ctccatcagc agtagtagtt actactgggg ctggatccgc       120
cagcccccag ggaagggct ggagtggatt gggagtatct attatagtgg gagcacccac       180
tacaacccgt ccctcaagag tcgagtcacc atatcagtag acacgtccaa gaaccagttc       240
tccctgaagc tgaggtctgt gaccgccgcg gacacggccg tgtattactg tgcgagaggg       300
gtggttgagg ttcggggaaa ccactactac tactactaca tggacgtctg ggcaaaggg        360 accacggtca ccgtctcctc a                                                 381

<210> SEQ ID NO 23
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr His Tyr Asn Pro Ser
        50                  55                  60
```

```
Leu Lys Ser Arg Val Thr Ile Ser Val Asp Thr Ser Lys Asn Gln Phe
 65                  70                  75                  80

Ser Leu Lys Leu Arg Ser Val Thr Ala Ala Asp Thr Ala Val Tyr Tyr
                 85                  90                  95

Cys Ala Arg Gly Val Val Glu Val Arg Gly Asn His Tyr Tyr Tyr Tyr
            100                 105                 110

Tyr Met Asp Val Trp Gly Lys Gly Thr Thr Val Thr Val Ser Ser
        115                 120                 125
```

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

```
Ser Ile Tyr Tyr Ser Gly Ser Thr His Tyr Asn Pro Ser Leu Lys Ser
1               5                   10                  15
```

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

```
Arg Val Thr Ile Ser Val Asp Thr Ser Lys Asn Gln Phe Ser Leu Lys
1               5                   10                  15

Leu Arg Ser Val Thr Ala Ala Asp Thr Ala Val Tyr Tyr Cys Ala Arg
            20                  25                  30
```

<210> SEQ ID NO 26
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 26

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Leu Gly Trp Ile His Gln Pro Pro Gly Met Gly Leu Glu
        35                  40                  45

Trp Ile Gly Ser Ile Tyr Tyr Ser Gly Ser Thr His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Gly Val Val Glu Val Arg Gly Asn His Tyr Tyr Tyr Tyr
            100                 105                 110

Tyr Met Asp Val Trp Gly Lys Gly Thr Thr Val Thr Val Ser Ser Ala
        115                 120                 125
```

```
Ser Thr Lys Gly Pro Ser Val Arg Pro Leu Ala Pro Ser Ser Lys Ser
    130                 135                 140
Thr Ser Gly Gly Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
            180                 185                 190
Ser Ser Val Val Thr Val Pro Ser Ser Ser Leu Gly Thr Gln Thr Tyr
        195                 200                 205
Ile Cys Asn Val Asn His Lys Pro Ser Asn Thr Lys Val Asp Lys Arg
    210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
                260                 265                 270
Val Val Asp Val Ser His Glu Asp Pro Glu Val Lys Phe Asn Trp Tyr
            275                 280                 285
Val Asp Gly Val Glu Val His Asn Ala Lys Thr Lys Pro Arg Glu Glu
        290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
            340                 345                 350
Pro Arg Glu Pro Gln Val Tyr Thr Leu Pro Pro Ser Arg Glu Glu Met
        355                 360                 365
Thr Lys Asn Gln Val Ser Leu Thr Cys Leu Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
        435                 440                 445
Lys Ser Leu Ser Leu Ser Pro Gly Lys
    450                 455

<210> SEQ ID NO 27
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cagctgcagc tgcaggagtc gggcccagga ctggtgaagc cttcggagac cctgtccctc    60
acctgcactg tctctggtgg ctccatcagc agtagtagtt actacttggg ctggatccac   120
cagcccccag ggatggggct ggagtggatt gggagtatct attatagtgg gagcacccac   180
```

```
tacaacccgt ccctcaagag tcgagtcacc atatcagtag acacgtccaa gaaccagttc    240
tccctgaagc tgaggtctgt gaccgccgcg gacacggccg tgtattactg tgcgagaggg    300
gtggttgagg ttcggggaaa ccactactac tactactaca tggacgtctg gggcaaaggg    360
accacggtca ccgtctcctc a                                              381
```

```
<210> SEQ ID NO 28
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Leu Gly Trp Ile His Gln Pro Pro Gly Met Gly Leu Glu
        35                  40                  45

Trp Ile Gly Ser Ile Tyr Tyr Ser Gly Ser Thr His Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Gly Val Val Glu Val Arg Gly Asn His Tyr Tyr Tyr Tyr
            100                 105                 110

Tyr Met Asp Val Trp Gly Lys Gly Thr Thr Val Thr Val Ser Ser
        115                 120                 125

```
<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29
```

Ser Ser Ser Tyr Tyr Leu Gly
1               5

```
<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30
```

Trp Ile His Gln Pro Pro Gly Met Gly Leu Glu Trp Ile Gly
1               5                   10

```
<210> SEQ ID NO 31
<211> LENGTH: 457
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 31

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Val Gly Trp Ile Arg His Ala Pro Gly Lys Gly Leu Glu
        35                  40                  45

Trp Ile Gly Ser Ile Tyr Tyr Ser Gly Ser Thr His Tyr Asn Pro Ser
    50                  55                  60

Leu Lys Arg Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Gly Val Val Glu Val Arg Gly Asn His Tyr Tyr Tyr Tyr
        100                 105                 110

His Met Asp Ala Trp Gly Lys Gly Thr Thr Val Thr Val Ser Ser Ala
    115                 120                 125

Ser Thr Lys Gly Pro Ser Val Arg Pro Leu Ala Pro Ser Ser Lys Ser
130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Leu Gly Thr Gln Thr Tyr
    195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
            245                 250                 255

Pro Lys Asp Thr Leu Met Ile Ser Arg Thr Pro Glu Val Thr Cys Val
        260                 265                 270

Val Val Asp Val Ser His Glu Asp Pro Glu Val Lys Phe Asn Trp Tyr
    275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
            325                 330                 335

Ala Leu Pro Ala Pro Ile Glu Lys Thr Ile Ser Lys Ala Lys Gly Gln
        340                 345                 350

Pro Arg Glu Pro Gln Val Tyr Thr Leu Pro Pro Ser Arg Glu Glu Met
    355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400
```

```
Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
        420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 32
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
cagctgcagc tgcaggagtc gggcccagga ctggtgaagc cttcggagac cctgtccctc      60
acctgcactg tctctggtgg ctccatcagc agtagtagtt actacgtggg ctggatccgc     120
cacgccccag ggaaggggtt ggagtggatt gggagtatct attatagtgg gagcacccac     180
tacaacccgt ccctcaagag gcgagtcacc atatcagaag acacgtccaa gaaccagttc     240
tccctgaagc tgagctctgt gaccgccgcg gacacggccg tgtattactg tgcgagaggg     300
gtggttgagg ttcggggaaa ccactactac tactaccaca tggacgcctg ggggcaaggg     360
accacggtca ccgtctcctc a                                                381

<210> SEQ ID NO 33
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Val Gly Trp Ile Arg His Ala Pro Gly Lys Gly Leu Glu
        35                  40                  45

Trp Ile Gly Ser Ile Tyr Tyr Ser Gly Ser Thr His Tyr Asn Pro Ser
    50                  55                  60

Leu Lys Arg Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Val Glu Val Arg Gly Asn His Tyr Tyr Tyr Tyr
            100                 105                 110

His Met Asp Ala Trp Gly Lys Gly Thr Thr Val Thr Val Ser Ser
        115                 120                 125

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 34

Ser Ser Ser Tyr Tyr Val Gly
1               5

<210> SEQ ID NO 35
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ile Arg His Ala Pro Gly Lys Gly Leu Glu Trp Ile Gly
1               5                   10

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Val Val Glu Val Arg Gly Asn His Tyr Tyr Tyr His Met Asp
1               5                   10                  15

Ala

<210> SEQ ID NO 37
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
                20                  25                  30

Ser Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr His Tyr Asn Pro Ser
        50                  55                  60

Leu Lys Arg Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Val Glu Val Arg Gly Asn His Tyr Tyr Tyr
            100                 105                 110

His Met Asp Ala Trp Gly Lys Gly Thr Thr Val Thr Val Ser Ser Ala
            115                 120                 125

Ser Thr Lys Gly Pro Ser Val Arg Pro Leu Ala Pro Ser Ser Lys Ser
            130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly

```
                    165                 170                 175
Val His Thr Phe Pro Ala Val Leu Gln Ser Ser Gly Leu Tyr Ser Leu
                180                 185                 190

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Arg
        210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 38
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag gaaggggtt ggagtggatt gggagtatct attatagtgg gagcacccac   180
tacaacccgt ccctcaagag gcgagtcacc atatcagaag acacgtccaa gaaccagttc   240
tccctgaagc tgagctctgt gaccgccgcg gacacggccg tgtattactg tgcgagaggg   300
gtggttgagg ttcggggaaa ccactactac tactaccaca tggacgcctg gggcaagggg   360
```
accacggtca ccgtctcctc a                                                    381

<210> SEQ ID NO 39
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr His Tyr Asn Pro Ser
    50                  55                  60

Leu Lys Arg Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Val Glu Val Arg Gly Asn His Tyr Tyr Tyr Tyr
            100                 105                 110

His Met Asp Ala Trp Gly Lys Gly Thr Thr Val Thr Val Ser Ser
        115                 120                 125

<210> SEQ ID NO 40
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr His Tyr Thr Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Val Glu Val Arg Gly Asn His Tyr Tyr Tyr Tyr
            100                 105                 110

His Met Asp Ala Trp Gly Lys Gly Thr Thr Val Thr Val Ser Ser Ala
        115                 120                 125

Ser Thr Lys Gly Pro Ser Val Arg Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly 165                 170                 175
Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 41
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
cagctgcagc tgcaggagtc gggcccagga ctggtgaagc cttcggagac cctgtccctc        60
acctgcactg tctctggtgg ctccatcagc agtagtagtt actactgggg ctggatccgc       120
cagcccccag ggaaggggct ggagtggatt gggagtatct attatagtgg gagcacccac       180
tacaccccgt ccctcaagag tcgagtcacc atatcagtag acacgtccaa gaaccagttc       240
tccctgaagc tgagctctgt gaccgccgcg gacacggccg tgtattactg tgcgagaggg       300
gtggttgagg ttcggggaaa ccactactac tactaccaca tggacgcctg gggcaaaggg       360
accacggtca ccgtctcctc a 381

```
<210> SEQ ID NO 42
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr His Tyr Thr Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Val Val Glu Val Arg Gly Asn His Tyr Tyr Tyr Tyr
            100                 105                 110

His Met Asp Ala Trp Gly Lys Gly Thr Thr Val Thr Val Ser Ser
        115                 120                 125

```
<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43
```

Ser Ile Tyr Tyr Ser Gly Ser Thr His Tyr Thr Pro Ser Leu Lys Ser
1               5                   10                  15

```
<210> SEQ ID NO 44
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44
```

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

```
<210> SEQ ID NO 45
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45
```

-continued

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Val Ser Ser Asn
             20                  25                  30

Tyr Met Ser Trp Val Arg Gln Ala Pro Gly Lys Gly Leu Glu Trp Val
             35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Gly Ser Thr Asn Thr Tyr Tyr Asp Ser Ser Gly His Pro Trp
             100                 105                 110

Gly Gln Gly Thr Met Val Thr Val Ser Ser Ala Ser Thr Lys Gly Pro
             115                 120                 125

Ser Val Arg Pro Leu Ala Pro Ser Ser Lys Ser Thr Gly Gly Thr
             130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
             165                 170                 175

Ala Val Leu Gln Ser Ser Gly Leu Tyr Ser Leu Ser Ser Val Val Thr
             180                 185                 190

Val Pro Ser Ser Ser Leu Gly Thr Gln Thr Tyr Ile Cys Asn Val Asn
             195                 200                 205

His Lys Pro Ser Asn Thr Lys Val Asp Lys Arg Val Glu Pro Lys Ser
             210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
             245                 250                 255

Met Ile Ser Arg Thr Pro Glu Val Thr Cys Val Val Val Asp Val Ser
             260                 265                 270

His Glu Asp Pro Glu Val Lys Phe Asn Trp Tyr Val Asp Gly Val Glu
             275                 280                 285

Val His Asn Ala Lys Thr Lys Pro Arg Glu Glu Gln Tyr Asn Ser Thr
             290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
             325                 330                 335

Ile Glu Lys Thr Ile Ser Lys Ala Lys Gly Gln Pro Arg Glu Pro Gln
             340                 345                 350

Val Tyr Thr Leu Pro Pro Ser Arg Glu Glu Met Thr Lys Asn Gln Val
             355                 360                 365

Ser Leu Thr Cys Leu Val Lys Gly Phe Tyr Pro Ser Asp Ile Ala Val
             370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
             405                 410                 415

Val Asp Lys Ser Arg Trp Gln Gln Gly Asn Val Phe Ser Cys Ser Val
```

```
            420                 425                 430
Met His Glu Ala Leu His Asn His Tyr Thr Gln Lys Ser Leu Ser Leu
        435                 440                 445

Ser Pro Gly Lys
    450
```

<210> SEQ ID NO 46
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
gaggtgcagc tggtggagtc tgggggaggc ttggtccagc ctggggggtc cctgagactc      60
tcctgtgcag cctctggatt caccgtcagt agcaactaca tgagctgggt ccgccaggct     120
ccagggaagg ggctggagtg ggtctcagtt atttatagcg gtggtagcac atactacgca     180
gactccgtga agggccgatt caccatctcc agagacaatt ccaagaacac gctgtatctt     240
caaatgaaca gcctgagagc tgaggacacg gctgtgtatt actgtgcgag aggttcaacc     300
aatacgtatt actatgatag tagtggccat ccctggggcc aagggacaat ggtcaccgtc     360
tcttca                                                                366

<210> SEQ ID NO 47
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Thr Asn Thr Tyr Tyr Asp Ser Ser Gly His Pro Trp
            100                 105                 110

Gly Gln Gly Thr Met Val Thr Val Ser Ser
        115                 120
```

<210> SEQ ID NO 48
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Val Ser
            20                  25                  30

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Asn Tyr Met Ser
1               5

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Val Arg Gln Ala Pro Gly Lys Gly Leu Glu Trp Val Ser
1               5                   10

<210> SEQ ID NO 51
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Val Ile Tyr Ser Gly Gly Ser Thr Tyr Tyr Ala Asp Ser Val Lys Gly
1               5                   10                  15

<210> SEQ ID NO 52
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala Arg
            20                  25                  30

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gly Ser Thr Asn Thr Tyr Tyr Tyr Asp Ser Ser Gly His Pro
1               5                   10
```

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Gly Gln Gly Thr Met Val Thr Val Ser Ser
1               5                   10

<210> SEQ ID NO 55
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Gly Tyr Cys Ser Gly Gly Ser Cys Tyr Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

```
Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Glu Glu
                355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
                435                 440                 445

Gln Lys Ser Leu Ser Leu Ser Pro Gly Lys
    450                 455
```

```
<210> SEQ ID NO 56
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg ggtttcatac attagtagta gtggtactac caaatactac   180
gcagactctg tgaagggccg attcaccatc tccagggaca acgccaagaa ctcactgtat   240
ctgcaaatga acagcctgag agccgaggac acggccgtgt attactgtgc gagagaacga   300 ataggtatt gtagtggtgg tagctgctac tactactact acatggacgt ctggggcaaa   360
gggaccacgg tcaccgtctc ctca                                          384
```

```
<210> SEQ ID NO 57
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Thr Thr Lys Tyr Tyr Ala Asp Ser Val
```

```
              50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Arg Ile Gly Tyr Cys Ser Gly Gly Ser Cys Tyr Tyr Tyr
            100                 105                 110

Tyr Tyr Met Asp Val Trp Gly Lys Gly Thr Thr Val Thr Val Ser Ser
        115                 120                 125
```

<210> SEQ ID NO 58
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser
            20                  25                  30
```

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Asp Tyr Tyr Met Ser
 1               5
```

<210> SEQ ID NO 60
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Trp Ile Arg Gln Ala Pro Gly Lys Gly Leu Glu Trp Val Ser
 1               5                  10
```

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Tyr Ile Ser Ser Ser Gly Thr Thr Lys Tyr Tyr Ala Asp Ser Val Lys
 1               5                  10                  15

Gly
```

<210> SEQ ID NO 62
<211> LENGTH: 32
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 62

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Arg Ile Gly Tyr Cys Ser Gly Gly Ser Cys Tyr Tyr Tyr Tyr
1               5                   10                  15

Met Asp Val

<210> SEQ ID NO 64
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Gly Tyr Cys Ser Gly Gly Ser Cys Tyr Tyr Tyr
                100                 105                 110

Tyr Tyr Met Asp Val Trp Gly Lys Gly Thr Thr Val Thr Val Ser Ser
            115                 120                 125

Ala Ser Thr Lys Gly Pro Ser Val Arg Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
                180                 185                 190

Leu Ser Ser Val Val Thr Val Pro Ser Ser Ser Leu Gly Thr Gln Thr
            195                 200                 205
```

Tyr Ile Cys Asn Val Asn His Lys Pro Ser Asn Thr Lys Val Asp Lys
            210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 65
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
caggtgcagc tggtggagtc tgggggaggc ttggtcaagc ctggagggtc cctgagactc        60
tcctgtgcag cctctggatt caccttcagt gactactaca tgagctggat ccgccaggct       120
ccagggaagg gctggagtg gtttcatac attagtagta gtggtagtac catatactac       180
gcagactctg tgaagggccg attcaccatc tccaggaca acgccaagaa ctcactgtat       240
ctgcaaatga acagcctgag agccgaggac acggccgtgt attactgtgc gagagaacga       300
atagggtatt gtagtggtgg tagctgctac tactactact acatggacgt ctggggcaaa       360
gggaccacgg tcaccgtctc ctca                                              384

<210> SEQ ID NO 66
<211> LENGTH: 128
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 66

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Gly Tyr Cys Ser Gly Gly Ser Cys Tyr Tyr Tyr
            100                 105                 110

Tyr Tyr Met Asp Val Trp Gly Lys Gly Thr Thr Val Thr Val Ser Ser
        115                 120                 125

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 67

Tyr Ile Ser Ser Ser Gly Ser Thr Ile Tyr Tyr Ala Asp Ser Val Lys
1               5                   10                  15

Gly

<210> SEQ ID NO 68
<211> LENGTH: 458
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 68

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asn Leu Gly Tyr Cys Ser Gly Gly Ser Cys Tyr Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 69
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
caggtgcagc tggtggagtc tgggggaggc ttggtcaagc ctggagggtc cctgagactc     60
tcctgtgcag cctctggatt caccttcagt gactactaca tgagctggat ccgccaggct    120

```
ccagggaagg ggctggagtg ggtttcatac attagtagta gtggtactac caaatactac    180
gcagactctg tgaagggccg attcaccatc tccagggaca cgccaagaa ctcactgtat    240 ctgcaaatga acagcctgag agccgaggac acggccgtgt attactgtgt gagagagaat    300
ttaggatact gtagtggtgg tagctgctac tactactact acatggacgt ctggggcaaa    360
gggaccacgg tcaccgtctc ctca                                          384
```

<210> SEQ ID NO 70
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asn Leu Gly Tyr Cys Ser Gly Gly Ser Cys Tyr Tyr Tyr
            100                 105                 110

Tyr Tyr Met Asp Val Trp Gly Lys Gly Thr Thr Val Thr Val Ser Ser
        115                 120                 125
```

<210> SEQ ID NO 71
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Val Arg
            20                  25                  30
```

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

```
Glu Asn Leu Gly Tyr Cys Ser Gly Gly Ser Cys Tyr Tyr Tyr Tyr
1               5                   10                  15

Met Asp Val
```

```
<210> SEQ ID NO 73
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asn Leu Gly Tyr Cys Thr Gly Gly Asn Cys Phe Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365
```

```
Met Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
            405                 410                 415
Leu Tyr Ser Lys Leu Thr Val Asp Lys Ser Arg Trp Gln Gln Gly Asn
        420                 425                 430
Val Phe Ser Cys Ser Val Met His Glu Ala Leu His Asn His Tyr Thr
            435                 440                 445
Gln Lys Ser Leu Ser Leu Ser Pro Gly Lys
    450                 455

<210> SEQ ID NO 74
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg gctggagtg gtttcatac attagtagta gtggtagtac caaatattac      180
gcagactctg tgaagggccg attcaccatc tccagggaca acgccaagaa ctcactgtat     240
ctacaaatga acagcctgag agccgaggac acggccgtgt attattgtgt gagagagaat     300
ttaggatact gtactggtgg gaactgcttc tactactact acatggacgt ctggggcaaa     360
gggaccacag tcaccgtctc ctca                                            384

<210> SEQ ID NO 75
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Tyr Met Ser Trp Ile Arg Gln Ala Pro Gly Lys Gly Leu Glu Trp Val
        35                  40                  45
Ser Tyr Ile Ser Ser Ser Gly Ser Thr Lys Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
            85                  90                  95
Val Arg Glu Asn Leu Gly Tyr Cys Thr Gly Gly Asn Cys Phe Tyr Tyr
            100                 105                 110
Tyr Tyr Met Asp Val Trp Gly Lys Gly Thr Thr Val Thr Val Ser Ser
        115                 120                 125
```

```
<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Tyr Ile Ser Ser Ser Gly Ser Thr Lys Tyr Tyr Ala Asp Ser Val Lys
1               5                   10                  15

Gly

<210> SEQ ID NO 77
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Asn Leu Gly Tyr Cys Thr Gly Gly Asn Cys Phe Tyr Tyr Tyr
1               5                   10                  15

Met Asp Val

<210> SEQ ID NO 78
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asn Leu Gly Tyr Cys Thr Gly Gly Asn Cys Phe Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Gln Thr
```

```
                195                 200                 205
Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 79
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
caggtgcagc tggtggagtc tgggggaggc ttggtcaagc ctggagggtc cctgagactc        60
tcctgtgcag cctctggatt caccttcagt gactactaca tgagctggat ccgccaggct       120
ccagggaagg ggctggagtg ggtttcatac attagtagta gtggtactac caaatactac       180
gcagactctg tgaagggccg attcaccatc tccagggaca acgccaagaa ctcactgtat       240
ctgcaaatga acagcctgag agccgaggac acggccgtgt attactgtgt gagagagaat       300
ttaggatact gtactggtgg gaactgcttc tactactact acatggacgt ctggggcaaa       360
gggaccacag tcaccgtctc ctca                                              384

<210> SEQ ID NO 80
<211> LENGTH: 128
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 80

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Val Arg Glu Asn Leu Gly Tyr Cys Thr Gly Gly Asn Cys Phe Tyr Tyr
            100                 105                 110

Tyr Tyr Met Asp Val Trp Gly Lys Gly Thr Thr Val Thr Val Ser Ser
        115                 120                 125
```

<210> SEQ ID NO 81
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Val Arg Glu Asn Ile Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
```

```
                195                 200                 205
Tyr Ile Cys Asn Val Asn His Lys Pro Ser Asn Thr Lys Val Asp Lys
        210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 82
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 82
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg gctggagtg gtttcatac attagtagta gtggtactac caaatactac      180
gcagactctg tgaagggccg attcaccatc tccagggaca acgccaagaa ctcactgtat     240
ctgcaaatga acagcctgag agccgaggac acggccgtgt attactgtgt gagagagaat     300
ataggatact gtagtggtgg gagctgcttc tactactact acatggacgt ctggggcaaa     360
gggaccacgg tcaccgtctc ctca                                            384

<210> SEQ ID NO 83
<211> LENGTH: 128
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 83

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asn Ile Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Asn Ile Gly Tyr Cys Ser Gly Gly Ser Cys Phe Tyr Tyr Tyr Tyr
1               5                   10                  15

Met Asp Val

<210> SEQ ID NO 85
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asp Ile Gly Tyr Cys Ser Gly Gly Ser Cys Phe Tyr Tyr
            100                 105                 110

```
Tyr Tyr Met Asp Val Trp Gly Lys Gly Thr Thr Val Thr Val Ser Ser
            115                 120                 125
Ala Ser Thr Lys Gly Pro Ser Val Arg Pro Leu Ala Pro Ser Ser Lys
130                 135                 140
Ser Thr Ser Gly Gly Thr Ala Ala Leu Gly Cys Leu Val Lys Asp Tyr
145                 150                 155                 160
Phe Pro Glu Pro Val Thr Val Ser Trp Asn Ser Gly Ala Leu Thr Ser
                165                 170                 175
Gly Val His Thr Phe Pro Ala Val Leu Gln Ser Ser Gly Leu Tyr Ser
            180                 185                 190
Leu Ser Ser Val Val Thr Val Pro Ser Ser Ser Leu Gly Thr Gln Thr
        195                 200                 205
Tyr Ile Cys Asn Val Asn His Lys Pro Ser Asn Thr Lys Val Asp Lys
    210                 215                 220
Arg Val Glu Pro Lys Ser Cys Asp Lys Thr His Thr Cys Pro Pro Cys
225                 230                 235                 240
Pro Ala Pro Glu Leu Leu Gly Gly Pro Ser Val Phe Leu Phe Pro Pro
                245                 250                 255
Lys Pro Lys Asp Thr Leu Met Ile Ser Arg Thr Pro Glu Val Thr Cys
            260                 265                 270
Val Val Val Asp Val Ser His Glu Asp Pro Glu Val Lys Phe Asn Trp
        275                 280                 285
Tyr Val Asp Gly Val Glu Val His Asn Ala Lys Thr Lys Pro Arg Glu
    290                 295                 300
Glu Gln Tyr Asn Ser Thr Tyr Arg Val Val Ser Val Leu Thr Val Leu
305                 310                 315                 320
His Gln Asp Trp Leu Asn Gly Lys Glu Tyr Lys Cys Lys Val Ser Asn
                325                 330                 335
Lys Ala Leu Pro Ala Pro Ile Glu Lys Thr Ile Ser Lys Ala Lys Gly
            340                 345                 350
Gln Pro Arg Glu Pro Gln Val Tyr Thr Leu Pro Pro Ser Arg Glu Glu
        355                 360                 365
Met Thr Lys Asn Gln Val Ser Leu Thr Cys Leu Val Lys Gly Phe Tyr
    370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
            420                 425                 430
Val Phe Ser Cys Ser Val Met His Glu Ala Leu His Asn His Tyr Thr
        435                 440                 445
Gln Lys Ser Leu Ser Leu Ser Pro Gly Lys
    450                 455
```

<210> SEQ ID NO 86
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
caggtgcagc tggtggagtc tgggggaggc ttggtcaagc ctggagggtc cctgagactc    60

```
tcctgtgcag cctctggatt catcttcagt gactactaca tgagctggat ccgccaggct    120
ccagggaagg ggctggagtg ggtttcatac attagtagta gtggtactac caaatactac    180
gcagactctg tgaagggccg attcaccatc tccagggaca acgccaagaa ctcactgtat    240
ctgcaaatga acagcctgag agccgaggac acggccgtgt attactgtgt gagagaggat    300
ataggatact gtagtggtgg gagctgcttc tactactact acatggacgt ctggggcaaa    360
gggaccacgg tcaccgtctc ctca                                           384
```

```
<210> SEQ ID NO 87
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asp Ile Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125
```

```
<210> SEQ ID NO 88
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser
            20                  25                  30
```

```
<210> SEQ ID NO 89
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Glu Asp Ile Gly Tyr Cys Ser Gly Gly Ser Cys Phe Tyr Tyr Tyr
1               5                   10                  15

Met Asp Val
```

<210> SEQ ID NO 90
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser His Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ala Asp Trp Gly Gln Gly Thr Leu Val Thr Val Ser
            100                 105                 110

Ser Ala Ser Thr Lys Gly Pro Ser Val Arg Pro Leu Ala Pro Ser Ser
        115                 120                 125

Lys Ser Thr Ser Gly Gly Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
```

```
                355                 360                 365
Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly Lys
            435                 440

<210> SEQ ID NO 91
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
gaggtgcagc tggtggagtc cggggggaggc ttagttcagc ctgggggggtc cctgagactc    60 tcctgtgcag cctctggatt caccttcagt agctactgga tgcactgggt ccgccaagct   120
ccagggaagg ggctggtgtg ggtctcacat attaatagtg atgggagtag cacaagctac   180
gcggactccg tgaagggacg attcaccatc tccagagaca acgccaagaa cacgctgtat   240
ctgcaaatga acagtctgag agccgaggac acggctgtgt attactgtgc aagagagctc   300
gcggactggg gccagggaac cctggtcacc gtctcctca                           339

<210> SEQ ID NO 92
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser His Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Leu Ala Asp Trp Gly Gln Gly Thr Leu Val Thr Val Ser
            100                 105                 110

Ser

<210> SEQ ID NO 93
<211> LENGTH: 30
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 93

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Tyr Trp Met His
1               5

<210> SEQ ID NO 95
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Trp Val Arg Gln Ala Pro Gly Lys Gly Leu Val Trp Val Ser
1               5                   10

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

His Ile Asn Ser Asp Gly Ser Ser Thr Ser Tyr Ala Asp Ser Val Lys
1               5                   10                  15

Gly

<210> SEQ ID NO 97
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 98
<211> LENGTH: 4
<212> TYPE: PRT
<213> ORGANISM: Artificial Sequence
<220> FEATURE:
```

-continued

<223> OTHER INFORMATION: Description of Artificial Sequence: Synthetic
      peptide

<400> SEQUENCE: 98

Glu Leu Ala Asp
1

<210> SEQ ID NO 99
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Ile Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gln Glu His Tyr Phe Asp Gly Ser Gly Tyr Tyr Val Asp Tyr
            100                 105                 110

Trp Gly Gln Gly Thr Leu Val Thr Val Ser Ser Ala Ser Thr Lys Gly
        115                 120                 125

Pro Ser Val Arg Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

```
Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
        450

<210> SEQ ID NO 100
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 100
gaggtgcagc tggtggagtc tgggggaggc ttggtccagc ctggggggtc cctgagactc        60
tcctgtgcag cctctggatt caccgtcagt agcaactaca tgagctgggt ccgccaggct       120
ccagggaagg ggctggagtg gtctcagtt atttatagcg gtggtagcac atactacgca       180
gactccgtga aggcagatt catcatctcc agagacaatt ccaagaacac gctgtatctt       240
caaatgaaca gcctgagagc cgaggacacg gctgtgtatt actgtgcgag agatcaagag       300
cattactttg atggtagtgg ttattacgtt gactactggg gccagggaac cctggtcacc       360
gtctcctca                                                                369

<210> SEQ ID NO 101
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Ile Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
```

```
                    85                  90                  95
Arg Asp Gln Glu His Tyr Phe Asp Gly Ser Gly Tyr Tyr Val Asp Tyr
                100                 105                 110

Trp Gly Gln Gly Thr Leu Val Thr Val Ser Ser
            115                 120

<210> SEQ ID NO 102
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Arg Phe Ile Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 103
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Asp Gln Glu His Tyr Phe Asp Gly Ser Gly Tyr Tyr Val Asp Tyr
1               5                   10                  15

<210> SEQ ID NO 104
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Asp Gln Glu His Tyr Phe Asp Gly Ser Gly Tyr Tyr Val Asp Tyr
                100                 105                 110

Trp Gly Gln Gly Thr Leu Val Thr Val Ser Ser Ala Ser Thr Lys Gly
            115                 120                 125

Pro Ser Val Arg Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160
```

Thr Val Ser Trp Asn Ser Gly Ala Leu Thr Ser Gly Val His Thr Phe
             165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Arg Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 105
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
gaggtgcagc tggtggagtc tgggggaggc ttggtccagc ctgggggtc cctgagactc      60 tcctgtgcag cctctggatt caccgtcagt agcaactaca tgagctgggt ccgccaggct    120
ccagggaagg ggctggagtg ggtctcagtt atttatagcg gtggtagcac atactacgca    180
gactccgtga aggcagatt catcatctcc agagacaatt ccaagaacac gctgtatctt    240
caaatgaaca gcctgagagc cgaggacacg gctgtgtatt actgtgcgag agatcaagag    300

```
cattactttg atggtagtgg ttattacgtt gactactggg gccagggaac cctggtcacc    360
gtctcctca                                                            369
```

<210> SEQ ID NO 106
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gln Glu His Tyr Phe Asp Gly Ser Gly Tyr Tyr Val Asp Tyr
            100                 105                 110

Trp Gly Gln Gly Thr Leu Val Thr Val Ser Ser
        115                 120
```

<210> SEQ ID NO 107
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Thr Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp His Asp Pro Asp Tyr Gly Gly Tyr Tyr Met Asp Val Trp Gly
            100                 105                 110

Lys Gly Thr Thr Val Thr Val Ser Ser Ala Ser Thr Lys Gly Pro Ser
        115                 120                 125

Val Arg Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 108
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
gaggtgcagc tggtggagtc tggaggaggc ttggtccagc ctgggggtc cctgagactc      60 tcctgtgcag cctctgggtt caccgtcagt agcaattaca tgagctgggt ccgccaggct    120
ccagggaagg ggctggagtg ggtctcagtt atttatagcg gtggtaccac atactacgca    180
gactccgtga aggccgatt caccatctcc agacacaatt ccaagaacac gctgtatctt    240
caaatgaaca gcctgagagc tgaggacacg gccgtgtatt actgtgcgag agatcacgat    300

```
cctgattacg gcggctacta catggacgtc tggggcaaag ggaccacggt caccgtctcc    360
tca                                                                  363
```

<210> SEQ ID NO 109
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Thr Thr Tyr Tyr Ala Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp His Asp Pro Asp Tyr Gly Gly Tyr Tyr Met Asp Val Trp Gly
            100                 105                 110

Lys Gly Thr Thr Val Thr Val Ser Ser
        115                 120

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Val Ile Tyr Ser Gly Gly Thr Thr Tyr Tyr Ala Asp Ser Val Lys Gly
1               5                   10                  15

<210> SEQ ID NO 111
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Arg Phe Thr Ile Ser Arg His Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp His Asp Pro Asp Tyr Gly Gly Tyr Tyr Met Asp Val
1               5                   10

<210> SEQ ID NO 113
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Gly Tyr Cys Thr Gly Gly Asn Cys Phe Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

```
Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 114
<211> LENGTH: 384
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 114

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagggaca acgccaagaa ctcactgtat     240
ctgcaaatga acagcctgag agccgaggac acggccgtgt attactgtgc gagagaacga     300
ataggatact gtactggtgg gaactgcttc tactactact acatggacgt ctggggcaaa     360
gggaccacag tcaccgtctc ctca                                            384
```

<210> SEQ ID NO 115
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 115

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Gly Tyr Cys Thr Gly Gly Asn Cys Phe Tyr Tyr
```

```
                      100                 105                 110
Tyr Tyr Met Asp Val Trp Gly Lys Gly Thr Thr Val Thr Val Ser Ser
        115                 120                 125

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Glu Arg Ile Gly Tyr Cys Thr Gly Gly Asn Cys Phe Tyr Tyr Tyr
1               5                  10                  15

Met Asp Val

<210> SEQ ID NO 117
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asn Ile Gly Tyr Cys Thr Gly Gly Asn Cys Phe Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255
```

```
Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 118
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 118
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtactac caaatactac     180
gcagactctg tgaagggccg attcaccatc tccagggaca cgccaagaa ctcactgtat      240 ctgcaaatga acagcctgag agccgaggac acggccgtgt attactgtgt gagagagaat     300
ataggatact gtactggtgg gaactgcttc tactactact acatggacgt ctggggcaaa     360
gggaccacag tcaccgtctc ctca                                            384

<210> SEQ ID NO 119
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Gln Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Val Arg Glu Asn Ile Gly Tyr Cys Thr Gly Gly Asn Cys Phe Tyr Tyr
            100                 105                 110

Tyr Tyr Met Asp Val Trp Gly Lys Gly Thr Thr Val Thr Val Ser Ser
        115                 120                 125
```

<210> SEQ ID NO 120
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 120

```
Glu Asn Ile Gly Tyr Cys Thr Gly Gly Asn Cys Phe Tyr Tyr Tyr
 1               5                  10                  15

Met Asp Val
```

<210> SEQ ID NO 121
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 121

```
Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Val Arg Glu Asn Leu Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
        130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
```

```
                165                 170                 175
Gly Val His Thr Phe Pro Ala Val Leu Gln Ser Ser Gly Leu Tyr Ser
                180                 185                 190

Leu Ser Ser Val Val Thr Val Pro Ser Ser Leu Gly Thr Gln Thr
            195                 200                 205

Tyr Ile Cys Asn Val Asn His Lys Pro Ser Asn Thr Lys Val Asp Lys
        210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
                260                 265                 270

Val Val Val Asp Val Ser His Glu Asp Pro Glu Val Lys Phe Asn Trp
                275                 280                 285

Tyr Val Asp Gly Val Glu Val His Asn Ala Lys Thr Lys Pro Arg Glu
            290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Glu Glu
            355                 360                 365

Met Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
                420                 425                 430

Val Phe Ser Cys Ser Val Met His Glu Ala Leu His Asn His Tyr Thr
            435                 440                 445

Gln Lys Ser Leu Ser Leu Ser Pro Gly Lys
        450                 455

<210> SEQ ID NO 122
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg gctggagtg gtttcatac attagtagta gtggtactac caaatactac      180
gcagactctg tgaagggccg attcaccatc tccagggaca acgccaagaa ctcactgtat     240
ctgcaaatga acagcctgag agccgaggac acggccgtgt attactgtgt gagagagaat     300
ttaggatact gtagtggtgg gagctgcttc tactactact acatggacgt ctggggcaaa     360
```
gggaccacgg tcaccgtctc ctca                                          384

<210> SEQ ID NO 123
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Glu Asn Leu Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125

<210> SEQ ID NO 124
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Asn Leu Gly Tyr Cys Ser Gly Gly Ser Cys Phe Tyr Tyr Tyr Tyr
1               5                   10                  15

Met Asp Val

<210> SEQ ID NO 125
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                 85                  90                  95

Ala Arg Glu Arg Ile Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 126
<211> LENGTH: 384
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 126

```
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg gatttcatac attagtagta gtggtagtac catatactac     180
gcagactctg tgaagggccg attcaccatc tccagggaca acgccaagaa ctcactgtat     240
ctgcaaatga acagcctgag agccgaggac acggccgtgt attactgtgc gagagaacga     300
ataggatact gtagtggtgg gagctgcttc tactactact acatggacgt ctggggcaaa     360
gggaccacgg tcaccgtctc ctca                                            384
```

<210> SEQ ID NO 127
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 127

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125
```

<210> SEQ ID NO 128
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 128

```
Trp Ile Arg Gln Ala Pro Gly Lys Gly Leu Glu Trp Ile Ser
1               5                   10
```

<210> SEQ ID NO 129
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 129

Glu Arg Ile Gly Tyr Cys Ser Gly Gly Ser Cys Phe Tyr Tyr Tyr Tyr

Met Asp Val

<210> SEQ ID NO 130
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 130

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
```

```
                    340                 345                 350
Gln Pro Arg Glu Pro Gln Val Tyr Thr Leu Pro Pro Ser Arg Glu Glu
                355                 360                 365

Met Thr Lys Asn Gln Val Ser Leu Thr Cys Leu Val Lys Gly Phe Tyr
        370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455

<210> SEQ ID NO 131
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccatc tccagggaca acgccaagaa ctcactgtat     240
ctgcaaatga acagcctgag agccgaggac acggccgtgt attactgtgc gagagaacga     300
ataggatact gtagtggtgg gagctgcttc tactactact acatggacgt ctggggcaaa     360
gggaccacgg tcaccgtctc ctca                                            384

<210> SEQ ID NO 132
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Ile Gly Tyr Cys Ser Gly Gly Ser Cys Phe Tyr Tyr
            100                 105                 110
```

Tyr Tyr Met Asp Val Trp Gly Lys Gly Thr Thr Val Thr Val Ser Ser
        115                 120                 125

<210> SEQ ID NO 133
<211> LENGTH: 990
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 133
gcctccacca agggcccatc ggtcttccct ctggcaccct cctccaagag cacctctggg      60
ggcacagcgg ccctgggctg cctggtcaag gactacttcc ccgaaccggt gacggtgtcg     120
tggaactcag cgccctgac cagcggcgtg cacaccttcc cggctgtcct acagtcctca      180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggga     360 ccgtcagtct tcctcttccc cccaaaaccc aaggacaccc tcatgatctc ccggaccct     420 gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctat agcaagctca ccgtggacaa gagcaggtgg     900
cagcagggga acgtcttctc atgctccgtg atgcatgagg ctctgcacaa ccactacacg     960
cagaagagtc tctccctgtc tccgggtaaa                                      990

<210> SEQ ID NO 134
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 134
cgaactgtgg ctgcaccatc tgtcttcatc ttccctccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg c                                               321

<210> SEQ ID NO 135
<211> LENGTH: 312
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135

```
cccaaggctg cccctcggt cactctgttc ccaccctcct ctgaggagct ccaagccaac    60
aaggccacac tggtgtgtct cataagtgac ttctacccgg agccgtgac agtggcctgg   120
aaggcagata gcagccccgt caaggcggga gtggagacca ccacaccctc caaacaaagc  180
aacaacaagt acgcggccag cagctacctg agcctgacgc ctgagcagtg aagtcccac   240
aaaagctaca gctgccaggt cacgcatgaa gggagcaccg tggagaagac agttgcccct  300
acagaatgtt ca                                                      312
```

<210> SEQ ID NO 136
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gln Ser Val Leu Thr Gln Pro Pro Ser Val Ser Gly Ala Pro Gly Gln
1               5                   10                  15

Gly Val Thr Ile Ser Cys
            20

<210> SEQ ID NO 137
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Trp Tyr Gln Gln Leu Pro Gly Ser Ala Pro Lys Phe Phe Ile Tyr
1               5                   10                  15

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Ser Asn Asn Arg Pro Ser
1               5

<210> SEQ ID NO 139
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val

```
                    35                  40                  45
Ser Tyr Ile Ser Ser Ser Gly Thr Thr Lys Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu His Leu Asn Ser Leu Arg Ala Glu Asp Thr Ala Val Tyr Tyr Cys
                 85                  90                  95

Val Arg Glu Asn Leu Gly Tyr Cys Ser Gly Gly Ser Cys Phe Tyr Tyr
                100                 105                 110

Tyr Tyr Met Asp Val Trp Gly Lys Gly Thr Thr Val Thr Val Ser Ser
            115                 120                 125

Ala Ser Thr Lys Gly Pro Ser Val Arg Pro Leu Ala Pro Ser Ser Lys
130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
450                 455
```

-continued

<210> SEQ ID NO 140
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
caggtgcagc tggtggagtc tgggggaggc ttggtcaagc ctggagggtc cctgagactc     60
tcctgtgcag cctctggatt caccttcagt gactactaca tgagctggat ccgccaggct    120
ccagggaagg ggctggagtg ggtttcatac attagtagta gtggtactac caaatactac    180
gcagactctg tgaagggccg attcaccatt tccagggaca acgccaagaa ctcattgtat    240
ctgcatttga acagcctgag agccgaggac acggccgtgt attactgtgt gagagagaat    300
ttaggatact gtagtggtgg gagctgcttc tactactact acatggacgt ctggggcaaa    360
gggaccacgg tcaccgtctc ctca                                            384

<210> SEQ ID NO 141
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu His Leu Asn Ser Leu Arg Ala Glu Asp Thr Ala Val Tyr Tyr Cys
                85                  90                  95

Val Arg Glu Asn Leu Gly Tyr Cys Ser Gly Gly Ser Cys Phe Tyr Tyr
            100                 105                 110

Tyr Tyr Met Asp Val Trp Gly Lys Gly Thr Thr Val Thr Val Ser Ser
        115                 120                 125

<210> SEQ ID NO 142
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Arg Phe Thr Ile Ser Arg Asp Asn Ala Lys Asn Ser Leu Tyr Leu His
1               5                   10                  15

Leu Asn Ser Leu Arg Ala Glu Asp Thr Ala Val Tyr Tyr Cys Val Arg
            20                  25                  30

-continued

```
<210> SEQ ID NO 143
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Lys Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu His Leu Asn Ser Leu Arg Ala Glu Asp Thr Ala Val Tyr Tyr Cys
                85                  90                  95

Val Arg Glu Asn Leu Gly Tyr Cys Ser Gly Ser Cys Phe Tyr Tyr Tyr
            100                 105                 110

Tyr Tyr Met Asp Val Trp Gly Lys Gly Thr Thr Val Thr Val Ser Ser
        115                 120                 125

Ala Ser Thr Lys Gly Pro Ser Val Arg Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Arg Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365
```

```
Met Thr Lys Asn Gln Val Ser Leu Thr Cys Leu Val Lys Gly Phe Tyr
            370                 375                 380
Pro Ser Asp Ile Ala Val Glu Trp Glu Ser Asn Gly Gln Pro Glu Asn
385                 390                 395                 400
Asn Tyr Lys Thr Thr Pro Pro Val Leu Asp Ser Asp Gly Ser Phe Phe
                405                 410                 415
Leu Tyr Ser Lys Leu Thr Val Asp Lys Ser Arg Trp Gln Gln Gly Asn
                420                 425                 430
Val Phe Ser Cys Ser Val Met His Glu Ala Leu His Asn His Tyr Thr
                435                 440                 445
Gln Lys Ser Leu Ser Leu Ser Pro Gly Lys
            450                 455

<210> SEQ ID NO 144
<211> LENGTH: 384
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 144
caggtgcagc tggtggagtc tgggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtactac caaatactac     180
gcagactctg tgaagggccg attcaccatc tccagggaca cgccaagaa ctcactgtat      240 ctgcaaatga acagcctgag agccgaggac acggccgtgt attactgtgc gagagaacga     300
ataggatact gtagtggtgg gagctgcttc tactactact acatggacgt ctggggcaaa     360
gggaccacgg tcaccgtctc ctca                                             384

<210> SEQ ID NO 145
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Gln Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Asp Tyr
            20                  25                  30
Tyr Met Ser Trp Ile Arg Gln Ala Pro Gly Lys Gly Leu Glu Trp Val
        35                  40                  45
Ser Tyr Ile Ser Ser Ser Gly Thr Thr Lys Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu His Leu Asn Ser Leu Arg Ala Glu Asp Thr Ala Val Tyr Tyr Cys
                85                  90                  95
Val Arg Glu Asn Leu Gly Tyr Cys Ser Gly Gly Ser Cys Phe Tyr Tyr
            100                 105                 110
Tyr Tyr Met Asp Val Trp Gly Lys Gly Thr Thr Val Thr Val Ser Ser
        115                 120                 125
```

<210> SEQ ID NO 146
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Thr Pro Phe Thr Phe Gly Pro Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 147
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 147

```
gacatcgtga tgacccagtc tccagactcc ctggctgtgt ctctgggcga gagggccacc    60
atcaactgca agtccagcca gagtgtttta tacagctcca acaataagaa ctacttagct   120
tggtaccagc agaaaccagg acagcctcct aagctgctca tttattgggc atctacccgg   180
gaatccgggg tccctgaccg attcagtggc agcgggtctg ggacagattt cactctcacc   240
atcagcagcc tgcaggctga agatgtggca gtttattact gtcagcaata ttataatact   300
ccattcactt tcggccctgg gaccaaagtg gaaatcaaa                          339
```

<210> SEQ ID NO 148
<211> LENGTH: 113
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 148

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Asn Thr Pro Phe Thr Phe Gly Pro Gly Thr Lys Val Glu Ile
            100                 105                 110

Lys
```

<210> SEQ ID NO 149
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

```
Asp Ile Val Met Thr Gln Ser Pro Asp Ser Leu Ala Val Ser Leu Gly
1               5                   10                  15

Glu Arg Ala Thr Ile Asn Cys
            20
```

<210> SEQ ID NO 150
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

```
Lys Ser Ser Gln Ser Val Leu Tyr Ser Ser Asn Asn Lys Asn Tyr Leu
1               5                   10                  15

Ala
```

<210> SEQ ID NO 151
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

```
Trp Tyr Gln Gln Lys Pro Gly Gln Pro Pro Lys Leu Leu Ile Tyr
1               5                   10                  15
```

<210> SEQ ID NO 152

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Trp Ala Ser Thr Arg Glu Ser
1               5

<210> SEQ ID NO 153
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Gln Tyr Tyr Asn Thr Pro Phe Thr
1               5

<210> SEQ ID NO 155
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Phe Gly Pro Gly Thr Lys Val Glu Ile Lys
1               5                   10

<210> SEQ ID NO 156
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Asn Leu Leu Tyr Asn
            20                  25                  30

Ser Asn Lys Leu Asn Tyr Leu Ser Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60
```

```
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Asn Thr Pro Phe Thr Phe Gly Pro Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220
```

<210> SEQ ID NO 157
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157
gacatcgtga tgacccagtc tccagactcc ctggctgtgt ctctgggcga gagggccacc    60
atcaactgca ggtccagcca gaaccttta tataactcca acaagctgaa ctacttgtct   120
tggtaccagc agaaaccagg acagcctcct aagctgctca tttactgggc atctacccgg   180
gaatccgggg tccctgaccg attcagtggc agcgggtctg ggacagattt cactctcacc   240
atcagcagcc tgcaggctga agatgtggca gtttattact gtcagcaata ttataatact   300
ccattcactt tcggccctgg gaccaaagtg gaaatcaaa                          339

<210> SEQ ID NO 158
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

```
Asp Ile Val Met Thr Gln Ser Pro Asp Ser Leu Ala Val Ser Leu Gly
 1               5                  10                  15

Glu Arg Ala Thr Ile Asn Cys Arg Ser Ser Gln Asn Leu Leu Tyr Asn
            20                  25                  30

Ser Asn Lys Leu Asn Tyr Leu Ser Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
 65                  70                  75                  80
```

Ile Ser Ser Leu Gln Ala Glu Asp Val Ala Val Tyr Tyr Cys Gln Gln
                85                  90                  95

Tyr Tyr Asn Thr Pro Phe Thr Phe Gly Pro Gly Thr Lys Val Glu Ile
            100                 105                 110

Lys

<210> SEQ ID NO 159
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Ser Ser Gln Asn Leu Leu Tyr Asn Ser Asn Lys Leu Asn Tyr Leu
1               5                   10                  15

Ser

<210> SEQ ID NO 160
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Gln Gly Thr Lys Leu Glu Ile
            100                 105                 110

Asn Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220

```
<210> SEQ ID NO 161
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 161
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
ccgttcactt ttggccaggg gaccaaactg gagatcaat                             339

<210> SEQ ID NO 162
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Gln Gly Thr Lys Leu Glu Ile
            100                 105                 110

Asn

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Gln Tyr Tyr Ser Thr Pro Phe Thr
1               5

<210> SEQ ID NO 164
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 164

Phe Gly Gln Gly Thr Lys Leu Glu Ile Asn
1               5                   10

<210> SEQ ID NO 165
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Gln Gly Thr Lys Leu Glu Ile
                100                 105                 110

Asn Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 166
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 166
gacatcgtga tgacccagtc tccatcctca ttctctgcat ctacaggaga cagagtcacc    60
atcacttgtc gggcgagtca gggtattaac agtyatttgg cctggtatca gcaaaaacca   120
gggaaagccc ctaggctcca gatctatgct gcatccactt tgcaaagtgg agtcgcatcg   180
aggttcagcg gcagtggatc tgggacagag ttcactctca ccatcagctc cctgcagtct   240
gaagattttg caacttatta ctgtcaacaa tattatagta ctccgttcac ttttggccag   300
gggaccaaac tggagatcaa tcaa                                          324

<210> SEQ ID NO 167
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Gln Gly Thr Lys Leu Glu Ile
            100                 105                 110

Asn

<210> SEQ ID NO 168
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys Gln Gln
                85                  90                  95

Tyr Tyr Ser Thr Pro Phe Thr Phe Gly Gln Gly Thr Lys Leu Glu Ile
            100                 105                 110

Asn Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 169
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 169
gacatcgtga tgacccagtc tccagactcc ctggctgtgt ctctgggcga gagggccacc      60
atcaactgca agtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca atttattact gtcagcaata ttatagtact     300
ccgttcactt ttggccaggg gaccaaactg gagatcaat                            339

<210> SEQ ID NO 170
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys Gln Gln
                85                  90                  95

Tyr Tyr Ser Thr Pro Phe Thr Phe Gly Gln Gly Thr Lys Leu Glu Ile
            100                 105                 110

Asn

<210> SEQ ID NO 171
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Gly Val Pro Asp Arg Phe Ser Gly Ser Gly Ser Gly Thr Asp Phe Thr
```

```
                1               5                   10                  15
Leu Thr Ile Ser Ser Leu Gln Ala Glu Asp Val Ala Ile Tyr Tyr Cys
                20                  25                  30
```

<210> SEQ ID NO 172
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Tyr Asn Ile Gly Ala Gly
                20                  25                  30

Tyr Asp Val His Trp Tyr Gln Gln Val Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Phe Gly Gly Gly Thr Lys Leu Thr Val Leu
                100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
        130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
                180                 185                 190

Ser His Lys Ser Tyr Ser Cys Gln Val Thr His Glu Gly Ser Thr Val
            195                 200                 205

Glu Lys Thr Val Ala Pro Thr Glu Cys Ser
        210                 215
```

<210> SEQ ID NO 173
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173

```
cagtctgtgc tgacgcagcc gccctcagtg tctggggccc cagggcagag ggtcaccatc        60
tcctgcactg ggagcagtta caacatcggg gcagggtatg atgtccactg gtaccagcag       120
gttccaggaa cagcccccaa actcctcatc tatggtaaca gcaatcggcc ctcaggggtc       180
cctgaccgat tctctggctc caagtctggc acctcagcct ccctggccat cactgggctc       240
caggctgagg atgaggctga ttattactgc cagtcctatg acagcagcct gagtggttca       300
```

```
ggggtattcg gcggagggac caagctgacc gtccta                                336
```

<210> SEQ ID NO 174
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Ser Val Leu Thr Gln Pro Pro Ser Val Ser Gly Ala Pro Gly Gln
1               5                   10                  15

Arg Val Thr Ile Ser Cys Thr Gly Ser Ser Tyr Asn Ile Gly Ala Gly
            20                  25                  30

Tyr Asp Val His Trp Tyr Gln Gln Val Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Phe Gly Gly Gly Thr Lys Leu Thr Val Leu
            100                 105                 110

<210> SEQ ID NO 175
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Ser Val Leu Thr Gln Pro Pro Ser Val Ser Gly Ala Pro Gly Gln
1               5                   10                  15

Arg Val Thr Ile Ser Cys
            20

<210> SEQ ID NO 176
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Thr Gly Ser Ser Tyr Asn Ile Gly Ala Gly Tyr Asp Val His
1               5                   10

<210> SEQ ID NO 177
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Trp Tyr Gln Gln Val Pro Gly Thr Ala Pro Lys Leu Leu Ile Tyr
1               5                   10                  15

```
<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Gly Asn Ser Asn Arg Pro Ser
1               5

<210> SEQ ID NO 179
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gly Val Pro Asp Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Gln Ser Tyr Asp Ser Ser Leu Ser Gly Ser Gly Val
1               5                   10

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Phe Gly Gly Gly Thr Lys Leu Thr Val Leu
1               5                   10

<210> SEQ ID NO 182
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45
```

Leu Ile Tyr Gly Asn Ser Tyr Arg Pro Ser Gly Val Pro Asp Arg Phe
    50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Gly Val Phe Gly Gly Gly Thr Lys Leu Thr Val Leu
                100                 105                 110

Gly Gln Pro Lys Ala Ala Pro Ser Val Thr Leu Phe Pro Pro Ser Ser
                115                 120                 125

Glu Glu Leu Gln Ala Asn Lys Ala Thr Leu Val Cys Leu Ile Ser Asp
130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
                180                 185                 190

Ser His Lys Ser Tyr Ser Cys Gln Val Thr His Glu Gly Ser Thr Val
                195                 200                 205

Glu Lys Thr Val Ala Pro Thr Glu Cys Ser
210                 215

<210> SEQ ID NO 183
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 183
cagtctgtgc tgacgcagcc gccctcagtg tctggggccc cagggcagag ggtcaccatc     60
tcctgcactg ggagcagctc caacatcggg gcaggttatg atgtacactg gtaccagcag    120
cttcctggaa cagcccccaa actcctcatc tatggtaata gttatcggcc ctcaggggtc    180
cctgaccgat tctctggctc caagtctggc acctcagcct ccctggccat tactgggctc    240
caggctgagg atgaggctga ttattactgc cagtcctatg acagcagcct gagtggttca    300
ggggtattcg gcggagggac caagctgacc gtccta                              336

<210> SEQ ID NO 184
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
                 35                  40                  45

Leu Ile Tyr Gly Asn Ser Tyr Arg Pro Ser Gly Val Pro Asp Arg Phe
    50                  55                  60

```
Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Gly Val Phe Gly Gly Gly Thr Lys Leu Thr Val Leu
            100                 105                 110

<210> SEQ ID NO 185
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Thr Gly Ser Ser Ser Asn Ile Gly Ala Gly Tyr Asp Val His
1               5                   10

<210> SEQ ID NO 186
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Trp Tyr Gln Gln Leu Pro Gly Thr Ala Pro Lys Leu Leu Ile Tyr
1               5                   10                  15

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Gly Asn Ser Tyr Arg Pro Ser
1               5

<210> SEQ ID NO 188
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gln Ser Val Leu Thr Gln Pro Pro Ser Val Ser Gly Ala Pro Gly Gln
1               5                   10                  15

Gly Val Thr Ile Ser Cys Thr Gly Ser Ser Ser Asn Ile Gly Ala Gly
                 20                  25                  30

Tyr Asp Val His Trp Tyr Gln Gln Leu Pro Gly Ser Ala Pro Lys Phe
             35                  40                  45

Phe Ile Tyr Gly Ser Asn Asn Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95
```

Leu Ser Gly Ser Gly Val Phe Gly Gly Gly Thr Lys Leu Thr Val Leu
            100                 105                 110

Gly Gln Pro Lys Ala Ala Pro Ser Val Thr Leu Phe Pro Pro Ser Ser
            115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175

Lys Tyr Ala Ala Ser Ser Tyr Leu Ser Leu Thr Pro Glu Gln Trp Lys
            180                 185                 190

Ser His Lys Ser Tyr Ser Cys Gln Val Thr His Glu Gly Ser Thr Val
            195                 200                 205

Glu Lys Thr Val Ala Pro Thr Glu Cys Ser
    210                 215

<210> SEQ ID NO 189
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 189
cagtctgtgc tgacgcagcc gccctcagtg tctggggccc cagggcaggg ggtcaccatc     60
tcctgcactg ggagcagctc aacatcgggg gcaggttatg atgtacactg gtaccagcag    120
cttccaggat cagcccccaa attcttcatc tatggtagca acaatcggcc ctcagggggtc   180 cctgaccgat tctctggctc caagtctggc acctcagcct ccctggccat cactgggctc    240
caggctgagg atgaggctga ttattactgc cagtcctatg acagcagcct gagtggttca    300
ggggtattcg gcggagggac caagctgacc gtccta                              336

<210> SEQ ID NO 190
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Gln Ser Val Leu Thr Gln Pro Pro Ser Val Ser Gly Ala Pro Gly Gln
1               5                   10                  15

Gly Val Thr Ile Ser Cys Thr Gly Ser Ser Asn Ile Gly Ala Gly
            20                  25                  30

Tyr Asp Val His Trp Tyr Gln Gln Leu Pro Gly Ser Ala Pro Lys Phe
            35                  40                  45

Phe Ile Tyr Gly Ser Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Gly Val Phe Gly Gly Gly Thr Lys Leu Thr Val Leu
            100                 105                 110

<210> SEQ ID NO 191
<211> LENGTH: 219
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 191

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Phe Ala Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Glu Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 192
<211> LENGTH: 336
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 192
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttcgcttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactcct     300
gaggctttcg gcggagggac caaggtggag atcaaa                                336

<210> SEQ ID NO 193

```
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193
```

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Phe Ala Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Glu Ala Phe Gly Gly Gly Thr Lys Val Glu Ile Lys
            100                 105                 110

```
<210> SEQ ID NO 194
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194
```

Asp Ile Val Met Thr Gln Ser Pro Leu Ser Leu Pro Val Thr Pro Gly
1               5                   10                  15

Glu Pro Ala Ser Ile Ser Cys
            20

```
<210> SEQ ID NO 195
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195
```

Arg Ser Ser Gln Ser Leu Leu His Ser Asn Gly Tyr Asn Tyr Leu Asp
1               5                   10                  15

```
<210> SEQ ID NO 196
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196
```

Trp Tyr Leu Gln Lys Pro Gly Gln Ser Pro Gln Leu Leu Ile Tyr
1               5                   10                  15

```
<210> SEQ ID NO 197
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 197

Phe Ala Ser Asn Arg Ala Ser
1               5

<210> SEQ ID NO 198
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Met Gln Ala Leu Gln Thr Pro Glu Ala
1               5

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Phe Gly Gly Gly Thr Lys Val Glu Ile Lys
1               5                   10

<210> SEQ ID NO 201
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile

```
                65                  70                  75                  80
Ser Arg Val Glu Ala Glu Asp Val Gly Val Tyr Tyr Cys Met Gln Ala
                    85                  90                  95

Leu Gln Thr Pro Glu Ala Phe Gly Gly Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
210                 215
```

```
<210> SEQ ID NO 202
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 202
gatattgtga tgactcagtc tccactctcc ctgcccgtca cccctggaga gccggcctcc      60
atctcctgca ggtctagtca gagcctcctg tatagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagatttac actgaaaatc     240 agcagagtgg aggctgagga tgttggggtt tattactgca tgcaagctct acaaactcct    300
gaggctttcg gcggagggac caaggtggag atcaaa                              336
```

```
<210> SEQ ID NO 203
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
```

```
                    85                  90                  95
Leu Gln Thr Pro Glu Ala Phe Gly Gly Gly Thr Lys Val Glu Ile Lys
                100                 105                 110

<210> SEQ ID NO 204
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Arg Ser Ser Gln Ser Leu Leu Tyr Ser Asn Gly Tyr Asn Tyr Leu Asp
1               5                   10                  15

<210> SEQ ID NO 205
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Leu Gly Ser Asn Arg Ala Ser
1               5

<210> SEQ ID NO 206
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Glu Ala Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 207
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 207
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300
gaggctttcg gcggagggac caaggtggag atcaaa                               336

<210> SEQ ID NO 208
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Glu Ala Phe Gly Gly Gly Thr Lys Val Glu Ile Lys
            100                 105                 110

<210> SEQ ID NO 209
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Asp Ile Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Ala His Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Glu Ala Phe Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 210
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 210
gatattgtga tgactcagtc tccactctcc ctgcccgtca cccctggaga gccggcctcc      60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggcg cacattttac actgaaaatc    240
agcagagtgg aggctgagga tgttggggtt tactactgca tgcaagctct acaaactcct    300
gaggctttcg gcggagggac caaggtggag atcaaa                              336

<210> SEQ ID NO 211
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
                 20                  25                  30

Asn Gly Tyr Asn Tyr Leu Asp Trp Tyr Leu Gln Lys Pro Gly Gln Ser
            35                  40                  45

```
Pro Gln Leu Leu Ile Tyr Leu Gly Ser Asn Arg Ala Ser Gly Val Pro
        50                  55                  60

Asp Arg Phe Ser Gly Ser Gly Ser Gly Ala His Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Glu Ala Phe Gly Gly Thr Lys Val Glu Ile Lys
                100                 105                 110
```

<210> SEQ ID NO 212
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

```
Gly Val Pro Asp Arg Phe Ser Gly Ser Gly Ser Gly Ala His Phe Thr
 1               5                  10                  15

Leu Lys Ile Ser Arg Val Glu Ala Glu Asp Val Gly Val Tyr Tyr Cys
             20                  25                  30
```

<210> SEQ ID NO 213
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Tyr
             20                  25                  30

Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asp Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Glu Ala Phe Gly Gly Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

Pro Val Thr Lys Ser Phe Asn Arg Gly Glu Cys
    210                 215

<210> SEQ ID NO 214
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 214
gatattgtga tgactcagtc tccactctcc ctgcccgtca cccctggaga gccggcctcc      60
atctcgtgca ggtctagtca gagcctcctg cattataatg gatacaacta tttggattgg    120
tacctgcaga agccagggca gtctccacaa ctcctgatct atttgggttc tgatcgggcc    180
tccggggtcc ctgacaggtt cagtggcagt ggatcaggca cagattttac actgaaaatc    240
agcagagtgg aggctgagga tgttgggggtt tattactgca tgcaagctct acaaactcct    300
gaggctttcg gcggagggac caaggtggag atcaaa                              336

<210> SEQ ID NO 215
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Tyr
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asp Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Glu Ala Phe Gly Gly Gly Thr Lys Val Glu Ile Lys
            100                 105                 110

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Arg Ser Ser Gln Ser Leu Leu His Tyr Asn Gly Tyr Asn Tyr Leu Asp
1               5                   10                  15

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 217

Leu Gly Ser Asp Arg Ala Ser
1               5

<210> SEQ ID NO 218
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Glu Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 219
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 219
gatattgtga tgactcagtc tccactctcc ctgcccgtca cccctggaga gccggcctcc      60
atctcgtgca ggtctagtca gagcctcctg cattataatg gatacaacta tttggattgg     120
tacctgcaga agccagggca gtctccacaa ctcctgatct atttgggttc tgatcgggcc     180
tccggggtcc ctgacaggtt cagtggcagt ggatcaggca cagattttac actgaaaatc     240

```
agcagagtgg aggctgagga tgttggggtt tattactgca tgcaagctct acaaactcct    300
gaggctttcg gcggagggac caaggtggag atcaaa                              336
```

<210> SEQ ID NO 220
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Glu Thr Phe Gly Gln Gly Thr Lys Val Glu Ile Lys
            100                 105                 110
```

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

```
Met Gln Ala Leu Gln Thr Pro Glu Thr
1               5
```

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

```
Phe Gly Gln Gly Thr Lys Val Glu Ile Lys
1               5                   10
```

<210> SEQ ID NO 223
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
```

```
            20                  25                  30
Asn Gly Tyr Asn Tyr Leu Asp Trp Tyr Leu Gln Lys Pro Gly Gln Ser
         35                  40                  45

Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Gln Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 224
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 224

```
gatattgtga tgactcagtc tccactctcc ctgcccgtca cccctggaga gccggcctcc    60
atctcctgca ggtctagtca gagcctcctg catagtaatg gatacaacta tttggattgg   120
tacctgcaga agccagggca gtctccacag ctcctgatct atttgggttc taatcgggcc   180
tccggggtcc ctgacaggtt cagtggcagt ggatcaggca cagattttac actgaaaatc   240
agcagagtgg aggctgagga tgttggggtt tattactgca tgcaagctct acaaactcct   300 cagactttg gccaagggac caaggtggaa atcaaa                              336
```

<210> SEQ ID NO 225
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ser
             20                  25                  30

Asn Gly Tyr Asn Tyr Leu Asp Trp Tyr Leu Gln Lys Pro Gly Gln Ser
```

```
                35                  40                  45
Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Leu Gln Thr Pro Gln Thr Phe Gly Gln Gly Thr Lys Val Glu Ile Lys
                100                 105                 110
```

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

```
Met Gln Ala Leu Gln Thr Pro Gln Thr
 1               5
```

<210> SEQ ID NO 227
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Leu His Ile
                 20                  25                  30

Asn Gly Tyr Lys Tyr Leu Asp Trp Tyr Leu Gln Lys Pro Gly Gln Ser
                35                  40                  45

Pro Gln Leu Leu Ile Tyr Leu Gly Ser Asn Arg Ala Ser Gly Val Pro
     50                  55                  60

Asp Arg Phe Ser Ala Ser Gly Ser Gly Thr Asp Phe Thr Leu Gln Ile
 65                  70                  75                  80

Ser Arg Val Glu Ala Glu Asp Val Gly Val Tyr Tyr Cys Met Gln Ala
                 85                  90                  95

Leu Gln Thr Pro Gln Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
            210                 215
```

<210> SEQ ID NO 228
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 228
gatattgtga tgactcagtc tccactctcc ctgcccgtca cccctggaga gccggcctcc       60
atctcctgca ggtccagtca gagcctcctg catattaatg gatacaagta tttggattgg     120
tacctgcaga agccagggca gtctccacag ctcctcatct atttgggttc taatcgggcc     180
tccggggtcc ctgacaggtt cagtgccagt ggatcaggca cagattttac actgcaaatc     240
agcagagtgg aggctgagga tgttggggtt tattactgca tgcaagctct acaaactcct     300 cagactttg gccaagggac caaggtggaa atcaaa                                336

<210> SEQ ID NO 229
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ile
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Ala Ser Gly Ser Gly Thr Asp Phe Thr Leu Gln Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Val Glu Ile Lys
            100                 105                 110

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Arg Ser Ser Gln Ser Leu Leu His Ile Asn Gly Tyr Lys Tyr Leu Asp
1               5                   10                  15

<210> SEQ ID NO 231
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Gly Val Pro Asp Arg Phe Ser Ala Ser Gly Ser Gly Thr Asp Phe Thr
1               5                   10                  15

Leu Gln Ile Ser Arg Val Glu Ala Glu Asp Val Gly Val Tyr Tyr Cys
            20                  25                  30

<210> SEQ ID NO 232
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Asp Ile Val Met Thr Gln Ser Pro Leu Ser Leu Pro Val Thr Pro Gly
1               5                   10                  15

Glu Ser Ala Ser Ile Ser Cys Arg Ser Ser Gln Arg Leu Leu Ser Ser
            20                  25                  30

Ser Gly Asn Asn Tyr Leu Asp Trp Tyr Leu Gln Lys Pro Gly Gln Ser
        35                  40                  45

Pro Gln Leu Leu Ile Ser Leu Ala Ser Asn Arg Ala Ser Gly Val Pro
    50                  55                  60

Asp Arg Phe Ser Gly Ser Gly Ser Gly Thr Asp Phe Lys Leu Glu Ile
65                  70                  75                  80

Ser Arg Val Glu Ala Glu Asp Val Gly Ile Tyr Tyr Cys Met Gln Ala
                85                  90                  95

Leu Gln Thr Pro Gln Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 233
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 233
gatattgtga tgactcagtc tccactctcc ctgcccgtca cccctggaga gtcggcctcc     60
atctcctgca ggtctagtca gaggctccta tctagcagtg gaacaattat tttggattgg    120
tacctgcaga agccagggca gtctccacaa ctcctgatct ctttggcttc taatcgggcc    180

```
tccggggtcc ctgacaggtt cagtggcagt ggatcaggca cagattttaa actggaaatc    240
agcagagtgg aggctgagga tgttgggatt tattactgca tgcaagctct acaaactcct    300 cagactttg gccaagggac caaggtggaa atcaaa                               336
```

<210> SEQ ID NO 234
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

```
Asp Ile Val Met Thr Gln Ser Pro Leu Ser Leu Pro Val Thr Pro Gly
1               5                   10                  15

Glu Ser Ala Ser Ile Ser Cys Arg Ser Ser Gln Arg Leu Leu Ser Ser
            20                  25                  30

Ser Gly Asn Asn Tyr Leu Asp Trp Tyr Leu Gln Lys Pro Gly Gln Ser
        35                  40                  45

Pro Gln Leu Leu Ile Ser Leu Ala Ser Asn Arg Ala Ser Gly Val Pro
    50                  55                  60

Asp Arg Phe Ser Gly Ser Gly Ser Gly Thr Asp Phe Lys Leu Glu Ile
65                  70                  75                  80

Ser Arg Val Glu Ala Glu Asp Val Gly Ile Tyr Tyr Cys Met Gln Ala
                85                  90                  95

Leu Gln Thr Pro Gln Thr Phe Gly Gln Gly Thr Lys Val Glu Ile Lys
            100                 105                 110
```

<210> SEQ ID NO 235
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

```
Asp Ile Val Met Thr Gln Ser Pro Leu Ser Leu Pro Val Thr Pro Gly
1               5                   10                  15

Glu Ser Ala Ser Ile Ser Cys
            20
```

<210> SEQ ID NO 236
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

```
Arg Ser Ser Gln Arg Leu Leu Ser Ser Gly Asn Asn Tyr Leu Asp
1               5                   10                  15
```

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

```
Trp Tyr Leu Gln Lys Pro Gly Gln Ser Pro Gln Leu Leu Ile Ser
1               5                   10                  15
```

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

```
Leu Ala Ser Asn Arg Ala Ser
1               5
```

<210> SEQ ID NO 239
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

```
Gly Val Pro Asp Arg Phe Ser Gly Ser Gly Ser Gly Thr Asp Phe Lys
1               5                   10                  15

Leu Glu Ile Ser Arg Val Glu Ala Glu Asp Val Gly Ile Tyr Tyr Cys
                20                  25                  30
```

<210> SEQ ID NO 240
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
                20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 241
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 241

```
gatattgtga tgactcagtc tccactctcc ctgcccgtca cccctggaga gccggcctcc      60
atctcctgca ggtctagtca gagcctcctc catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcaagctct acaaactcct    300 cagactttg gccaggggac caagctggag atcaaa                               336
```

<210> SEQ ID NO 242
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Leu Glu Ile Lys
            100                 105                 110
```

<210> SEQ ID NO 243
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

```
Phe Gly Gln Gly Thr Lys Leu Glu Ile Lys
1               5                   10
```

<210> SEQ ID NO 244
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 244

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 245
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 245
gatattgtga tgactcagtc tccactctcc ctgcccgtca cccctggaga gccggcctcc      60
atctcctgca ggtctagtca gagcctcctg catagtaatg gatacaagta tttggattgg     120
tacctgcaga agccggggca gtctccacag ctcctgatct atttgggttc taatcgggcc     180
tccggggtcc ctgacaggtt cagtggcagt ggatcaggca cagattttac actgaaaatc     240
agcagagtgg aggctgagga tgttggggtt tattactgca tgcaagctct acaaactcct     300
cagacttttg gccaggggac caagctggag atcaaa                               336

<210> SEQ ID NO 246
<211> LENGTH: 112
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 246

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Leu Glu Ile Lys
            100                 105                 110

<210> SEQ ID NO 247
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Arg Ser Ser Gln Ser Leu Leu His Ser Asn Gly Tyr Lys Tyr Leu Asp
1               5                   10                  15

<210> SEQ ID NO 248
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
        180                 185                 190

Lys His Lys Val Tyr Ala Cys Glu Val Thr His Gln Gly Leu Ser Ser
    195                 200                 205

Pro Val Thr Lys Ser Phe Asn Arg Gly Glu Cys
    210                 215

<210> SEQ ID NO 249
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 249
gatattgtga tgactcagtc tccactctcc ctgcccgtca cccctggaga gccggcctcc   60
atctcctgca ggtctagtca gagcctcctg catagtaatg gatacaactt tttggattgg  120
tacctgcaga agccagggca gtctccacag gtcctgatct atttgggttc taatcgggcc  180
tccggggtcc ctgacaggtt cagtggcagt ggatcaggca cagattttac actgaaaatc  240
agcagagtgg aggctgagga tgttggggtt tattactgca tgcaagctct acaaactcct  300 cagactttg gccaggggac caagctggag atcaaa                            336

<210> SEQ ID NO 250
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Phe Leu Asp Trp Tyr Leu Gln Lys Pro Gly Gln Ser
        35                  40                  45

Pro Gln Val Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gln Thr Phe Gly Gln Gly Thr Lys Leu Glu Ile Lys
            100                 105                 110

<210> SEQ ID NO 251
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 251

Arg Ser Ser Gln Ser Leu Leu His Ser Asn Gly Tyr Asn Phe Leu Asp
1               5                   10                  15

<210> SEQ ID NO 252
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Trp Tyr Leu Gln Lys Pro Gly Gln Ser Pro Gln Val Leu Ile Tyr
1               5                   10                  15

<210> SEQ ID NO 253
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Asp Ile Val Met Thr Gln Ser Pro Leu Ser Leu Pro Ala Thr Pro Gly
1               5                   10                  15

Glu Pro Ala Ser Ile Ser Cys Arg Ser Ser Gln Ser Leu Leu His Ser
                20                  25                  30

Asn Gly Tyr Thr Tyr Leu Asp Trp Tyr Leu Gln Lys Pro Gly Gln Ser
            35                  40                  45

Pro Gln Val Leu Ile Tyr Leu Ala Ser Asn Arg Ala Ser Gly Val Pro
        50                  55                  60

Asp Arg Phe Ser Gly Ser Gly Ser Gly Thr Asn Phe Thr Leu Lys Ile
65                  70                  75                  80

Ser Arg Val Glu Ala Glu Asp Val Gly Leu Phe Tyr Cys Met Gln Ala
                85                  90                  95

Leu Gln Thr Pro Gln Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 254
<211> LENGTH: 336
<212> TYPE: DNA
<213> ORGANISM: Artificial Sequence
<220> FEATURE:

<223> OTHER INFORMATION: Description of Artificial Sequence: Synthetic
    polynucleotide

<400> SEQUENCE: 254

```
gatattgtga tgactcagtc tccactctcc ctgcccgcca cccctggaga gccggcctcc      60
atctcctgca ggtctagtca gagcctcctg catagtaatg gatacaccta tttggattgg     120
tacctgcaga agccagggca gtctccacag gtcctgatct atttggcttc taatcgggcc     180
tccggggtcc ctgacaggtt cagtggcagt ggatcaggca caattttac actgaaaatc      240
agcagagtgg aggctgagga tgttggactt ttttactgca tgcaagctct acaaactcct     300
cagacttttg gccaggggac caagctggag atcaaa                               336
```

<210> SEQ ID NO 255
<211> LENGTH: 112
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 255

```
Asp Ile Val Met Thr Gln Ser Pro Leu Ser Leu Pro Ala Thr Pro Gly
1               5                   10                  15
Glu Pro Ala Ser Ile Ser Cys Arg Ser Ser Gln Ser Leu Leu His Ser
            20                  25                  30
Asn Gly Tyr Thr Tyr Leu Asp Trp Tyr Leu Gln Lys Pro Gly Gln Ser
        35                  40                  45
Pro Gln Val Leu Ile Tyr Leu Ala Ser Asn Arg Ala Ser Gly Val Pro
    50                  55                  60
Asp Arg Phe Ser Gly Ser Gly Ser Gly Thr Asn Phe Thr Leu Lys Ile
65                  70                  75                  80
Ser Arg Val Glu Ala Glu Asp Val Gly Leu Phe Tyr Cys Met Gln Ala
                85                  90                  95
Leu Gln Thr Pro Gln Thr Phe Gly Gln Gly Thr Lys Leu Glu Ile Lys
            100                 105                 110
```

<210> SEQ ID NO 256
<211> LENGTH: 23
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 256

```
Asp Ile Val Met Thr Gln Ser Pro Leu Ser Leu Pro Ala Thr Pro Gly
1               5                   10                  15
Glu Pro Ala Ser Ile Ser Cys
            20
```

<210> SEQ ID NO 257
<211> LENGTH: 16
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 257

```
Arg Ser Ser Gln Ser Leu Leu His Ser Asn Gly Tyr Thr Tyr Leu Asp
1               5                   10                  15
```

<210> SEQ ID NO 258
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gly Val Pro Asp Arg Phe Ser Gly Ser Gly Ser Gly Thr Asn Phe Thr
1               5                   10                  15

Leu Lys Ile Ser Arg Val Glu Ala Glu Asp Val Gly Leu Phe Tyr Cys
            20                  25                  30

<210> SEQ ID NO 259
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 260
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 260

```
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttcct     300
ctcactttcg gcggagggac caaggtggag atcaaa                               336
```

<210> SEQ ID NO 261
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Leu Thr Phe Gly Gly Gly Thr Lys Val Glu Ile Lys
            100                 105                 110
```

<210> SEQ ID NO 262
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

```
Asp Ile Val Met Thr Gln Thr Pro Leu Ser Ser Pro Val Thr Leu Gly
1               5                   10                  15

Gln Pro Ala Ser Ile Ser Cys
            20
```

<210> SEQ ID NO 263
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

```
Arg Ser Ser Gln Ser Leu Val His Ser Asp Gly Asn Thr Tyr Leu Ser
1               5                   10                  15
```

```
<210> SEQ ID NO 264
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Trp Leu Gln Gln Arg Pro Gly Gln Pro Pro Arg Leu Leu Ile Tyr
1               5                   10                  15

<210> SEQ ID NO 265
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Lys Ile Ser Asn Arg Phe Ser
1               5

<210> SEQ ID NO 266
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 267
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Met Gln Ala Thr Gln Phe Pro Leu Thr
1               5

<210> SEQ ID NO 268
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
```

```
Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Thr Gln Ala
                 85                  90                  95

Thr Gln Phe Pro Ile Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 269
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 269
gatattgtga tgacccagac tccactctcc tcacctgtca cccttggaca gccggcctcc      60
atctcctgca ggtctagtca agcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca cgcaagctac acaatttccc     300
atcactttcg gccctgggac caaagtggat atcaaa                              336

<210> SEQ ID NO 270
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Asp Ile Val Met Thr Gln Thr Pro Leu Ser Ser Pro Val Thr Leu Gly
  1               5                  10                  15

Gln Pro Ala Ser Ile Ser Cys Arg Ser Ser Gln Ser Leu Val His Ser
             20                  25                  30

Asp Gly Asn Thr Tyr Leu Ser Trp Leu Gln Gln Arg Pro Gly Gln Pro
         35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
```

```
                65                  70                  75                  80
Ser Arg Val Glu Ala Glu Asp Val Gly Val Tyr Tyr Cys Thr Gln Ala
                    85                  90                  95

Thr Gln Phe Pro Ile Thr Phe Gly Pro Gly Thr Lys Val Asp Ile Lys
            100                 105                 110

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Thr Gln Ala Thr Gln Phe Pro Ile Thr
1               5

<210> SEQ ID NO 272
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Phe Gly Pro Gly Thr Lys Val Asp Ile Lys
1               5                   10

<210> SEQ ID NO 273
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175
```

```
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 274
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 274

```
gatattgtga tgacccagac tccactctcc tcacctgtca cccttggaca gccggcctcc      60
atctcctgca ggtctagtca aagcctcgta cacagtgatg aaacaccta cttgagttgg     120 cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca cgcaagctac acaattcccc    300
ctcactttcg gcggagggac caaggtggag atcaaa                              336
```

<210> SEQ ID NO 275
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro Leu Thr Phe Gly Gly Gly Thr Lys Val Glu Ile Lys
            100                 105                 110
```

<210> SEQ ID NO 276
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

```
Thr Gln Ala Thr Gln Phe Pro Leu Thr
1               5
```

<210> SEQ ID NO 277
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 277

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Arg Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 278
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 278

```
gatattgtga tgacccagac tccactctcc tcacctgtca cccttggaca gccggcctcc     60
atctcctgca ggtctagtca agcctcgta cacagtgatg gaaacaccta cttgagttgg    120
cttcagcaga ggccaggcca gcctccaaga ctcctaattt ataagatttc taaccggttc    180
tctggggtcc cagacagatt cagaggcagt ggggcaggga cagatttcac actgaaaatc    240
agcagggtgg aagctgagga tgtcggggtt tattactgca cgcaagctac acaattcccc    300
ctcactttcg gcggagggac caaggtggag atcaaa                              336
```

<210> SEQ ID NO 279
<211> LENGTH: 112

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

Asp Ile Val Met Thr Gln Thr Pro Leu Ser Ser Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Arg Gly Ser Gly Ala Gly Thr Asp Phe Thr Leu Lys Ile
65                  70                  75                  80

Ser Arg Val Glu Ala Glu Asp Val Gly Val Tyr Tyr Cys Thr Gln Ala
                85                  90                  95

Thr Gln Phe Pro Leu Thr Phe Gly Gly Gly Thr Lys Val Glu Ile Lys
            100                 105                 110

<210> SEQ ID NO 280
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Gly Val Pro Asp Arg Phe Arg Gly Ser Gly Ala Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 281
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Thr Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu 115                 120                 125
Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 282
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 282
gatgttgtga tgactcagtc tccactctcc ctgcccgtca cccttggaca gccggcctcc      60
atctcctgca ggtctagtca aagcctcgta tacagtgatg gaaacaccta cttgaattgg     120
tttcagcaga ggccaggcca atctccaagg cgcctaattt atacggtttc taaccgggac     180
tctggggtcc cagacagatt cagcggcagt gggtcaggca ctgatttcac actgaaaatc     240
agcagggtgg aggctgagga tgttggggtt tattactgca tgcaaggtac acactggcct     300
tggacgttcg gccaagggac caaggtggaa atcaaa                               336

<210> SEQ ID NO 283
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Thr Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Ile Lys
            100                 105                 110

<210> SEQ ID NO 284
<211> LENGTH: 23
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 284

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 285
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Arg Ser Ser Gln Ser Leu Val Tyr Ser Asp Gly Asn Thr Tyr Leu Asn
1               5                   10                  15

<210> SEQ ID NO 286
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Trp Phe Gln Gln Arg Pro Gly Gln Ser Pro Arg Arg Leu Ile Tyr
1               5                   10                  15

<210> SEQ ID NO 287
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Thr Val Ser Asn Arg Asp Ser
1               5

<210> SEQ ID NO 288
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Met Gln Gly Thr His Trp Pro Trp Thr
1               5

<210> SEQ ID NO 289
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289
```

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Ala Asn Arg Tyr Leu Asn Trp Phe Gln Gln Arg Pro Gly Gln Ser
        35                  40                  45

Pro Arg Arg Leu Ile Tyr Lys Val Ser Arg Asp Ser Gly Val Pro
    50                  55                  60

Asp Arg Phe Ser Gly Ser Gly Ser Asp Thr Asp Phe Thr Leu Lys Ile
65                  70                  75                  80

Ser Arg Val Glu Ala Glu Asp Val Gly Val Cys Asp Cys Met Gln Gly
                85                  90                  95

Thr His Trp Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 290
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 290
gatgttgtga tgactcagtc tccactctcc ctgcccgtca cccttggaca gccggcctcc      60
atctcctgca ggtctagtca aagcctcgta tacagtgatg caaacaggta cttgaattgg     120
tttcagcaga ggccaggcca atctccaagg cgcctaattt ataaggtttc tagcagggac     180
tctggggtcc cagacagatt cagcggcagt gggtcagaca ctgacttcac actgaagatc     240
agcagggtgg aggctgagga tgttggggtt tgtgactgca tgcaaggtac acactggcct     300
tggacgttcg gccaagggac caaggtggaa atcaaa                               336

<210> SEQ ID NO 291
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Ala Asn Arg Tyr Leu Asn Trp Phe Gln Gln Arg Pro Gly Gln Ser
            35                  40                  45

Pro Arg Arg Leu Ile Tyr Lys Val Ser Ser Arg Asp Ser Gly Val Pro
    50                  55                  60

Asp Arg Phe Ser Gly Ser Gly Ser Asp Thr Asp Phe Thr Leu Lys Ile
65                  70                  75                  80

Ser Arg Val Glu Ala Glu Asp Val Gly Val Cys Asp Cys Met Gln Gly
                85                  90                  95

Thr His Trp Pro Trp Thr Phe Gly Gln Gly Thr Lys Val Glu Ile Lys
            100                 105                 110

<210> SEQ ID NO 292
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Ser Ser Gln Ser Leu Val Tyr Ser Asp Ala Asn Arg Tyr Leu Asn
1               5                   10                  15

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Lys Val Ser Ser Arg Asp Ser
1               5

<210> SEQ ID NO 294
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 294

Gly Val Pro Asp Arg Phe Ser Gly Ser Gly Ser Asp Thr Asp Phe Thr
1               5                   10                  15

Leu Lys Ile Ser Arg Val Glu Ala Glu Asp Val Gly Val Cys Asp Cys
                20                  25                  30

<210> SEQ ID NO 295
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser

```
                    20                  25                  30

Asn Ala Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Val Tyr Tyr Cys Met Gln Gly
                 85                  90                  95

Thr His Trp Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 296
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 296
gatgttgtga tgactcagtc tccactctcc ctgcccgtca cccctggaga gccggcctcc     60
atctcctgca ggtctagtca gagcctcctg catagtaacg catacaacta tttggattgg    120
tacctgcaga agccagggca gtctccacag ctcctgatct atttgggttc taatcgggcc    180
tccggggtcc ctgacaggtt cagtggcagt ggatctggca cagactttac actgaaaatc    240
agcagagtgg aggctgacga tgttggggtt tattactgca tgcaaggtac acactggcct    300
tggacgttcg gccaagggac caaggtggaa atcaaa                              336

<210> SEQ ID NO 297
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Asp Val Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
             20                  25                  30

Asn Ala Tyr Asn Tyr Leu Asp Trp Tyr Leu Gln Lys Pro Gly Gln Ser
```

```
                35                  40                  45
Pro Gln Leu Leu Ile Tyr Leu Gly Ser Asn Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Val Tyr Tyr Cys Met Gln Gly
                 85                  90                  95

Thr His Trp Pro Trp Thr Phe Gly Gln Gly Thr Lys Val Glu Ile Lys
            100                 105                 110

<210> SEQ ID NO 298
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Asp Val Val Met Thr Gln Ser Pro Leu Ser Leu Pro Val Thr Pro Gly
 1               5                  10                  15

Glu Pro Ala Ser Ile Ser Cys
             20

<210> SEQ ID NO 299
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Arg Ser Ser Gln Ser Leu Leu His Ser Asn Ala Tyr Asn Tyr Leu Asp
 1               5                  10                  15

<210> SEQ ID NO 300
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

Gly Val Pro Asp Arg Phe Ser Gly Ser Gly Ser Gly Thr Asp Phe Thr
 1               5                  10                  15

Leu Lys Ile Ser Arg Val Glu Ala Asp Asp Val Gly Val Tyr Tyr Cys
             20                  25                  30

<210> SEQ ID NO 301
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30
```

```
Asp Gly Asn Thr Tyr Leu Asn Trp Phe Gln Gln Arg Pro Gly Gln Ser
            35                  40                  45

Pro Arg Arg Leu Ile Tyr Gln Val Ser Asn Arg Asp Ser Gly Val Pro
 50                  55                  60

Asp Arg Phe Ser Gly Ser Gly Ser Gly Thr Asp Phe Thr Leu Lys Ile
 65                  70                  75                  80

Gly Arg Val Glu Ala Glu Asp Val Gly Val Tyr Phe Cys Met Gln Gly
                 85                  90                  95

Thr His Trp Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 302
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 302

```
gatgttgtga tgactcagtc tccactctcc ctgcccgtca cccttggaca gccggcctcc    60
atctcctgca ggtctagtca aagcctcgta tacagtgatg gaaacaccta cttgaattgg   120
tttcagcaga ggccaggcca atctccaagg cgcctcattt atcaggtttc taaccgggac   180
tctggggtcc cagacagatt cagcggcagt gggtcaggca ctgatttcac actgaaaatc   240
ggcagggtgg aggctgagga tgttggggtt tattttgca tgcaaggtac acactggcct   300
tggacgttcg gccaagggac caaggtggaa atcaaa                             336
```

<210> SEQ ID NO 303
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 303

```
Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Leu Val Tyr Ser
             20                  25                  30

Asp Gly Asn Thr Tyr Leu Asn Trp Phe Gln Gln Arg Pro Gly Gln Ser
         35                      40                  45
```

```
Pro Arg Arg Leu Ile Tyr Gln Val Ser Asn Arg Asp Ser Gly Val Pro
        50                  55                  60
Asp Arg Phe Ser Gly Ser Gly Ser Gly Thr Asp Phe Thr Leu Lys Ile
 65                  70                  75                  80
Gly Arg Val Glu Ala Glu Asp Val Gly Val Tyr Phe Cys Met Gln Gly
                85                  90                  95
Thr His Trp Pro Trp Thr Phe Gly Gln Gly Thr Lys Val Glu Ile Lys
               100                 105                 110
```

<210> SEQ ID NO 304
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

```
Gln Val Ser Asn Arg Asp Ser
 1               5
```

<210> SEQ ID NO 305
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

```
Gly Val Pro Asp Arg Phe Ser Gly Ser Gly Ser Gly Thr Asp Phe Thr
 1               5                  10                  15
Leu Lys Ile Gly Arg Val Glu Ala Glu Asp Val Gly Val Tyr Phe Cys
                20                  25                  30
```

<210> SEQ ID NO 306
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

```
Asp Ile Val Met Thr Gln Thr Pro Pro Ser Leu Pro Val Asn Pro Gly
 1               5                  10                  15
Glu Pro Ala Ser Ile Ser Cys Arg Ser Ser Gln Ser Leu Leu His Ser
                20                  25                  30
Asn Gly Tyr Thr Tyr Leu His Trp Tyr Leu Gln Lys Pro Gly Gln Ser
            35                  40                  45
Pro Gln Leu Leu Ile Tyr Arg Val Ser Asn His Leu Ser Gly Val Pro
        50                  55                  60
Asp Arg Phe Ser Gly Ser Gly Ser Gly Ser Asp Phe Thr Leu Lys Ile
 65                  70                  75                  80
Ser Trp Val Glu Ala Glu Asp Val Gly Val Tyr Tyr Cys Met Gln Ala
                85                  90                  95
Thr Gln Phe Pro Leu Thr Phe Gly Pro Gly Thr Lys Val Asp Ile Lys
               100                 105                 110
Arg Thr Val Ala Ala Pro Ser Val Phe Ile Phe Pro Pro Ser Asp Glu
               115                 120                 125
Gln Leu Lys Ser Gly Thr Ala Ser Val Val Cys Leu Leu Asn Asn Phe
```

```
                130             135             140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 307
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 307

```
gatattgtga tgacccagac tccaccctcc ctgcccgtca accctggaga gccggcctcc    60
atctcttgca ggtctagtca gagcctcctg catagtaatg gatataccta tttgcattgg   120
tacctgcaga agccagggca gtctccacag ctcctgattt atagggtttc caatcatctt   180
tctggggtcc cagacaggtt tagtggcagt gggtcaggta gtgatttcac actgaaaatc   240
agctgggtgg aggctgagga tgttggggtt tattactgca tgcaagctac acagtttccg   300
ctcactttcg gccctgggac caaagtggat atcaaa                             336
```

<210> SEQ ID NO 308
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

```
Asp Ile Val Met Thr Gln Thr Pro Pro Ser Leu Pro Val Asn Pro Gly
1               5                   10                  15

Glu Pro Ala Ser Ile Ser Cys Arg Ser Ser Gln Ser Leu Leu His Ser
            20                  25                  30

Asn Gly Tyr Thr Tyr Leu His Trp Tyr Leu Gln Lys Pro Gly Gln Ser
        35                  40                  45

Pro Gln Leu Leu Ile Tyr Arg Val Ser Asn His Leu Ser Gly Val Pro
    50                  55                  60

Asp Arg Phe Ser Gly Ser Gly Ser Gly Ser Asp Phe Thr Leu Lys Ile
65                  70                  75                  80

Ser Trp Val Glu Ala Glu Asp Val Gly Val Tyr Tyr Cys Met Gln Ala
                85                  90                  95

Thr Gln Phe Pro Leu Thr Phe Gly Pro Gly Thr Lys Val Asp Ile Lys
            100                 105                 110
```

<210> SEQ ID NO 309
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 309

Asp Ile Val Met Thr Gln Thr Pro Pro Ser Leu Pro Val Asn Pro Gly
1               5                   10                  15

Glu Pro Ala Ser Ile Ser Cys
            20

<210> SEQ ID NO 310
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Arg Ser Ser Gln Ser Leu Leu His Ser Asn Gly Tyr Thr Tyr Leu His
1               5                   10                  15

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Arg Val Ser Asn His Leu Ser
1               5

<210> SEQ ID NO 312
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Gly Val Pro Asp Arg Phe Ser Gly Ser Gly Ser Gly Ser Asp Phe Thr
1               5                   10                  15

Leu Lys Ile Ser Trp Val Glu Ala Glu Asp Val Gly Val Tyr Tyr Cys
            20                  25                  30

<210> SEQ ID NO 313
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile

```
                65                  70                  75                  80
Ser Arg Val Glu Ala Glu Asp Val Gly Val Tyr Tyr Cys Met Gln Ala
                    85                  90                  95

Thr Gln Phe Pro Val Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
210                 215
```

```
<210> SEQ ID NO 314
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 314
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagctac acaatttccc     300
gtgacgttcg gccaagggac caaggtggaa atcaaa                               336
```

```
<210> SEQ ID NO 315
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
```

```
                     85                  90                  95

Thr Gln Phe Pro Val Thr Phe Gly Gln Gly Thr Lys Val Glu Ile Lys
                100                 105                 110

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Met Gln Ala Thr Gln Phe Pro Val Thr
1               5

<210> SEQ ID NO 317
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Asp Ile Val Met Thr Gln Thr Pro Leu Ser Ser Pro Val Thr Leu Gly
1               5                  10                  15

Gln Pro Ala Ser Ile Ser Cys Arg Ser Ser Gln Ser Leu Val His Ser
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
        50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Phe Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 318
<211> LENGTH: 336
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 318

```
gatattgtga tgacccagac tccactctcc tcacctgtca cccttggaca gccggcctcc      60
atctcctgca ggtctagtca aagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcgggg tt tattactgca tgcaagctac acaattcccc     300
ttcacttttg gccaggggac caagctggag atcaaa                                336
```

<210> SEQ ID NO 319
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Phe Thr Phe Gly Gln Gly Thr Lys Leu Glu Ile Lys
            100                 105                 110

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Met Gln Ala Thr Gln Phe Pro Phe Thr
1               5

<210> SEQ ID NO 321
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Asp Ile Val Met Thr Gln Thr Pro Pro Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Ser Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 322
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 322
gatattgtga tgacccagac tccaccctcc tcacccgtca cccttggaca gccggcctcc      60
atctcctgca ggtctagtca gagcctcgta cacagtgatg gaaacaccta cttgagttgg     120
cttcagcaga ggccaggcca gcctccaaga ctcctaattt ataagatttc taaccggttc     180
tctggggtcc cagacagatt cagtggcagt ggggcaggga cagatttcac actgaaaatc     240
agcagggtgg aagctgagga tgtcggggtt tattactgca tgcaagcttc acaatttcct     300
ctcactttcg gcggagggac caaggtggag atcaaa                               336

<210> SEQ ID NO 323
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

Asp Ile Val Met Thr Gln Thr Pro Pro Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
            35                  40                  45

```
Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Ser Gln Phe Pro Leu Thr Phe Gly Gly Gly Thr Lys Val Glu Ile Lys
                100                 105                 110

<210> SEQ ID NO 324
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Asp Ile Val Met Thr Gln Thr Pro Pro Ser Ser Pro Val Thr Leu Gly
 1               5                  10                  15

Gln Pro Ala Ser Ile Ser Cys
             20

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Met Gln Ala Ser Gln Phe Pro Leu Thr
 1               5

<210> SEQ ID NO 326
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Asp Ile Val Met Thr Gln Thr Pro Leu Ser Ser Pro Val Thr Leu Gly
 1               5                  10                  15

Gln Pro Ala Ser Ile Ser Cys Arg Ser Ser Gln Ser Leu Val His Ser
                 20                  25                  30

Asp Gly Asn Thr Tyr Leu Ser Trp Leu Gln Gln Arg Pro Gly Gln Pro
             35                  40                  45

Pro Arg Leu Leu Ile Tyr Lys Ile Ser Asn Arg Phe Ser Gly Val Pro
     50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95

Thr Gln Phe Pro Ile Thr Phe Gly Gln Gly Thr Arg Leu Glu Ile Lys
                100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
```

```
                130                 135                 140
Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215

<210> SEQ ID NO 327
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 327
gatattgtga tgacccagac tccactctcc tcacctgtca cccttggaca gccggcctcc     60
atctcctgca ggtctagtca aagcctcgta cacagtgatg gaaacaccta cttgagttgg    120
cttcagcaga ggccaggcca gcctccaaga ctcctaattt ataagatttc taaccggttc    180
tctggggtcc cagacagatt cagtggcagt ggggcaggga cagatttcac actgaaaatc    240
agcagggtgg aagctgagga tgtcggggtt tattactgca tgcaagctac acaatttcct    300
atcaccttcg gccaagggac acgactggag attaaa                              336

<210> SEQ ID NO 328
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Ile Thr Phe Gly Gln Gly Thr Arg Leu Glu Ile Lys
            100                 105                 110

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 329

Met Gln Ala Thr Gln Phe Pro Ile Thr
1               5

<210> SEQ ID NO 330
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Phe Gly Gln Gly Thr Arg Leu Glu Ile Lys
1               5                   10

<210> SEQ ID NO 331
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Asp Ile Val Met Thr Gln Thr Pro Leu Ser Leu Pro Val Thr Leu Gly
1               5                   10                  15

Gln Pro Ala Ser Ile Ser Cys Arg Ser Ser Gln Ser Leu Val Arg Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Thr Ile
65                  70                  75                  80

Ser Arg Val Glu Ala Glu Asp Val Gly Val Tyr Tyr Cys Met Gln Gly
                85                  90                  95

Thr Gln Phe Pro Leu Thr Phe Gly Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 332
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 332

```
gatattgtga tgacccagac tccactctcc ttacctgtca cccttggaca gccggcctcc      60
atctcctgca ggtctagtca aagcctcgta cgcagtgatg gaaacaccta cctgagttgg     120
cttcagcaga ggccaggcca gcctccaaga ctcctaattt ataagatttc taaccggttc     180
tctggggtcc cagacagatt cagtggcagt ggggcaggga cagatttcac actgacaatc     240
agcagggtgg aagctgagga tgtcggagtt tattactgca tgcaaggtac acaattcccg     300
ctcacttcg gcggagggac caaggtggag atcaaa                                336
```

<210> SEQ ID NO 333
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

```
Asp Ile Val Met Thr Gln Thr Pro Leu Ser Leu Pro Val Thr Leu Gly
1               5                   10                  15
Gln Pro Ala Ser Ile Ser Cys Arg Ser Ser Gln Ser Leu Val Arg Ser
            20                  25                  30
Asp Gly Asn Thr Tyr Leu Ser Trp Leu Gln Gln Arg Pro Gly Gln Pro
        35                  40                  45
Pro Arg Leu Leu Ile Tyr Lys Ile Ser Asn Arg Phe Ser Gly Val Pro
    50                  55                  60
Asp Arg Phe Ser Gly Ser Gly Ala Gly Thr Asp Phe Thr Leu Thr Ile
65                  70                  75                  80
Ser Arg Val Glu Ala Glu Asp Val Gly Val Tyr Tyr Cys Met Gln Gly
                85                  90                  95
Thr Gln Phe Pro Leu Thr Phe Gly Gly Gly Thr Lys Val Glu Ile Lys
            100                 105                 110
```

<210> SEQ ID NO 334
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

```
Asp Ile Val Met Thr Gln Thr Pro Leu Ser Leu Pro Val Thr Leu Gly
1               5                   10                  15
Gln Pro Ala Ser Ile Ser Cys
            20
```

<210> SEQ ID NO 335
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

```
Arg Ser Ser Gln Ser Leu Val Arg Ser Asp Gly Asn Thr Tyr Leu Ser
```

<210> SEQ ID NO 336
<211> LENGTH: 32
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 336

Gly Val Pro Asp Arg Phe Ser Gly Ser Gly Ala Gly Thr Asp Phe Thr
1               5                   10                  15

Leu Thr Ile Ser Arg Val Glu Ala Glu Asp Val Gly Val Tyr Tyr Cys
            20                  25                  30

<210> SEQ ID NO 337
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 337

Met Gln Gly Thr Gln Phe Pro Leu Thr
1               5

<210> SEQ ID NO 338
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 338

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Tyr Cys Leu Gln Ala
                85                  90                  95

Thr Gln Phe Pro Leu Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
        210                 215

<210> SEQ ID NO 339
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 339
gatattgtga tgacccagac tccactctcc tcacctgtca cccttggaca gccggcctcc    60
atctcctgca ggtctagtca agcctcgta cacagtgatg gaaacaccta cttgagttgg   120
cttcagcaga ggccaggcca gcctccaaga ctcctaattt ataagatttc taaccggttc   180
tctggggtcc cagacagatt cagtggcagt ggggcaggga cagatttcac actgaaaatc   240
agcagggtgg aagctgagga tgtcgggctt tattactgct tgcaagctac acaatttccc   300 ctgactttg gccaggggac caagctggag atcaaa                              336

<210> SEQ ID NO 340
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Leu Tyr Tyr Cys Leu Gln Ala
                85                  90                  95

Thr Gln Phe Pro Leu Thr Phe Gly Gln Gly Thr Lys Leu Glu Ile Lys
            100                 105                 110

<210> SEQ ID NO 341
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gly Val Pro Asp Arg Phe Ser Gly Ser Gly Ala Gly Thr Asp Phe Thr
1               5                   10                  15

Leu Lys Ile Ser Arg Val Glu Ala Glu Asp Val Gly Leu Tyr Tyr Cys
            20                  25                  30

<210> SEQ ID NO 342
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Leu Gln Ala Thr Gln Phe Pro Leu Thr
1               5

<210> SEQ ID NO 343
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 343
atggagactg ggctgcgctg gcttctcctg gtcgctgtgc tcaaaggtgt ccagtgt       57

<210> SEQ ID NO 344
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
atggagtttg ggctgagctg ggttttcctt gttgctatta taaaggtgt ccagtgt       57

<210> SEQ ID NO 345
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Gly Val Thr Ser Ala Pro Asp Thr Arg Pro Ala Pro Gly Ser Thr Ala
1               5                   10                  15

Pro Pro Ala His Gly Val Thr Ser Ala Pro Asp Thr Arg Pro Ala Pro
            20                  25                  30

Gly Ser Thr Ala Pro Pro Ala His
        35                  40

<210> SEQ ID NO 346
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

His Gly Val Thr Ser Ala Pro Asp Thr Arg Pro Ala Pro Gly Ser Thr
1               5                   10                  15

Ala Pro Pro

<210> SEQ ID NO 347
<211> LENGTH: 5

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Pro Asp Thr Arg Pro
1               5

<210> SEQ ID NO 348
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 348
gccgccacca tggagacaga cacactcctg ctatgggtgc tgctgctctg ggttccaggt    60
tccacaggt                                                            69

<210> SEQ ID NO 349
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 349
ggcggtggga gcggtggtgg ctccgggggc ggttccggtg ggggcggcag cagc          54

<210> SEQ ID NO 350
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 350
gagagcaagt acggccctcc ctgcccccct tgccctgccc ccgagttcct gggcggaccc    60
agcgtgttcc tgttcccccc caagcccaag gacaccctga tgatcagccg gacccccgag   120
gtgacctgcg tggtggtgga cgtgagccag gaagatcccg aggtccagtt caattggtac   180
gtggacggcg tggaagtgca caacgccaag accaagccca gagaggaaca gttcaacagc   240
acctaccggg tggtgtctgt gctgaccgtg ctgcaccagg actggctgaa cggcaaagaa   300
tacaagtgca aggtgtccaa caagggcctg cccagcagca tcgaaaagac catcagcaag   360
gccaagggcc agcctcgcga gccccaggtg tacaccctgc ctccctccca ggaagagatg   420
accaagaacc aggtgtccct gacctgcctg gtgaagggct tctacccag cgacatcgcc   480 gtggagtggg agagcaacgg ccagcctgag aacaactaca gaccaccc tcccgtgctg     540 gacagcgacg gcagcttctt cctgtacagc cggctgaccg tggacaagag ccggtggcag   600
gaaggcaacg tctttagctg cagcgtgatg cacgaggccc tgcacaacca ctacacccag   660
aagtccctga gcctgtccct gggcaag                                       687

<210> SEQ ID NO 351
<211> LENGTH: 216
<212> TYPE: DNA
<213> ORGANISM: Artificial Sequence

```
<220> FEATURE:
<223> OTHER INFORMATION: Description of Artificial Sequence: Synthetic
      polynucleotide

<400> SEQUENCE: 351
atgttctggg tgctggtggt ggtgggcggg gtgctggcct gctacagcct gctggtgaca    60
gtggccttca tcatcttttg ggtgcggagc aagcggagca gaggcggcca cagcgactac   120
atgaacatga cccccagacg gcctggcccc acccggaagc actaccagcc ctacgcccca   180
cccagggact tgccgcccta ccggtccggc ggaggg                             216

<210> SEQ ID NO 352
<211> LENGTH: 126
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 352
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 353
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 353
cgggtgaagt tcagcagaag cgccgacgcc cctgcctacc agcagggcca gaatcagctg    60
tacaacgagc tgaacctggg cagaagggaa gagtacgacg tcctggataa gcggagaggc   120
cgggaccctg agatgggcgg caagcctcgg cggaagaacc cccaggaagg cctgtataac   180
gaactgcaga agacaagat ggccgaggcc tacagcgaga tcggcatgaa gggcgagcgg   240
aggcggggca agggccacga cggcctgtat cagggcctgt ccaccgccac caaggatacc   300
tacgacgccc tgcacatgca ggccctgccc ccaagg                             336

<210> SEQ ID NO 354
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
ctcgagggcg gcggagaggg cagaggaagt cttctaacat gcggtgacgt ggaggagaat    60
cccggccctc gc                                                        72

<210> SEQ ID NO 355
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 355
```

```
atgagcgagc tgattaagga gaacatgcac atgaagctgt acatggaggg caccgtggac      60
aaccatcact tcaagtgcac atccgagggc gaaggcaagc cctacgaggg cacccagacc     120
atgagaatca aggtggtcga gggcggccct ctccccttcg ccttcgacat cctggctact     180
agcttcctct acggcagcaa gaccttcatc aaccacaccc agggcatccc cgacttcttc     240
aagcagtcct ccctgagggc cttcacatgg gagagagtca ccacatacga agacgggggc     300
gtgctgaccg ctaccagga caccagcctc caggacggct gcctcatcta caacgtcaag     360
atcagagggg tgaacttcac atccaacggc cctgtgatgc agaagaaaac actcggctgg     420
gaggccttca ccgagacgct gtaccccgct gacggcggcc tggaaggcag aaacgacatg     480
gccctgaagc tcgtgggcgg gagccatctg atcgcaaaca tcaagaccac atatagatcc     540
aagaaacccg ctaagaacct caagatgcct ggcgtctact atgtggacta cagactggaa     600
agaatcaagg aggccaacaa cgaaacatac gtcgagcagc acgaggtggc agtggccaga     660
tactgcgacc tccctagcaa actggggcac aagcttaatt aa                        702
```

<210> SEQ ID NO 356
<211> LENGTH: 8219
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 356

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt gcgctgcttc gcgatgtacg ggccagatat acgcgttgac     240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
```

```
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg gccgcgctga tcttcagacc tggaggagga    1560
gatatgaggg acaattggag aagtgaatta tataaatata aagtagtaaa aattgaacca    1620
ttaggagtag cacccaccaa ggcaaagaga agagtggtgc agagagaaaa aagagcagtg    1680
ggaataggag ctttgttcct tgggttcttg ggagcagcag gaagcactat gggcgcagcg    1740
tcaatgacgc tgacggtaca ggccagacaa ttattgtctg gtatagtgca gcagcagaac    1800
aatttgctga gggctattga ggcgcaacag catctgttgc aactcacagt ctggggcatc    1860
aagcagctcc aggcaagaat cctggctgtg gaaagatacc taaaggatca acagctcctg    1920
gggatttggg gttgctctgg aaaactcatt tgcaccactg ctgtgccttg gaatgctagt    1980
tggagtaata aatctctgga acagatttgg aatcacacga cctggatgga gtgggacaga    2040
gaaattaaca attacacaag cttaatacac tccttaattg aagaatcgca aaaccagcaa    2100
gaaaagaatg aacaagaatt attggaatta gataaatggg caagtttgtg gaattggttt    2160
aacataacaa attggctgtg gtatataaaa ttattcataa tgatagtagg aggcttggta    2220
ggtttaagaa tagtttttgc tgtactttct atagtgaata gagttaggca gggatattca    2280
ccattatcgt ttcagaccca cctcccaacc ccgaggggac ccgacaggcc cgaaggaata    2340
gaagaagaag gtggagagag agacagagac agatccattc gattagtgaa cggatcggca    2400
ctgcgtgcgc caattctgca gacaaatggc agtattcatc cacaatttta aagaaaagg    2460 ggggattggg gggtacagtg caggggaaag aatagtagac ataatagcaa cagacataca    2520
aactaaagaa ttacaaaaac aaattacaaa aattcaaaat tttcgggttt attacaggga    2580
cagcagagat ccagtttggt tagtaccggg cccgctctag ccgtgaggct ccggtgcccg    2640
tcagtgggca gagcgcacat cgcccacagt ccccgagaag ttggggggag ggtcggcaa    2700 ttgaaccggt gcctagagaa ggtggcgcgg ggtaaactgg gaaagtgatg tcgtgtactg    2760
gctccgcctt tttcccgagg gtgggggaga accgtatata agtgcagtag tcgccgtgaa    2820
cgttcttttt cgcaacgggt ttgccgccag aacacaggta agtgccgtgt gtggttcccg    2880
cgggcctggc ctctttacgg gttatggcc ttgcgtgcct tgaattactt ccacctggct    2940
gcagtacgtg attcttgatc ccgagcttcg ggttggaagt gggtgggaga gttcgaggcc    3000
ttgcgcttaa ggagcccctt cgcctcgtgc ttgagttgag gcctggcctg ggcgctgggg    3060
ccgccgcgtg cgaatctggt ggcaccttcg cgcctgtctc gctgctttcg ataagtctct    3120
agccatttaa aattttttgat gacctgctgc gacgcttttt ttctggcaag atagtcttgt    3180
aaatgcgggc caagatctgc acactggtat ttcggttttt ggggccgcgg gcggcgacgg    3240
ggcccgtgcg tccagcgca catgttcggc gaggcgggc ctgcgagcgc ggccaccgag    3300
aatcggacgg gggtagtctc aagctggccg gcctgctctg tgcctggcc tcgcgccgcc    3360 gtgtatcgcc ccgccctggg cggcaaggct ggcccggtcg caccagttg cgtgagcgga    3420 aagatggccg cttcccggcc ctgctgcagg gagctcaaaa tggaggacgc ggcgctcggg    3480
agagcgggcg ggtgagtcac ccacacaaag gaaaagggcc tttccgtcct cagccgtcgc    3540
ttcatgtgac tccacggagt accgggcgcc gtccaggcac ctcgattagt tctcgagctt    3600
ttggagtacg tcgtctttag gttgggggga ggggttttat gcgatggagt ttccccacac    3660
```

```
tgagtgggtg gagactgaag ttaggccagc ttggcacttg atgtaattct ccttggaatt    3720
tgcccttttt gagtttggat cttggttcat tctcaagcct cagacagtgg ttcaaagttt    3780
ttttcttcca tttcaggtgt cgtgagcggc cgctgaactg aattcatcga cgttaactat    3840
tctagagtac ccgggctagg atccgcccct ctccctcccc cccccctaac gttactggcc    3900
gaagccgctt ggaataaggc cggtgtgcgt ttgtctatat gttattttcc accatattgc    3960
cgtcttttgg caatgtgagg gcccggaaac ctggccctgt cttcttgacg agcattccta    4020
ggggtctttc ccctctcgcc aaaggaatgc aaggtctgtt gaatgtcgtg aaggaagcag    4080
ttcctctgga agcttcttga agacaaacaa cgtctgtagc gacccttgc aggcagcgga    4140
accccccacc tggcgacagg tgcctctgcg gccaaaagcc acgtgtataa gatacacctg    4200
caaaggcggc acaaccccag tgccacgttg tgagttggat agttgtggaa agagtcaaat    4260
ggctctcctc aagcgtattc aacaaggggc tgaaggatgc ccagaaggta ccccattgta    4320
tgggatctga tctggggcct cggtgcacat gctttacatg tgtttagtcg aggttaaaaa    4380
aacgtctagg ccccccgaac cacggggacg tggttttcct ttgaaaaaca cgatgataat    4440
atggccacat ggaagatgcc aaaaacatta agaagggccc agcgccattc tacccactcg    4500
aagacgggac cgccggcgag cagctgcaca aagccatgaa cgctacgcc ctggtgcccg    4560
gcaccatcgc ctttaccgac gcacatatcg aggtggacat tacctacgcc gagtacttcg    4620
agatgagcgt tcggctggca gaagctatga gcgctatgg gctgaataca aaccatcgga    4680
tcgtggtgtg cagcgagaat agcttgcagt tcttcatgcc cgtgttgggt gccctgttca    4740
tcggtgtggc tgtggcccca gctaacgaca tctacaacga gcgcgagctg ctgaacagca    4800
tgggcatcag ccagcccacc gtcgtattcg tgagcaagaa agggctgcaa aagatcctca    4860
acgtgcaaaa gaagctaccg atcatacaaa agatcatcat catggatagc aagaccgact    4920
accagggctt ccaaagcatg tacaagtagc ggccgcataa cttcgtatag tataaattat    4980
acgaagttat aagccttgtt aacgcgcggt gaccctcgag gtcgacggta tcgataagct    5040
cgcttcacga gatcatgttt aagggttccg gttccactag gtacaattcg atatcaagct    5100
tatcgataat caacctctgg attacaaaat ttgtgaaaga ttgactggta ttcttaacta    5160
tgttgctcct tttacgctat gtggatacgc tgctttaatg cctttgtatc atgctattgc    5220
ttcccgtatg gctttcattt tctcctcctt gtataaatcc tggttgctgt ctctttatga    5280
ggagttgtgg cccgttgtca ggcaacgtgg cgtggtgtgc actgtgtttg ctgacgcaac    5340
ccccactggt tggggcattg ccaccacctg tcagctcctt tccgggactt tcgctttccc    5400
cctccctatt gccacggcgg aactcatcgc cgcctgcctt gcccgctgct ggacaggggc    5460
tcggctgttg ggcactgaca attccgtggt gttgtcgggg aaatcatcgt cctttccttg    5520
gctgctcgcc tgtgttgcca cctggattct gcgcgggacg tccttctgct acgtcccttc    5580
ggccctcaat ccagcggacc ttccttcccg cggcctgctg ccggctctgc ggcctcttcc    5640
gcgtcttcgc cttcgccctc agacgagtcg gatctccctt gggccgcct cccgcatcg    5700
ataccgtcga cctcgatcga gacctagaaa acatggagc aatcacaagt agcaatacag    5760
cagctaccaa tgctgattgt gcctggctag aagcacaaga ggaggaggag gtgggttttc    5820
cagtcacacc tcaggtacct ttaagaccaa tgacttacaa ggcagctgta gatcttagcc    5880
acttttttaaa agaaaagggg ggactggaag ggctaattca ctcccaacga agacaagata    5940
tccttgatct gtggatctac cacacacaag gctacttccc tgattggcag aactacacac    6000
cagggccagg gatcagatat ccactgacct ttggatggtg ctacaagcta gtaccagttg    6060
```

```
agcaagagaa ggtagaagaa gccaatgaag gagagaacac ccgcttgtta caccctgtga    6120
gcctgcatgg gatggatgac ccggagagag aagtattaga gtggaggttt gacagccgcc    6180
tagcatttca tcacatggcc cgagagctgc atccggactg tactgggtct ctctggttag    6240
accagatctg agcctgggag ctctctggct aactagggaa cccactgctt aagcctcaat    6300
aaagcttgcc ttgagtgctt caagtagtgt gtgcccgtct gttgtgtgac tctggtaact    6360
agagatccct cagacccttt tagtcagtgt ggaaaatctc tagcagcatg tgagcaaaag    6420
gccagcaaaa ggccaggaac cgtaaaaagg ccgcgttgct ggcgtttttc cataggctcc    6480
gcccccctga cgagcatcac aaaaatcgac gctcaagtca gaggtggcga aacccgacag    6540
gactataaag ataccaggcg tttccccctg gaagctccct cgtgcgctct cctgttccga    6600
ccctgccgct taccggatac ctgtccgcct ttctcccttc gggaagcgtg gcgctttctc    6660
atagctcacg ctgtaggtat ctcagttcgg tgtaggtcgt tcgctccaag ctgggctgtg    6720
tgcacgaacc ccccgttcag cccgaccgct gcgccttatc cggtaactat cgtcttgagt    6780
ccaacccggt aagacacgac ttatcgccac tggcagcagc cactggtaac aggattagca    6840
gagcgaggta tgtaggcggt gctacagagt tcttgaagtg gtggcctaac tacggctaca    6900
ctagaagaac agtatttggt atctgcgctc tgctgaagcc agttaccttc ggaaaaagag    6960
ttggtagctc ttgatccggc aaacaaacca ccgctggtag cggtggtttt tttgtttgca    7020
agcagcagat tacgcgcaga aaaaaaggat ctcaagaaga tcctttgatc ttttctacgg    7080
ggtctgacgc tcagtggaac gaaaactcac gttaagggat tttggtcatg agattatcaa    7140
aaaggatctt cacctagatc cttttaaatt aaaaatgaag ttttaaatca atctaaagta    7200
tatatgagta aacttggtct gacagttacc aatgcttaat cagtgaggca cctatctcag    7260
cgatctgtct atttcgttca tccatagttg cctgactccc cgtcgtgtag ataactacga    7320
tacgggaggg cttaccatct ggccccagtg ctgcaatgat accgcgagac ccacgctcac    7380
cggctccaga tttatcagca ataaaccagc cagccggaag ggccgagcgc agaagtggtc    7440
ctgcaacttt atccgcctcc atccagtcta ttaattgttg ccgggaagct agagtaagta    7500
gttcgccagt taatagtttg cgcaacgttg ttgccattgc tacaggcatc gtggtgtcac    7560
gctcgtcgtt tggtatggct tcattcagct ccggttccca acgatcaagg cgagttacat    7620 gatccccat gttgtgcaaa aaagcggtta gctccttcgg tcctccgatc gttgtcagaa    7680
gtaagttggc cgcagtgtta tcactcatgg ttatggcagc actgcataat tctcttactg    7740
tcatgccatc cgtaagatgc ttttctgtga ctggtgagta ctcaaccaag tcattctgag    7800
aatagtgtat gcggcgaccg agttgctctt gcccggcgtc aatacgggat aataccgcgc    7860
cacatagcag aactttaaaa gtgctcatca ttggaaaacg ttcttcgggg cgaaaactct    7920
caaggatctt accgctgttg agatccagtt cgatgtaacc cactcgtgca cccaactgat    7980
cttcagcatc ttttactttc accagcgttt ctgggtgagc aaaaacagga aggcaaaatg    8040
ccgcaaaaaa gggaataagg gcgacacgga aatgttgaat actcatactc ttcctttttc    8100
aatattattg aagcatttat cagggttatt gtctcatgag cggatacata tttgaatgta    8160
tttagaaaaa taaacaaata ggggttccgc gcacatttcc ccgaaaagtg ccacctgac     8219
```

<210> SEQ ID NO 357
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (9)..(9)
<223> OTHER INFORMATION: Lys or Ile

<400> SEQUENCE: 357

Tyr Ile Ser Ser Ser Gly Xaa Thr Xaa Tyr Tyr Ala Asp Ser Val Lys
1               5                   10                  15

Gly

<210> SEQ ID NO 358
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn or Arg
<220> FEATURE:
<221> NAME/KEY: MOD_RES
<222> LOCATION: (3)..(3)
<223> OTHER INFORMATION: Leu or Ile

<400> SEQUENCE: 358

Glu Xaa Xaa Gly Tyr Cys Ser Gly Gly Ser Cys Tyr Tyr Tyr Tyr
1               5                   10                  15

Met Asp Val

<210> SEQ ID NO 359
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn or Arg
<220> FEATURE:
<221> NAME/KEY: MOD_RES
<222> LOCATION: (3)..(3)
<223> OTHER INFORMATION: Leu or Ile

<400> SEQUENCE: 359

Glu Xaa Xaa Gly Tyr Cys Thr Gly Gly Asn Cys Phe Tyr Tyr Tyr
1               5                   10                  15

Met Asp Val

<210> SEQ ID NO 360
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asn or Arg
<220> FEATURE:
```

<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (10)..(10)
<223> OTHER INFORMATION: Asn or Ser
<220> FEATURE:
<221> NAME/KEY: MOD_RES
<222> LOCATION: (12)..(12)
<223> OTHER INFORMATION: Phe or Tyr

<400> SEQUENCE: 360

Glu Xaa Xaa Gly Tyr Cys Xaa Gly Gly Xaa Cys Xaa Tyr Tyr Tyr Tyr
1               5                   10                  15

Met Asp Val

<210> SEQ ID NO 361
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp or Asn
<220> FEATURE:
<221> NAME/KEY: MOD_RES
<222> LOCATION: (3)..(3)
<223> OTHER INFORMATION: Ile or Leu

<400> SEQUENCE: 361

Glu Xaa Xaa Gly Tyr Cys Ser Gly Gly Ser Cys Phe Tyr Tyr Tyr Tyr
1               5                   10                  15

Met Asp Val

<210> SEQ ID NO 362
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Asp, Asn or Arg
<220> FEATURE:
<221> NAME/KEY: MOD_RES
<222> LOCATION: (3)..(3)
<223> OTHER INFORMATION: Leu or Ile
<220> FEATURE:
<221> NAME/KEY: MOD_RES
<222> LOCATION: (7)..(7)
<223> OTHER INFORMATION: Thr or Ser
<220> FEATURE:
<221> NAME/KEY: MOD_RES
<222> LOCATION: (10)..(10)
<223> OTHER INFORMATION: Asn or Ser
<220> FEATURE:
<221> NAME/KEY: MOD_RES
<222> LOCATION: (12)..(12)
<223> OTHER INFORMATION: Phe or Tyr

<400> SEQUENCE: 362

Glu Xaa Xaa Gly Tyr Cys Xaa Gly Gly Xaa Cys Xaa Tyr Tyr Tyr Tyr

Met Asp Val

<210> SEQ ID NO 363
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met or Leu
<220> FEATURE:
<221> NAME/KEY: MOD_RES
<222> LOCATION: (8)..(8)
<223> OTHER INFORMATION: Leu, Ile, Phe or Val

<400> SEQUENCE: 363

Xaa Gln Ala Thr Gln Phe Pro Xaa Thr
1               5

<210> SEQ ID NO 364
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: His or Arg

<400> SEQUENCE: 364

Arg Ser Ser Gln Ser Leu Val Xaa Ser Asp Gly Asn Thr Tyr Leu Ser
1               5                   10                  15

<210> SEQ ID NO 365
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met or Leu
<220> FEATURE:
<221> NAME/KEY: MOD_RES
<222> LOCATION: (3)..(3)
<223> OTHER INFORMATION: Ala or Gly
<220> FEATURE:
<221> NAME/KEY: MOD_RES
<222> LOCATION: (8)..(8)
<223> OTHER INFORMATION: Leu, Ile, Phe or Val

<400> SEQUENCE: 365

Xaa Gln Xaa Thr Gln Phe Pro Xaa Thr
1               5

<210> SEQ ID NO 366
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<221> NAME/KEY: MOD_RES
<222> LOCATION: (7)..(7)
<223> OTHER INFORMATION: Val or Leu
<220> FEATURE:
<221> NAME/KEY: MOD_RES
<222> LOCATION: (8)..(8)
<223> OTHER INFORMATION: His or Arg
<220> FEATURE:
<221> NAME/KEY: MOD_RES
<222> LOCATION: (10)..(10)
<223> OTHER INFORMATION: Asp or Asn
<220> FEATURE:
<221> NAME/KEY: MOD_RES
<222> LOCATION: (12)..(12)
<223> OTHER INFORMATION: Tyr or Asn
<220> FEATURE:
<221> NAME/KEY: MOD_RES
<222> LOCATION: (16)..(16)
<223> OTHER INFORMATION: Ser or His

<400> SEQUENCE: 366

Arg Ser Ser Gln Ser Leu Xaa Xaa Ser Xaa Gly Xaa Thr Tyr Leu Xaa
1               5                   10                  15

<210> SEQ ID NO 367
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (2)..(2)
<223> OTHER INFORMATION: Ile or Val
<220> FEATURE:
<221> NAME/KEY: MOD_RES
<222> LOCATION: (5)..(5)
<223> OTHER INFORMATION: Arg or His
<220> FEATURE:
<221> NAME/KEY: MOD_RES
<222> LOCATION: (6)..(6)
<223> OTHER INFORMATION: Phe or Leu

<400> SEQUENCE: 367

Xaa Xaa Ser Asn Xaa Xaa Ser
1               5

<210> SEQ ID NO 368
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Met or Leu
<220> FEATURE:
<221> NAME/KEY: MOD_RES
<222> LOCATION: (3)..(3)
<223> OTHER INFORMATION: Ala or Gly
<220> FEATURE:
<221> NAME/KEY: MOD_RES
<222> LOCATION: (4)..(4)
<223> OTHER INFORMATION: Thr or Ser
<220> FEATURE:
<221> NAME/KEY: MOD_RES
<222> LOCATION: (8)..(8)
<223> OTHER INFORMATION: Leu, Ile, Phe or Val

```
<400> SEQUENCE: 368

Xaa Gln Xaa Xaa Gln Phe Pro Xaa Thr
1               5

<210> SEQ ID NO 369
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys or Arg
<220> FEATURE:
<221> NAME/KEY: MOD_RES
<222> LOCATION: (5)..(5)
<223> OTHER INFORMATION: Ser or Asn
<220> FEATURE:
<221> NAME/KEY: MOD_RES
<222> LOCATION: (6)..(6)
<223> OTHER INFORMATION: Val or Leu
<220> FEATURE:
<221> NAME/KEY: MOD_RES
<222> LOCATION: (9)..(9)
<223> OTHER INFORMATION: Ser or Asn
<220> FEATURE:
<221> NAME/KEY: MOD_RES
<222> LOCATION: (12)..(12)
<223> OTHER INFORMATION: Asn or Lys
<220> FEATURE:
<221> NAME/KEY: MOD_RES
<222> LOCATION: (13)..(13)
<223> OTHER INFORMATION: Lys or Leu
<220> FEATURE:
<221> NAME/KEY: MOD_RES
<222> LOCATION: (17)..(17)
<223> OTHER INFORMATION: Ala or Ser

<400> SEQUENCE: 369

Xaa Ser Ser Gln Xaa Xaa Leu Tyr Xaa Ser Asn Xaa Xaa Asn Tyr Leu
1               5                   10                  15

Xaa

<210> SEQ ID NO 370
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser or Asn

<400> SEQUENCE: 370

Gln Gln Tyr Tyr Xaa Thr Pro Phe Thr
1               5

<210> SEQ ID NO 371
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

<400> SEQUENCE: 371

His His His His His His
1               5